United States Patent
Bingel et al.

(10) Patent No.: US 6,492,539 B1
(45) Date of Patent: Dec. 10, 2002

(54) PREPARATION OF PREPARING SUBSTITUTED INDANONES

(75) Inventors: Carsten Bingel, Kriftel; Markus Goeres, Eschborn; Volker Fraaije, Frankfurt; Andreas Winter, Glashütten, all of (DE)

(73) Assignee: Basell Polypropylen GmbH, Mainz (DE)

( * ) Notice: Subject to any disclaimer, the term of this patent is extended or adjusted under 35 U.S.C. 154(b) by 0 days.

(21) Appl. No.: 09/380,396

(22) PCT Filed: Mar. 5, 1998

(86) PCT No.: PCT/EP98/01232

§ 371 (c)(1),
(2), (4) Date: Sep. 1, 1999

(87) PCT Pub. No.: WO98/40331

PCT Pub. Date: Sep. 17, 1998

(30) Foreign Application Priority Data

Mar. 7, 1997 (DE) .......................... 197 09 402
Apr. 2, 1997 (DE) .......................... 197 13 546

(51) Int. Cl.$^7$ .......................... C07F 17/00; B01J 31/00; C07C 45/00
(52) U.S. Cl. .............................. 556/11; 556/12; 556/53; 502/103; 502/117; 526/160; 526/943; 568/312; 568/314; 585/25; 585/26
(58) Field of Search ............................... 568/312, 314; 556/11, 12, 53; 502/103, 117; 526/160, 943; 585/25, 26

(56) References Cited

U.S. PATENT DOCUMENTS

| 4,070,539 A | 1/1978 | Cragoe et al. | 560/56 |
| 5,489,712 A | 2/1996 | Bhattacharya | 568/312 |
| 5,559,277 A | 9/1996 | Beller et al. | 585/469 |
| 5,770,753 A | 6/1998 | Kueber et al. | 556/11 |

FOREIGN PATENT DOCUMENTS

| CA | 2175135 | 10/1996 |
| DE | 195 15 444 | 11/1996 |
| EP | 576 970 | 1/1994 |
| EP | 587 050 | 3/1994 |
| EP | 629 632 | 12/1994 |
| EP | 690 046 | 1/1996 |
| FR | 2 159 497 | 6/1973 |

OTHER PUBLICATIONS

J. Med. Chem., vol. 21, 437–73 (1978).
J. Org. Chem., vol. 21, 1956, 1120–1123 (1956).
Chem. Pharm. Bull., vol. 31, 3113–28 (1983).
J. Chem. Soc., 72, 1639–42 (1972).

Primary Examiner—Porfirio Nazario-Gonzalez
(74) Attorney, Agent, or Firm—Keil & Weinkauf

(57) ABSTRACT a process for the preparation of indanones of the formula II from, indanones of the formula I or of indanones of the formula IIa from indanones of the formula Ia

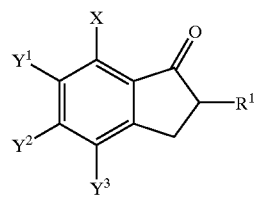
(I)

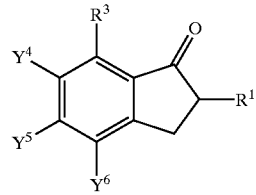

(II)

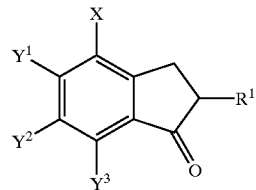

(Ia)

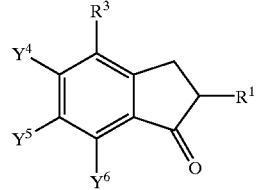

(IIa)

comprises reacting an indanone of the formula I or Ia with a coupling component.

15 Claims, No Drawings

PREPARATION OF PREPARING SUBSTITUTED INDANONES

The present invention relates to a simple and economically interesting process for preparing substituted indanones.

Substituted indanones are important intermediates for preparing active compounds in the fields of pharmacy and crop protection (cf. S. J. deSolms et al., J. Med. Chem., 1978, 21, 437) and for preparing metallocene complexes (cf. Chemie in unserer Zeit, 1994, 28, 204, 205). In particular, substituted indanones can be used to prepare bridged chiral metallocenes which are of great importance as highly active catalysts in olefin polymerization (cf. EP-A 129 368). The catalyst properties can be influenced in a targeted manner by variation of the ligand system, eg. by substitution. This makes it possible to achieve the desired degree of change in the polymer yield, the tacticity or the melting point of the polymers (New J. Chem., 1990, 14, 499; Organomet., 1990, 9, 3098; Angew. Chem., 1990, 102, 339; EP-A 316 155; EP-A 351 392). Bridged zirconocenes containing, as π ligands, substituted indenyl radicals which bear the bridge in: position 1, preferably a hydrocarbon radical in position 2 and a hydrocarbon radical, preferably an aryl radical, in position 4 have been found to be particularly active and stereoselective catalyst systems (EP 0 576 970 A1; EP 0 629 632 A2). The ligand systems used for these highly active metallocenes are prepared from the corresponding indenes which are in turn obtained from indanones which are substituted in the appropriate positions (EP 0 576 970 A1; EP 0 629 632 A2). These indanones are synthesized from commercially available precursors or precursors known in the literature, for example as follows:

EP 0 576 970 A1:

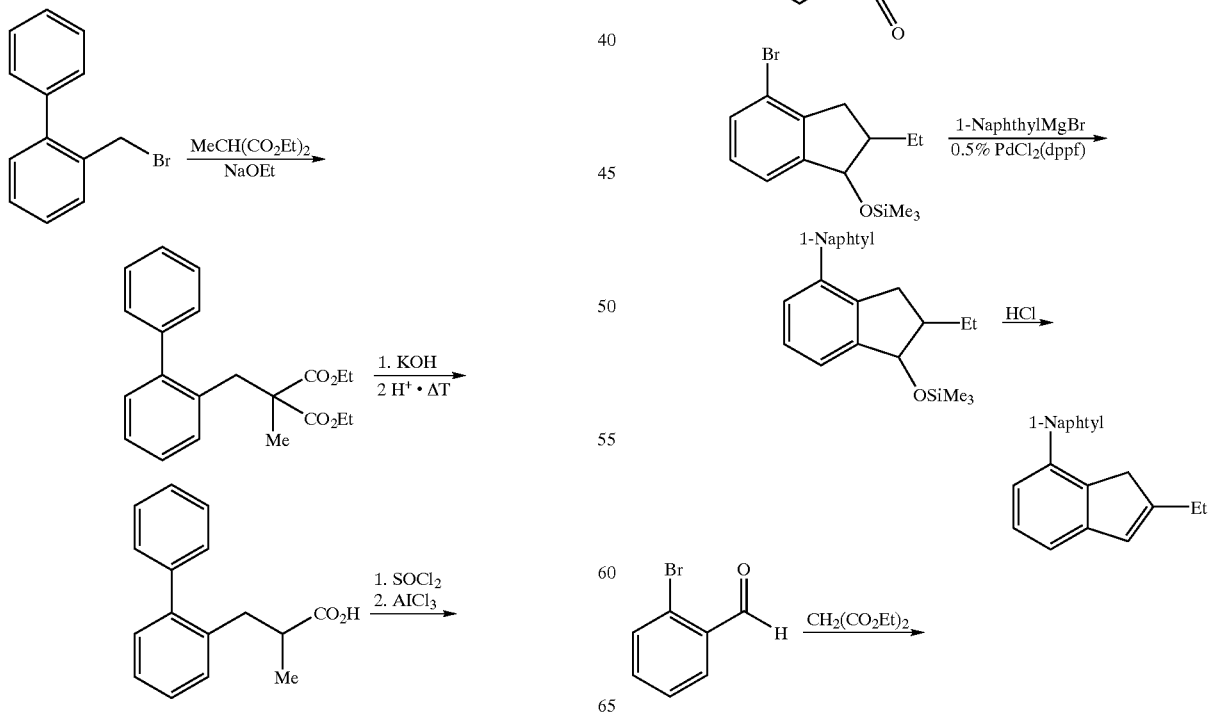

The 2-methyl-4-phenylindanone is converted into the corresponding indene, for example by reduction of the ketone function to the alcohol and subsequent dehydration.

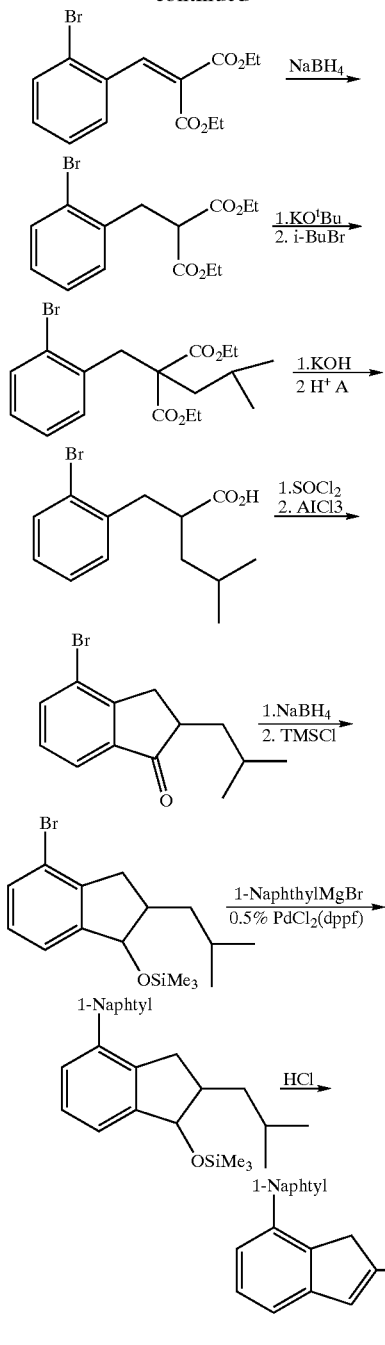

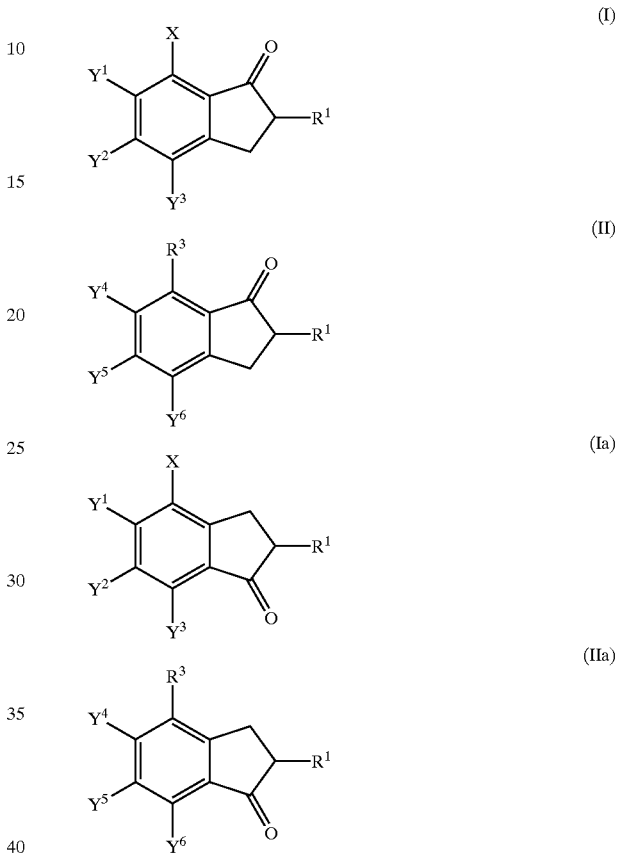

The three synthetic routes shown by way of example go through 2-, 4-substituted indanones which have in each case been obtained by Friedel-Crafts cyclization of the corresponding 3-arylpropionic acids. The syntheses are multi-stage processes in which relatively expensive starting compounds are used. Furthermore, in the syntheses disclosed in EP 0 629 632, the introduction of a protective group cannot be avoided. The processes shown are thus very costly routes.

It is therefore an object of the present invention to find a simple, flexible, inexpensive process for preparing substituted indanones which are important intermediates for preparing active compounds and metallocene complexes.

We have now surprisingly found that substituted indanones which contain a leaving group can be used to prepare, in a simple manner, other indanones which can be used, inter alia, for preparing active compounds and metallocene complexes.

The present invention accordingly provides a process for the preparation of indanones of the formula II from indanones of the Formula I or of indanones of the formula IIa from indanones of the formula Ia which comprises reacting an indanone of the formula I or Ia with a coupling component, where, in the formulae I, Ia, II and IIa, $R^1$ is a $C_1-C_{40}$-group such as a $C_1-C_{40}$-hydrocarbon group which is bound via a carbon atom and may bear one or more identical or different heteroatom-containing radicals as substituents, eg. a linear, branched or cyclic $C_1-C_{20}$-alkyl group which may bear one or more identical or different halogen, OH, $OR^2$, $SR^2NR^2{}_2$—, $PR^2{}_2$—, —$SiR^2{}_3$ or —$OSiR^2{}_3$ substituents, a $C_6-C_{22}$-aryl group which may bear one or more identical or different halogen, OH, $OR^2$, $SR^2NR^2{}_2$—, $PR^2{}_2$—, —$SiR^2{}_3$ or —$OSiR^2{}_3$ substituents, a $C_7-C_{20}$-alkylaryl group or a $C_7-C_{20}$-arylalkyl group, where the alkyl part may bear one or more identical or different halogen, OH, $OR^2$, $SR^2NR^2{}_2$—, $PR^2{}_2$—, —$SiR^2{}_3$ or —$OSiR^2{}_3$ substituents and the aryl part may bear one or more identical or different halogen, OH, $OR^2$, $SR^2NR^2{}_2$—, $PR^2{}_2$—, —$SiR^2{}_3$ or —$OSiR^2{}_3$ substituents, a $C_2-C_{10}$-alkenyl group which may bear one or more identical or different halogen, OH, $OR^2$, $SR^2NR^2{}_2$—, $PR^2{}_2$—, —$SiR^2{}_3$ or —$OSiR^2{}_3$ substituents, a $C_2-C_{20}$-alkynyl group which may bear one or more identical or different halogen, OH, $OR^2$, $SR^2NR^2{}_2$—, $PR^2{}_2$—, —$SiR^2{}_3$ or —$OSiR^2{}_3$ substituents, a $C_8-C_{12}$-arylalkenyl group, where the alkenyl part may bear one or, more identical or different halogen, OH, $OR^2$, $SR^2NR^2_2$—, $PR^2_2$—, —$SiR^2_3$ or —$OSiR^2_3$ substituents and the aryl part may bear one or more identical or different halogen, OH, $OR^2$, $SR^2NR^2_2$—, $PR^2_2$—, —$SiR^2_3$ or —$OSiR^2_3$ substituents, or $R^1$ is an $OR^2$, $SR^2$, $NR^2_2$, $PR^2_2$, $SiR^2_3$ or $OSiR^2_3$ group, where $R^2$ are identical or different and are each a $C_1$–$C_{20}$-hydrocarbon group such as a $C_1$–$C_{10}$-alkyl group or $C_6$–$C_{14}$-aryl group which may each bear one or more identical or different halogen, OH, $OR^2$, $SR^2NR^2_2$—, $PR^2_2$—, —$SiR^2_3$ or —$OSiR^2_3$ substituents or two radicals $R^2$ may be joined to form a ring system, or $R^1$ is a $C_1$–$C_{20}$-heterocyclic group which is bound via a carbon atom and may in turn bear $C_1$–$C_{20}$-radicals or heteroatoms as substituents, x is a leaving group such as a diazonium group, a halogen atom or a $C_1$–$C_{40}$-, preferably $C_1$–$C_{10}$-group which is bound via a heteroatom such as an atom of Group 13, 14, 15 or 16 of the Periodic Table of the Elements, eg. boron, silicon, tin, oxygen or sulfur, for example $C_1$–$C_{40}$-alkylsulfonate, $C_1$–$C_{40}$-haloalkylsulfonate, $C_6$–$C_{40}$-arylsulfonate, $C_6$–$C_{40}$-haloarylsulfonate, $C_7$–$C_{40}$-arylalkysulfonate, $C_7$–$C_{40}$-haloarylalkylsulfonate, $C_1$–$C_{40}$-alkylcarboxylate, $C_1$–$C_{40}$-haloalkylcarboxylate, $C_6$–$C_{40}$-arylcarboxylate, $C_6$–$C_{40}$-haloarylcarboxylate, $C_7$–$C_{40}$-arylalkylcarboxylate, $C_7$–$C_{40}$-haloarylalkylcarboxylate, formate, $C_1$–$C_{40}$-alkyl carbonate, $C_1$–$C_{40}$-haloalkyl carbonate, $C_6$–$C_{40}$-aryl carbonate, $C_6$–$C_{40}$-haloaryl carbonate, $C_7$–$C_{40}$-arylalkyl carbonate, $C_7$–$C_{40}$-haloarylalkyl carbonate, $C_1$–$C_{40}$-alkyl phosphonate, $C_1$–$C_{40}$-haloalkyl phosphonate, $C_6$–$C_{40}$-aryl phosphonate, $C_6$–$C_{40}$-haloaryl phosphonate, $C_7$–$C_{40}$-arylalkyl phosphonate or $C_7$–$C_{40}$-haloarylalkyl phosphonate, $R^3$ is a $C_1$–$C_{40}$-hydrocarbon group which is bound via a carbon atom and may bear one or more identical or different heteroatom-containing radicals as substituents, for example a linear, branched or cyclic $C_1$–$C_{20}$-alkyl group which may bear one or more identical or different halogen, OH, $OR^2$, $SR^2$, $NR^2_2$—, $PR^2_2$—, —$SiR^2_3$ or —$OSiR^2_3$ substituents, a $C_6$–$C_{22}$-aryl group which may bear one or more identical or different halogen, $OR^2$, $SR^2$, $NR^2_2$—, $NH_2$, —$N_2H_3$, $NO_2$, CN, $CO_2R^2$, CHO, $COR^2$, $PR^2_2$—, —$SiR^2_3$ or —$OSiR^2_3$ substituents, a $C_7$–$C_{15}$-alkylaryl group or $C_7$–$C_{15}$-arylalkyl group, where the alkyl part may bear one or more identical or different halogen, OH, $OR^2$, $SR^2NR^2_2$—, $PR^2_2$—, —$SiR^2_3$ or —$OSiR^2_3$ substituents and the aryl part may bear one or more identical or different halogen, $OR^2$, $SR^2NR^2_2$—, $NH_2$, —$N_2H_3$, $NO_2$, CN, $CO_2R^2$, CHO, $PR^2_2$—, —$SiR^2_3$ or —$OSiR^2_3$ substituents, a $C_2$–$C_{10}$-alkenyl group which may bear one or more identical or different halogen, OR, $OR^2$, $CO_2R^2$, $COR^2$, $SR^2$, $NR^2_2$—, $PR^2_2$—, —$SiR^2_3$ or —$OSiR^2_3$ substituents, a $C_2$–$C_{10}$-alkynyl group which may bear one or more identical or different halogen, OH, $OR^2$, $SR^2$, $NR^2_2$—, $PR^2_2$—, —$SiR^2_3$ or —$OSiR^2_3$ substituents, a $C_8$–$C_{12}$-arylalkenyl group which may bear one or more identical or different halogen, OH, $OR^2$, $SR^2$, $NR^2_2$—, $PR^2_2$—, —$SiR^2_3$ or —$OSiR^2_3$ substituents, or $R^3$ is a halogen atom or a $PR^2_2$, $B(OR^2)_2$, $SiR^2_3$ or $SnR^2_3$ group, where $R^2$ are identical or different and are each a $C_1$–$C_{20}$-hydrocarbon group, eg. a $C_1$–$C_{10}$-alkyl group or $C_6$–$C_{14}$-aryl group which may each bear one or more identical or different halogen, OH, $OR^2$, $SR^2NR^2_2$—, $PR^2_2$—, —$SiR^2_3$ or —$OSiR^2_3$ substituents, or two radicals $R^2$ may be joined to form a ring system, or $R^3$ is a $C_1$–$C_{20}$-heterocyclic group which is bound via a carbon atom and may in turn bear $C_1$–$C_{20}$-radicals or heteroatoms as substituents, $Y^1$, $Y^2$ and $Y^3$ are identical or different and are each a hydrogen atom or are as defined for X or $R^3$, and $Y^4$, $Y^5$ and $Y^6$ are identical or different and are each a hydrogen atom or are as defined for $R^3$.

In the process of the present invention, the indanones of the formula I or Ia are converted directly into the indanones of the formula II or IIa in one reaction step by reaction with the coupling component. In this reaction, no use is made of protective groups for the carbonyl function of the indanone of the formula I or Ia.

For the purposes of this application, the term "heteroatom" refers to any atom of the Periodic Table of the Elements with the exception of carbon and hydrogen. A heteroatom is preferably an atom of Group 14, 15 or 16 of the Periodic Table of the Elements with the exception of carbon. The term "heterocyclic group" refers to a heteroatom-containing cyclic group.

In the process of the present invention, particular preference is given to using indanones of the formula I or Ia in which X is chlorine, bromine, iodine, triflate, nonaflate, mesylate, ethylsulfonate, benzenesulfonate, tosylate, triisopropylbenzenesulfonate, formate, acetate, trifluoroacetate, nitrobenzoate, halogenated arylcarboxylates, in particular fluorinated benzoate, methyl carbonate, ethyl carbonate, benzyl carbonate, tert-butyl carbonate, dimethyl phosphonate, diethyl phosphonate, diphenyl phosphonate or diazonium, $R^1$ is a linear, branched or cyclic $C_1$–$C_8$-alkyl group which may bear one or more identical or different fluorine, chlorine, $OR^2$, $PR^2_2$—, $NR^2_2$—, —$SiR^2_3$ or —$OSiR^2_3$ substituents, a $C_6$–$C_{10}$-aryl group which may bear one or more identical or different fluorine, chlorine, $OR^2$, $SR^2$, $NR^2_2$—, $PR^2_2$—, —$SiR^2_3$ or —$OSiR^2_3$ substituents, a $C_7$–$C_{12}$-alkylaryl or arylalkyl group, where the alkyl part may bear one or more identical or different fluorine, chlorine, $OR^2$, $SR^2NR^2_2$—, $PR^2_2$—, —$SiR^2_3$ or —$OSiR^2_3$ substituents and the aryl part may bear one or more identical or different fluorine, chlorine, $OR^2$, $SR^2$, $NR^2_2$—, $PR^2_2$—, —$SiR^2_3$ or —$OSiR^2_3$ substituents, a $C_2$–$C_8$-alkenyl group or a $C_2$–$C_8$-alkynyl group which may each bear one or more identical or different fluorine, chlorine, $OR^2$ or $NR^2_2$ substituents, a $C_8$–$C_{12}$-arylalkenyl group which may bear one or more identical or different fluorine, chlorine, $OR^2$ or $NR^2_2$ substituents, or $R^1$ is an $OR^2$, $PR^2_2$, $NR^2_2$, —$SiR^2_3$ or —$OSiR^2_3$ group, where $R^2$ are identical or different and are each a $C_1$–$C_4$-alkyl group or $C_6$–$C_{10}$-aryl group, where the alkyl group may bear one or more identical or different fluorine, chlorine, $OR^2$, $SR^2$, $NR^2_2$—, $PR^2_2$—, —$SiR^2_3$ or —$OSiR^2_3$ substituents and the aryl group may bear one or more identical or different fluorine, chlorine, $OR^2$, $SR^2$, $NR^2_2$—, $PR^2_2$—, —$SiR^2_3$ or —$OSiR^2_3$ substituents, or $R^1$ is a $C_1$–$C_{20}$-heterocyclic group, with preferred heteroatoms being oxygen, nitrogen, sulfur, phosphorus and silicon, which may in turn bear $C_1$–$C_{20}$-radicals or heteroatoms as substituents, $R^3$ is a $C_1$–$C_{20}$-group such as a linear, branched or cyclic $C_{1-10}$-alkyl group which may bear one or more identical or different fluorine, $OR^2$, $NR^2_2$— or —$OSiR^2_3$ substituents, a $C_1$–$C_4$-aryl group which may bear fluorine, chlorine, $OR^2$, $SR^2$, $NR^2_2$, $NH_2$, $NO_2$, CN, $COR_2$ or $CO_2R_2$ substituents, a $C_7$–$C_{15}$-alkylaryl group or $C_7$–$C_{15}$-arylalkyl group, where the alkyl part may bear one or more identical or different fluorine, $OR^2$, $NR^2_2$— or $OSiR^2_3$ substituents, and the aryl part may bear fluorine, chlorine, $OR^2$, $SR^2$, $NR^2_2$—, $NH_2$, $NO_2$, CN, $COR_2$ or $CO^2R^2$ substituents, a $C_2$–$C_{10}$-alkenyl group which may bear one or more identical or different fluorine, $OR^2$, $CO^2R^2$, $COR^2$, $NR^2_2$— or $OSiR^2_3$ substituents, a $C_2$–$C_{10}$-alkynyl group which may bear one or more identical or different fluorine, $OR^2$, $NR^2_2$— or $OSiR^2_3$ substituents, a $C_8$–$C_{12}$-arylalkenyl group, a $PR^2_2$, $B(OR^2)_2$ or $SnR^2_3$ group, where $R^2$ are identical or different and are each a $C_1$–$C_4$-alkyl group or, $C_6$-aryl group, where the alkyl group may bear one or more identical or different fluorine, chlorine, $OR^2$ or $NR^2_2$ substituents and the aryl group may bear fluorine, chlorine, $OR^2$ or $NR^2_2$ substituents and, in addition, two radicals $R^2$ may be joined to one another to form a ring system, a $C_1$–$C_{14}$-heterocyclic group, where preferred heteroatoms are oxygen, nitrogen or sulfur and the group may in turn bear $C_1$–$C_6$-radicals or heteroatoms as substituents, $Y^1$, $Y^2$ and $Y^3$ are identical or different and are each a hydrogen atom or are as defined for $R^3$ or X and at least one of the radicals $Y^1$, $Y^2$ and $Y^3$, preferably $Y^3$, is a hydrogen atom, $Y^4$, $Y^5$ and $Y^6$ are identical or different and are each a hydrogen atom or are as defined for $R^3$ and at least one of the radicals $Y^4$, $Y^5$ and $Y^6$, preferably $Y^6$, is a hydrogen atom.

Very particular preference is given to indanones of the formula I or Ia in which X is chlorine, bromine, iodine, triflate, nonaflate, mesylate, tosylate or diazonium, $R^1$ is a linear, branched or cyclic $C_1$–$C_8$-alkyl group which may bear one or more identical or different fluorine, chlorine, $OR^2$ or $NR^2_2$ substituents, a phenyl group which may bear one or more identical or different fluorine, chlorine, $OR^2$ or $NR^2_2$ substituents, a $C_7$–$C_{12}$-alkylaryl or arylalkyl group, where the alkyl part may bear one or more identical or different fluorine, chlorine, $OR^2$ or $NR^2_2$ substituents and the aryl part may bear one or more identical or different fluorine, chlorine, $OR^2$ or $NR^2_2$ substituents, a $C_2$–$C_8$-alkenyl group or a $C_2$–$C_8$-alkynyl group which may each bear one or more identical or different fluorine, chlorine, $OR^2$ or $NR^2_2$ substituents, a $C_8$–$C_{12}$-arylalkenyl group which may bear one or more identical or different fluorine, chlorine, $OR^2$ or $NR^2_2$ substituents, or $R^1$ is an $OR^2$, $SiR^2_3$ or —$OSiR^2_3$ group, where $R^2$ are identical or different and are each a $C_{1-4}$-alkyl group or phenyl group, where the alkyl group may bear one or more identical or different fluorine, chlorine, $OR^2$ or $NR^2_2$ substituents and the aryl group may bear one or more identical or different fluorine, chlorine, $OR^2$ or $NR^2_2$ substituents, or $R^1$ is a $C_1$–$C_{16}$-heterocyclic group, where preferred heteroatoms are oxygen, nitrogen, sulfur and silicon and the group may in turn bear $C_1$–$C_{10}$-radicals or heteroatoms as substituents, $Y^1$, $Y^2$ or $Y^3$ are identical or different and are each a hydrogen atom, chlorine, bromine, iodine, triflate, nanoflate, mesylate, tosylate or diazonium, or $Y^1$, $Y^2$ or $Y^3$ are each a linear, branched or cyclic $C_1$–$C_8$-alkyl group which may bear one or more identical or different halogen, OH, $OR^2$, $SR^2NR^2_2$—, $PR^2_2$—, —$SiR^2_3$ or —$OSiR^2_3$ substituents, a $C_6$–$C_{14}$-aryl group which may bear one or more identical or different halogen, $OR^2$, $SR^2NR^2_2$—, $NH_2$, —$N_2H_3$, $NO_2$, CN, $CO_2R^2$, CHO, $COR^2$, $PR^2_2$—, —$SiR^2_3$ or —$OSiR^2_3$ substituents, a $C_7$–$C_{15}$-alkylaryl group or $C_7$–$C_{15}$-arylalkyl group, where the alkyl part may bear one or more identical or different halogen, OH, $OR^2$, $SR^2NR^2_2$—, $PR^2_2$—, —$SiR^2_3$ or —$OSiR^2_3$ substituents and the aryl part may bear one or more identical or different halogen, $OR^2$, $SR^2NR^2_2$—, $NH_2$, —$N_2H_3$, $NO_2$, CN, $CO_2R^2$, CHO, $PR^2_2$—, —$SiR^2_3$ or —$OSiR^2_3$ substituents, a $C_2$–$C_{10}$-alkenyl group which may bear one or more identical or different halogen, OH, $OR^2$, $SR^2$, $NR^2_2$—, $PR^2_2$—, —$SiR^2_3$ or —$OSiR^2_3$ substituents, a $C_2$–$C_8$-alkynyl group which may bear one or more identical or different halogen, OH, $OR^2$, $SR^2$, $NR^2_2$—, $PR^2_2$—, —$SiR^2_3$ or —$OSiR^2_3$ substituents, a $C_8$–$C_{12}$-arylalkenyl group which may bear one or more identical or different halogen, OH, $OR^2$, $SR^2$, $NR^2_2$—, $PR^2_2$—, —$SiR^2_3$ or —$OSiR^2_3$ substituents, or $Y^1$, $Y^2$ or $Y^3$ are each a halogen atom or an $NR^2_2$, $PR^2_2$, $B(OR^2)_2$, $SiR^2_3$ or $SnR^2_3$ group, where $R^2$ are identical or different and are each a $C_1$–$C_{20}$-hydrocarbon group, eg. a $C_1$–$C_{10}$-alkyl group or $C_6$–$C_{14}$-aryl group which may each bear one or more identical or different halogen, OH, $OR^2$, $SR^2$, $NR^2_2$—, $PR^2_2$—, —$SiR^2_3$ or —$OSiR^2_3$ substituents, or two radicals $R^2$ may be joined to form a ring system, or $Y^1$, $Y^2$ or $Y^3$ are each a $C_1$–$C_{20}$-heterocyclic group which is bound via a carbon atom and may in turn bear $C_1$–$C_{20}$-radicals or heteroatoms as substituents, and at least two of the radicals $Y^1$, $Y^2$ and $Y^3$ are each a hydrogen atom, preferably $Y^1$ and $Y^3$.

$R^3$ is a $C_1$–$C_4$-group such as a linear, branched or cyclic $C_1$–$C_8$-alkyl group which may bear one or more identical or different fluorine, $OR^{2a}$, $NR^{2a}_2$— or $OSiR^{2a}_3$ substituents, a $C_6$–$C_{14}$-aryl group which may bear fluorine, chlorine, $R^2$, $OR^{2a}$ or $NR^{2a}_2$ substituents, a $C_7$–$C_{10}$-alkylaryl group or $C_7$–$C_{10}$-arylalkyl group, where the alkyl part may bear one or more identical or different fluorine, $OR^{2a}$, $NR^{2a}_2$— or $OSiR^{2a}_3$ substituents and the aryl part may bear one or more identical or different fluorine, chlorine, $OR^{2a}$ or $NR^{2a}_2$ substituents, a $C_2$–$C_8$-alkenyl group which may bear one or more identical or different fluorine, $OR^{2a}$, $CO^2R^{2a}$ or $NR^{2a}_2$ substituents, a $C_2$–$C_8$-alkynyl group which may bear one or more identical or different fluorine, $OR^{2a}$ or $NR^{2a}_2$ substituents, a $C_8$–$C_{12}$-arylalkenyl group, a $PR^{2a}_2$, $B(OR^{2a})_2$ or $SnR^{2a}_3$ group, where $R^{2a}$ are identical or different and are each a linear or branched $C_1$–$C_4$-alkyl group which may bear one or more fluorine substituents, or a phenyl group which may bear one or more identical or different fluorine or $OR^{2a}$ substituents, and, in addition, two radicals $R^{2a}$ may be joined to one another to form a ring system, a $C_1$–$C_4$-heterocyclic group, where preferred heteroatoms are oxygen, nitrogen or sulfur and the group may in turn bear $C_1$–$C_4$-radicals or heteroatoms as substituents, and $Y^4$, $Y^5$ and $Y^6$ are identical or different and are each a hydrogen atom or $R^3$ and at least two of the radicals $Y^4$, $Y^5$ and $Y^6$ are hydrogen, preferably $Y^4$ and $Y^6$.

Illustrative examples of indanones of the formula I, which do not, however, restrict the scope of the invention, are:

2-methyl-7-chloro-1-indanone 2-methyl-7-bromo-1-indanone 2-methyl-7-iodo-1-indanone 2-methyl-7-trifluoroacetoxy-1-indanone 2-methyl-7-trifluoromethanesulfonoxy-1-indanone 2-methyl-7- methanesulfonoxy-1-indanone 2-methyl-7-ethanesulfonoxy-1-indanone 2-methyl-7-(p-toluenesulfonoxy)-1-indanone 2-methyl-7-benzenesulfonoxy-1-indanone 2-methyl-7-(2,4,6-triisopropylbenzenesulfonoxy)-1-indanone 2-methyl-7-pentafluorobenzenesulfonoxy-1-indanone 2-methyl-7-nonafluorobutanesulfonoxy-1-indanone 2-methyl-7-acetoxy-1-indanone 2-methyl-7-formyloxy-1-indanone 2-methyl-7-pentafluorobenzoyloxy-1-indanone 2-methyl-7-(p-nitrobenzoyloxy)-1-indanone 2-methyl-7-methoxycarbonyloxy-1-indanone 2-methyl-7-tert-butyloxycarbonyloxy-1-indanone 2-methyl-7-ethoxycarbonyloxy-1-indanone 2-methyl-7-benzyloxycarbonyloxy-1-indanone 2-methyl-7-dimethylphosphonoxy-1-indanone 2-methyl-7-diethylphosphonoxy-1-indanone 2-methyl-7-diphenylphosphonoxy-1-indanone 2-methyl-7-diazonium-1-indanone chloride 2-methyl-7-diazonium-1-indanone tetrafluoroborate 2-methyl-7-diazonium-1-indanone sulfate 2-methyl-4-vinyl-7-bromo-1-indanone 2-methyl-5-butyl-7-bromo-1-indanone 2-methyl-5-fluoro-7-bromo-1-indanone 2-methyl-4-isopropyl-7-bromo-1-indanone 2-methyl-5,7-dibromo-1-indanone 2-methyl-5,7-dichloro-1-indanone 2-methyl-6,7-dichloro-1-indanone 2-methyl-5-chloro-7-bromo-1-indanone 2-methyl-4-phenyl-7-diazonium-1-indanone chloride 2-methyl-4-cyclohexyl-7-diazonium-1-indanone tetrafluoroborate 2,5-dimethyl-7-chloro-1-indanone 2,4-dimethyl-7-bromo-1-indanone 2,6-dimethyl-7-chloro-1-indanone 2-methyl-5-butyl-7-chloro-1-indanone 2-methyl-5-isopropyl-7-trifluoromethanesulfonoxy-1-indanone 2-methyl-5-tert-butyl-7-methanesulfonoxy-1-indanone 2-methyl-5-phenyl-7-bromo-1-indanone 2-methyl-5-(3,5-dimethoxyphenyl)-7-iodo-1-indanone 2-methyl-5-benzyl-7-chloro-1-indanone 2-methyl-5-methoxy-7-chloro-1-indanone 2-methyl-5-phenoxy-7-chloro-1-indanone 2-methyl-6-methoxy-7-chloro-1-indanone 2-methyl-6-isopropoxy-7-bromo-1-indanone 2-methyl-6-trimethylsilyloxy-7-bromo-1-indanone 2-methyl-5-vinyl-7-(p-toluenesulfonoxy)-1-indanone 2-methyl-6-bromo-7-trifluoroacetoxy-1-indanone 2-methyl-6-phenyl-7-bromo-1-indanone 2-methyl-4-methoxy-7-chloro-1-indanone 2-methyl-4-diisopropylamino-7-chloro-1-indanone 2-trifluoromethyl-7-chloro-1-indanone 2-trifluoromethyl-7-bromo-1-indanone 2-trifluoromethyl-4-methyl-7-chloro-1-indanone 2-trifluoromethyl-5-isobutyl-7-trifluoromethanesulfonoxy-1-indanone 2-ethyl-7-chloro-1-indanone 2-ethyl-7-bromo-1-indanone 2-ethyl-7-diazonium-1-indanone tetrafluoroborate 2-ethyl-7-methanesulfonoxy-1-indanone 2-ethyl-4-trimethylsilyloxy-7-trifluoromethanesulfonoxy-1-indanone 2-ethyl-5-methyl-7-bromo-1-indanone 2-ethyl-4-benzyl-7-bromo-1-indanone 2-ethyl-7-diazonium-1-indanone tetrafluoroborate 2-n-propyl-7-chloro-1-indanone 2-n-propyl-7-bromo-1-indanone 2-n-propyl-5,7-dichloro-1-indanone 2-n-propyl-7-trifluoromethanesulfonoxy-1-indanone 2,6-diethyl-7-diazonium-1-indanone chloride 2-butyl-7-chloro-1-indanone 2-butyl-5-fluoro-7-chloro-1-indanone 2-butyl-5,7-dichloro-1-indanone 2-isopropyl-7-chloro-1-indanone 2-isopropyl-7-bromo-1-indanone 2-isopropyl-7-iodo-1-indanone 2-isopropyl-5-diphenylphosphino-7-nonafluorobutanesulfonoxy-1-indanone 2-phenyl-4-dimethylamino-7-bromo-1-indanone 2-phenyl-7-chloro-1-indanone 2-(2-pyridyl)-7-bromo-1-indanone 2-(2-furyl)-7-iodo-1-indanone 2-cyclohexyl-7-chloro-1-indanone 2-cyclohexyl-7-bromo-1-indanone 2-cyclohexyl-7-trifluoromethanesulfonoxy-1-indanone 2-isobutyl-7-chloro-1-indanone 2-isobutyl-7-bromo-1-indanone 2-tert-butyl-7-chloro-1-indanone 2-tert-butyl-7-iodo-1-indanone 2-benzyl-7-chloro-1-indanone 2-allyl-7-chloro-1-indanone 2-vinyl-7-trifluoromethanesulfonoxy-1-indanone 2-(2-trimethylsilylethyn-1-yl)-6-benzyl-7-chloroindanone 2-(hex-1-ynyl)-7-trifluoromethanesulfonoxy-1-indanone 2-trimethylsilyl-7-bromo-1-indanone 2-trimethylsilyloxy-7-bromo-1-indanone 2-dimethylamino-7-trifluoromethanesulfonoxy-1-indanone 2-N-pyrrolidino-7-chloro-1-indanone 2-diphenylphosphino-5-isopropyl-7-bromo-1-indanone 2-methoxy-6-allyl-7-chloro-1-indanone 2,6-dimethoxy-7-bromo-1-indanone 2-phenoxy-5-dimethylamino-7-trifluoromethanesulfonoxy-1-indanone 2-(2-methoxyethyl)-7-chloro-1-indanone 2-(3-chloropropyl)-7-chloro-1-indanone 2,4,5,6-tetramethyl-7-chloro-1-indanone 2-methyl-4-phenyl-5-methoxy-7-bromo-1-indanone 2-butyl-5-benzyl-6-bromo-7-trifluoromethanesulfonoxy-1-indanone 2-trimethylsilyloxy-4-methoxy-5-allyl-7-diazonium-1-indanone tetrafluoroborate 2-N-piperidino-4-fluoro-5,7-dibromo-1-indanone 2-isopropyl-4-cyclohexyl-5-methyl-7-trimethylstannyl-1-indanone 2,5-dimethoxy-4-bromo-6-trifluoromethyl-7-iodo-1-indanone 2-ethyl-4-dimethylamino-5-trimethylsilyl-7-chloroindanone 2-trifluoroethoxy-4-thiomethoxy-6-butyl-7-bromo-1-indanone 2-triethylsilyl-5,6-difluoro-7-methanesulfonoxy-1-indanone 2,5-diphenyl-7-bromo-1-indanone Illustrative examples of indanones of the formula Ia, which, however, do not restrict the scope of the invention, are:

2-methyl-4-chloro-1-indanone 2-methyl-4-bromo-1-indanone 2-methyl-4-iodo-1-indanone 2-methyl-4-trifluoroacetoxy-1-indanone 2-methyl-4-trifluoromethanesulfonoxy-1-indanone 2-methyl-4-methanesulfonoxy-1-indanone 2-methyl-4-ethanesulfonoxy-1-indanone 2-methyl-4-(p-toluenesulfonoxy)-1-indanone 2-methyl-4-benzenesulfonoxy-1-indanone 2-methyl-4-(2,4,6-triisopropylbenzenesulfonoxy)-1-indanone 2-methyl-4-pentafluorobenzenesulfonoxy-1-indanone 2-methyl-4-nonafluorobutanesulfonoxy-1-indanone 2-methyl-4-acetoxy-1-indanone 2-methyl-4-formyloxy-1-indanone 2-methyl-4-pentafluorobenzoyloxy-1-indanone 2-methyl-4-(p-nitrobenzoyloxy)-1-indanone 2-methyl-4-methoxycarbonyloxy-1-indanone 2-methyl-4-tert-butyloxycarbonyloxy-1-indanone 2-methyl-4-ethoxycarbonyloxy-1-indanone 2-methyl-4-benzyloxycarbonyloxy-1-indanone 2-methyl-4-dimethylphosphonoxy-1-indanone 2-methyl-4-diethylphosphonoxy-1-indanone 2-methyl-4-diphenylphosphonoxy-1-indanone 2-methyl-4-diazonium-1-indanone chloride 2-methyl-4-diazonium-1-indanone tetrafluoroborate 2-methyl-4-diazonium-1-indanone sulfate 2-methyl-7-vinyl-4-bromo-1-indanone 2-methyl-5-butyl-4-bromo-1-indanone 2-methyl-6-fluoro-4-bromo-1-indanone 2-methyl-7-isopropyl-4-bromo-1-indanone 2-methyl-4,7-dibromo-1-indanone 2-methyl-5,4-dichloro-1-indanone 2-methyl-6,4-dichloro-1-indanone 2-methyl- 4,7-dichloro-1-indanone 2-methyl-5-chloro-4-bromo-1-indanone 2-methyl-7-phenyl-4-diazonium-1-indanone chloride 2-methyl-7-cyclohexyl-4-diazonium-1-indanone tetrafluoroborate 2,5-dimethyl-4-chloro-1-indanone 2,7-dimethyl-4-bromo-1-indanone 2,6-dimethyl-4-chloro-1-indanone 2-methyl-5-butyl-4-chloro-1-indanone 2-methyl-5-isopropyl-4-trifluoromethanesulfonoxy-1-indanone 2-methyl-5-tert-butyl-4-methanesulfonoxy-1-indanone 2-methyl-5-phenyl-4-bromo-1-indanone 2-methyl-5-(3,5-dimethoxyphenyl)-4-iodo-1-indanone 2-methyl-6-benzyl-4-chloro-1-indanone 2-methyl-6-methoxy-4-chloro-1-indanone 2-methyl-5-phenoxy-4-chloro-1-indanone 2-methyl-6-methoxy-4-chloro-1-indanone 2-methyl-6-isopropoxy-4-bromo-1-indanone 2-methyl-6-trimethylsilyloxy-4-bromo-1-indanone 2-methyl-5-vinyl-4-(p-toluenesulfonoxy)-1-indanone 2-methyl-6-bromo-4-trifluoroacetoxy-1-indanone 2-methyl-6-phenyl-4-bromo-1-indanone 2-methyl-7-methoxy-4-chloro-1-indanone 2-methyl-7-diisopropylamino-4-chloro-1-indanone 2-trifluoromethyl-4-chloro-1-indanone 2-trifluoromethyl-4-bromo-1-indanone 2-trifluoromethyl-4-methyl-4-chloro-1-indanone 2-trifluoromethyl-5-isobutyl-4-trifluoromethanesulfonoxy-1-indanone 2-ethyl-4-chloro-1-indanone 2-ethyl-4-bromo-1-indanone 2-ethyl-4-diazonium-1-indanone tetrafluoroborate 2-ethyl-4-methanesulfonoxy-1-indanone 2-ethyl-5-trimethylsilyloxy-4-trifluoromethanesulfonoxy-1-indanone 2-ethyl-5-methyl-4-bromo-1-indanone 2-ethyl-7-benzyl-4-bromo-1-indanone 2-ethyl-4-diazonium-1-indanone tetrafluoroborate 2,6-diethyl-4-diazonium-1-indanone chloride 2-n-propyl-4-chloro-1-indanone 2-n-propyl-4-bromo-1-indanone 2-n-propyl-4,6-dichloro-1-indanone 2-n-propyl-7-trifluoromethanesulfonoxy-1-indanone 2-butyl-4-chloro-1-indanone 2-butyl-4-bromo-1-indanone 2-butyl-5-fluoro-4-chloro-1-indanone 2-butyl-4,5-dichloro-1-indanone 2-isopropyl-4-chloro-1-indanone 2-isopropyl-4-bromo-1-indanone 2-isopropyl-4-iodo-1-indanone 2-isopropyl-5-diphenylphosphino-4-nonafluorobutanesulfonoxy-1-indanone 2-phenyl-7-dimethylamino-4-bromo-1-indanone 2-phenyl-4-chloro-1-indanone 2-(2-pyridyl)-4-bromo-1-indanone 2-(2-furyl)-4-iodo-1-indanone 2-cyclohexyl-4-chloro-1-indanone 2-cyclohexyl-4-bromo-1-indanone 2-cyclohexyl-4-trifluoromethanesulfonoxy-1-indanone 2-isobutyl-4-chloro-1-indanone 2-isobutyl-4-bromo-1-indanone 2-tert-butyl-4-chloro-1-indanone 2-tert-butyl-4-iodo-1-indanone 2-benzyl-4-chloro-1-indanone 2-allyl-4-chloro-1-indanone 2-vinyl-4-trifluoromethanesulfonoxy-1-indanone 2-(2-trimethylsilylethyn-1-yl)-6-benzyl-4-chloroindanone 2-(hex-1-ynyl)-4-trifluoromethanesulfonoxy-1-indanone 2-trimethylsilyl-4-bromo-1-indanone 2-trimethylsilyloxy-4-bromo-1-indanone 2-dimethylamino-4-trifluoromethanesulfonoxy-1-indanone 2-N-pyrrolidino-4-chloro-1-indanone 2-diphenylphosphino-5-isopropyl-4-bromo-1-indanone 2-methoxy-6-allyl-4-chloro-1-indanone 2,6-dimethoxy-4-bromo-1-indanone 2-phenoxy-5-dimethylamino-4-trifluoromethanesulfonoxy-1-indanone 2-(2-methoxyethyl)-4-chloro-1-indanone 2-(3-chloropropyl)-4-chloro-1-indanone 2,5,6,7-tetramethyl-4-chloro-1-indanone 2-methyl-7-phenyl-5-methoxy-4-bromo-1-indanone 2-butyl-5-benzyl-6-bromo-4-trifluoromethanesulfonoxy-1-indanone 2-trimethylsilyloxy-7-methoxy-5-allyl-4-diazonium-1-indanone tetrafluoroborate 2-N-piperidino-7-fluoro-5,4-dibromo-1-indanone 2-isopropyl-7-cyclohexyl-5-methyl-4-trimethylstannyl-1-indanone 2,5-dimethoxy-7-bromo-6-trifluoromethyl-4-iodo-1-indanone 2-ethyl-7-dimethylamino-5-trimethylsilyl-4-chloroindanone 2-trifluoroethoxy-7-thiomethoxy-6-butyl-4-bromo-1-indanone 2-triethylsilyl-5,6-difluoro-4-methanesulfonoxy-1-indanone 2,5-diphenyl-4-bromo-1-indanone Illustrative examples of indanones of the formula II, which, however, do not restrict the scope of the invention, are:

2-methyl-7-phenyl-1-indanone 2-methyl-7-(1-naphthyl)-1-indanone 2-methyl-6-(2-naphthyl)-1-indanone 2-methyl-7-(2-methyl-1-naphthyl)-1-indanone 2-methyl-7-(4-methyl-1-naphthyl)-1-indanone 2-methyl-7-(4-methoxy-1-naphthyl)-1-indanone 2-methyl-7-(6-methoxy-2-naphthyl)-1-indanone 2-methyl-7-(4-methylphenyl)-1-indanone 2-methyl-7-(3-methylphenyl)-1-indanone 2-methyl-7-(2-methylphenyl-1-indanone 2-methyl-7-(3,5-dimethylphenyl)-1-indanone 2-methyl-7-(2,3-dimethylphenyl)-1-indanone 2-methyl-7-(2,4-dimethylphenyl)-1-indanone 2-methyl-7-(2,5-dimethylphenyl)-1-indanone 2-methyl-7-(3-butylphenyl)-1-indanone 2-methyl-7-(4-tert-butylphenyl)-1-indanone 2-methyl-7-(4-ethylphenyl)-1-indanone 2-methyl-7-(4-isopropylphenyl)-1-indanone 2-methyl-7-(3,5-di-tert-butylphenyl)-1-indanone 2-methyl-7-mesityl-1-indanone 2-methyl-7-(4-biphenyl)-1-indanone 2-methyl-7-(3-biphenyl)-1-indanone 2-methyl-7-(2-biphenyl)-1-indanone 2-methyl-7-(3,5-diphenylphenyl)-1-indanone 2-methyl-7-(4-styryl)-1-indanone 2-methyl-7-(3-styryl)-1-indanone 2-methyl-7-(2-styryl)-1-indanone 2-methyl-7-(9-anthracenyl)-1-indanone 2-methyl-7-(9-phenanthrenyl)-1-indanone 2-methyl-7-(2-hydroxyphenyl)-1-indanone 2-methyl-7-(4-hydroxyphenyl)-1-indanone 2-methyl-7-(3-hydroxyphenyl)-1-indanone 2-methyl-7-(2,4-dihydroxyphenyl)-1-indanone 2-methyl-7-(3,5-dihydroxyphenyl)-1-indanone 2-methyl-7-(4-methoxyphenyl)-1-indanone 2-methyl-7-(3-methoxyphenyl)-1-indanone 2-methyl-7-(2-methoxyphenyl)-1-indanone 2-methyl-7-(2,4-dimethoxyphenyl)-1-indanone 2-methyl-7-(3,5-dimethoxyphenyl)-1-indanone 2-methyl-7-(3,4,5-trimethoxyphenyl)-1-indanone 2-methyl-7-(4-phenoxyphenyl)-1-indanone 2-methyl-7-(3,4-methylenedioxyphenyl)-1-indanone 2-methyl-7-(4-thioanisyl)-1-indanone 2-methyl-7-(3-thioanisyl)-1-indanone 2-methyl-7-(4-nitrophenyl)-1-indanone 2-methyl-7-(3-nitrophenyl)-1-indanone 2-methyl-7-(2-nitrophenyl)-1-indanone 2-methyl-7-(4-methyl-3-nitrophenyl)-1-indanone 2-methyl-7-(4-methoxycarbonylphenyl)-1-indanone 2-methyl-7-(3-methoxycarbonylphenyl)-1-indanone 2-methyl-7-(2-methoxycarbonylphenyl)-1-indanone 2-methyl-7-(2-carboxyphenyl)-1-indanone 2-methyl-7-(2-carboxyphenyl)-1-indanone 2-methyl-7-(4-formylphenyl)-1-indanone 2-methyl-7-(4-acetylphenyl)-1-indanone 2-methyl-7-(4-pivaloylphenyl)-1-indanone 2-methyl-7-(4-aminophenyl)-1-indanone 2-methyl-7-(3-aminophenyl)-1-indanone 2-methyl-7-(2- aminophenyl)-1-indanone 2-methyl-7-(4-dimethylaminophenyl)-1-indanone 2-methyl-7-(3-dimethylaminophenyl)-1-indanone 2-methyl-7-(4-(1-pyrrolidino)phenyl)-1-indanone 2-methyl-7-(4-hydrazinophenyl)-1-indanone 2-methyl-7-(4-cyanophenyl)-1-indanone 2-methyl-7-(3-cyanophenyl)-1-indanone 2-methyl-7-(2-cyanophenyl)-1-indanone 2-methyl-7-(4-trifluoromethoxyphenyl)-1-indanone 2-methyl-7-(4-fluorophenyl)-1-indanone 2-methyl-7-(4-bromophenyl)-1-indanone 2-methyl-7-(2,4-difluorophenyl)-1-indanone 2-methyl-7-(4-chlorophenyl)-1-indanone 2-methyl-7-(3,5-dichlorophenyl)-1-indanone 2-methyl-7-(4-trifluoromethylphenyl)-1-indanone 2-methyl-7-(3-trifluoromethylphenyl)-1-indanone 2-methyl-7-(3,5-bis(trifluoromethyl)phenyl)-1-indanone 2-methyl-7-(2,4-bis(trifluoromethyl)phenyl)-1-indanone 2-methyl-7-(2-furyl)-1-indanone 2-methyl-7-(3-furyl)-1-indanone 2-methyl-7-(5-methyl-2-furyl)-1-indanone 2-methyl-7-(benzofuryl)-1-indanone 2-methyl-7-(2-thiophenyl)-1-indanone 2-methyl-7-(5-methyl-2-thiophenyl)-1-indanone 2-methyl-7-(3-thiophenyl)-1-indanone 2-methyl-7-(5-isobutyl-2-thiophenyl)-1-indanone 2-methyl-7-(benzothiophenyl)-1-indanone 2-methyl-7-(N-methyl-2-pyrrolyl)-1-indanone 2-methyl-7-(N-methyl-3-pyrrolyl)-1-indanone 2-methyl-7-(2-pyridyl)-1-indanone 2-methyl-7-(3-pyridyl)-1-indanone 2-methyl-7-(4-pyridyl)-1-indanone 2-methyl-7-(2-pyrimidyl)-1-indanone 2-methyl-7-(2-quinolyl)-1-indanone 2-methyl-7-(3-quinolyl)-1-indanone 2-methyl-7-(4-isoquinolyl)-1-indanone 2-methyl-7-(2-thiazolyl)-1-indanone 2-methyl-7-(2-benzothiazolyl)-1-indanone 2-methyl-7-(2-N-methylimidazolyl)-1-indanone 2-methyl-7-(2-N-methylbenzoimidazolyl)-1-indanone 2-methyl-7-(2-oxazolyl)-1-indanone 2-methyl-7-(N-methyltriazolyl)-1-indanone 2-methyl-7-butyl-1-indanone 2-methyl-7-cyclohexyl-1-indanone 2-methyl-7-isopropyl-1-indanone 2-methyl-7-benzyl-1-indanone 2-methyl-7-(hex-1-en-6-yl)-1-indanone 2-methyl-7-(hex-1-en-1-yl)-1-indanone 2-methyl-7-vinyl-1-indanone 2-methyl-7-(2-trimethylsilylethen-1-yl)-1-indanone 2-methyl-7-(2-phenylethyn-1-yl)-1-indanone 2-methyl-7-(2-tert-butylethyn-1-yl)-1-indanone 2-methyl-7-allyl-1-indanone 2-methyl-7-(2-trimethylsilylethyn-1-yl)-1-indanone 2-methyl-7-(2-phenylethen-1-yl)-1-indanone 2-methyl-7-trimethylstannyl-1-indanone 2-methyl-7-tributylstannyl-1-indanone 2-methyl-7-triphenylstannyl-1-indanone 2-methyl-7-(boronic acid pinacol ester)-1-indanone 2-methyl-7-(boronic acid trimethylene glycol ester)-1-indanone 2-methyl-7-(B-catecholborane)-1-indanone 2-methyl-7-diphenylphosphino-1-indanone 2-methyl-7-dibutylphosphino-1-indanone 2-methyl-7-(methoxyphenylmethylphosphino)-1-indanone 2-ethyl-7-phenyl-1-indanone 2-ethyl-7-(4-tolyl)-1-indanone 2-ethyl-7-naphthyl-1-indanone 2-ethyl-7-(2-furyl)-1-indanone 2-ethyl-7-cyclohexyl-1-indanone 2-ethyl-7-(4-tert-butylphenyl)-1-indanone 2-n-propyl-7-phenyl-1-indanone 2-n-propyl-7-naphthyl-1-indanone 2-n-propyl-7-(4-tert-butylphenyl)-1-indanone 2-n-propyl-7-(4-methylphenyl)-1-indanone 2-n-butyl-7-phenyl-1-indanone 2-n-butyl-7-naphthyl-1-indanone 2-n-butyl-7-(4-tert-butylphenyl)-1-indanone 2-n-butyl-7-(4-methylphenyl)-1-indanone 2-isopropyl-7-(2-pyrridyl)-1-indanone 2-isopropyl-7-phenyl-1-indanone 2-isopropyl-7-naphthyl-1-indanone 2-isobutyl-7-phenyl-1-indanone 2-isobutyl-7-naphthyl-1-indanone 2-cyclohexyl-7-phenyl-1-indanone 2-trifluoromethyl-7-phenyl-1-indanone 2-trifluoromethyl-7-(4-tolyl)-1-indanone 2-trifluoromethyl-7-naphthyl-1-indanone 2-trifluoromethyl-7-(4-methoxyphenyl)-1-indanone 2-trifluoromethyl-7-(3,5-bis(trifluoromethyl)phenyl)-1-indanone 2,4-dimethyl-7-phenyl-1-indanone 2-methyl-4-methoxy-7-phenyl-1-indanone 2,6-dimethyl-7-phenyl-1-indanone 2,5-dimethyl-7-phenyl-1-indanone 2,5-dimethyl-7-p-tolyl-1-indanone 2,5-dimethyl-7-(2-thiophenyl)-1-indanone 2,4-methyl-7-naphthyl-1-indanone 2-methyl-5-phenyl-7-naphthyl-1-indanone 2-methyl-5,7-diphenyl-1-indanone 2-methyl-7-(4-fluorophenyl)-1-indanone 2-methyl-5-diphenylphosphino-7-(4-nitrophenyl)-1-indanone 2-methyl-5-chloro-7-phenyl-1-indanone 2,6-dimethyl-7-(4-methoxyphenyl)-1-indanone 2-ethyl-4-methyl-7-(3,5-bis(trifluoromethyl)phenyl)-1-indanone 2-ethyl-5-vinyl-7-(2-furyl)-1-indanone 2-isopropyl-5-trifluoromethyl-7-phenyl-1-indanone 2-cyclohexyl-5-methyl-7-(2-pyridyl)-1-indanone 2-trifluoromethyl-4-butyl-7-naphthyl-1-indanone 2,5-trifluoromethyl-7-butyl-1-indanone 2-trimethylsilyl-5-isopropyl-7-(boronic acid pinacol ester)-1-indanone 2-dimethylamino-6-cyclohexyl-7-trimethylstannyl-1-indanone 2,4,5,6-tetramethyl-7-phenyl-1-indanone 2-methyl-4-phenyl-5-methoxy-7-naphthyl-1-indanone 2-butyl-5-benzyl-6-bromo-7-(4-methoxyphenyl)-1-indanone 2-trimethylsilyloxy-4-methoxy-5-allyl-7-(2-pyridyl)-1-indanone 2-N-piperidino-4-fluoro-5,7-diphenyl-1-indanone 2-isopropyl-4-cyclohexyl-5-methyl-7-trimethylstannyl-1-indanone 2,5-dimethoxy-4-bromo-6-trifluoromethyl-7-furyl-1-indanone 2-ethyl-5-trimethylsilyl-7-(2-tert-butylethyn-1-yl)-1-indanone 2-trifluoroethoxy-4-thiomethoxy-6-butyl-7-vinyl-1-indanone 2-triethylsilyl-5,6-difluoro-7-(3-cyanophenyl)-1-indanone 2,5-diphenyl-7-fluoro-1-indanone Illustrative examples of indanones of the formula IIa, which, however, do not restrict the scope of the invention, are:

2-methyl-4-phenyl-1-indanone 2-methyl-4-(1-naphthyl)-1-indanone 2-methyl-4-(2-naphthyl)-1-indanone 2-methyl-4-(2-methyl-1-naphthyl)-1-indanone 2-methyl-4-(4-methyl-1-naphthyl)-1-indanone 2-methyl-4-(4-methoxy-1-naphthyl)-1-indanone 2-methyl-4-(6-methoxy-2-naphthyl)-1-indanone 2-methyl-4-(4-methylphenyl)-1-indanone 2-methyl-4-(3-methylphenyl)-1-indanone 2-methyl-4-(2-methylphenyl)-1-indanone 2-methyl-4-(3,5-dimethylphenyl)-1-indanone 2-methyl-4-(2,3-dimethylphenyl)-1-indanone 2-methyl-4-(2,4-dimethylphenyl)-1-indanone 2-methyl-4-(2,5-dimethylphenyl)-1-indanone 2-methyl-4-(3-butylphenyl)-1-indanone 2-methyl-4-(4-tert-butylphenyl)-1-indanone 2-methyl-4-(3,5-di-tert-butylphenyl)-1-indanone 2-methyl-4-mesityl-1-indanone 2-methyl-4-(4-biphenyl)-1-indanone 2-methyl-4-(3-biphenyl)-1-indanone 2-methyl-4-(2-biphenyl)-1-indanone 2-methyl-4-(3,5-diphenylphenyl)-1-indanone 2-methyl-4-(4-styryl)-1-indanone 2-methyl-4-(3-styryl)-1-indanone 2-methyl-4-(2-styryl)-1-indanone 2-methyl-4-(9-anthracenyl-1-indanone 2-methyl-4-(9-phenanthrenyl)-1-indanone 2-methyl-4-(2-hydroxyphenyl)-1-indanone 2-methyl- 4-(4-hydroxyphenyl)-1-indanone 2-methyl-4-(3-hydroxyphenyl)-1-indanone 2-methyl-4-(2,4-dihydroxyphenyl)-1-indanone 2-methyl-4-(3,5-dihydroxyphenyl)-1-indanone 2-methyl-4-(4-methoxyphenyl)-1-indanone 2-methyl-4-(3-methoxyphenyl)-1-indanone 2-methyl-4-(2-methoxyphenyl)-1-indanone 2-methyl-4-(2,4-dimethoxyphenyl)-1-indanone 2-methyl-4-(3,5-dimethoxyphenyl)-1-indanone 2-methyl-4-(3,4,5-trimethoxyphenyl)-1-indanone 2-methyl-4-(4-phenoxyphenyl)-1-indanone 2-methyl-4-(3,4-methylenedioxyphenyl)-1-indanone 2-methyl-4-(4-thioanisyl)-1-indanone 2-methyl-4-(3-thioanisyl)-1-indanone 2-methyl-4-(4-nitrophenyl)-1-indanone 2-methyl-4-(3-nitrophenyl)-1-indanone 2-methyl-4-(2-nitrophenyl)-1-indanone 2-methyl-4-(4-methyl-3-nitrophenyl)-1-indanone 2-methyl-4-(4-methoxycarbonylphenyl)-1-indanone 2-methyl-4-(3-methoxycarbonylphenyl)-1-indanone 2-methyl-4-(2-methoxycarbonylphenyl)-1-indanone 2-methyl-4-(4-carboxylphenyl)-1-indanone 2-methyl-4-(2-carboxylphenyl)-1-indanone 2-methyl-4-(4-formylphenyl)-1-indanone 2-methyl-4-(4-acetylphenyl)-1-indanone 2-methyl-4-(4-pivaloylphenyl)-1-indanone 2-methyl-4-(4-aminophenyl)-1-indanone 2-methyl-4-(3-aminophenyl)-1-indanone 2-methyl-4-(2-aminophenyl)-1-indanone 2-methyl-4-(4-dimethylaminophenyl)-1-indanone 2-methyl-4-(3-dimethylaminophenyl)-1-indanone 2-methyl-4-(4-(1-pyrrolidino)phenyl)-1-indanone 2-methyl-4-(4-hydrazinophenyl)-1-indanone 2-methyl-4-(4-cyanophenyl)-1-indanone 2-methyl-4-(3-cyanophenyl)-1-indanone 2-methyl-4-(2-cyanophenyl)-1-indanone 2-methyl-4-(4-trifluoromethoxyphenyl)-1-indanone 2-methyl-4-(4-fluorophenyl)-1-indanone 2-methyl-4-(4-bromophenyl)-1-indanone 2-methyl-4-(2,4-difluorophenyl)-1-indanone 2-methyl-4-(4-chlorophenyl)-1-indanone 2-methyl-4-(3,5-dichlorophenyl)-1-indanone 2-methyl-4-(4-trifluoromethylphenyl)-1-indanone 2-methyl-4-(3-trifluoromethylphenyl)-1-indanone 2-methyl-4-(3,5-bis(trifluoromethyl)phenyl)-1-indanone 2-methyl-4-(2,4-bis(trifluoromethyl)phenyl)-1-indanone 2-methyl-4-(2-furyl)-1-indanone 2-methyl-4-(3-furyl)-1-indanone 2-methyl-4-(5-methyl-2-furyl)-1-indanone 2-methyl-4-(benzofuryl)-1-indanone 2-methyl-4-(2-thiophenyl)-1-indanone 2-methyl-4-(5-methyl-2-thiophenyl)-1-indanone 2-methyl-4-(3-thiophenyl)-1-indanone 2-methyl-4-(5-isobutyl-2-thiophenyl)-1-indanone 2-methyl-4-(benzothiophenyl)-1-indanone 2-methyl-4-(N-methyl-2-pyrrolyl)-1-indanone 2-methyl-4-(N-methyl-3-pyrrolyl)-1-indanone 2-methyl-4-(2-pyridyl)-1-indanone 2-methyl-4-(3-pyridyl)-1-indanone 2-methyl-4-(4-pyridyl)-1-indanone 2-methyl-4-(2-pyrimidyl)-1-indanone 2-methyl-4-(2-quinolyl)-1-indanone 2-methyl-4-(3-quinolyl)-1-indanone 2-methyl-4-(4-isoquinolyl)-1-indanone 2-methyl-4-(2-thiazolyl)-1-indanone 2-methyl-4-(2-benzothioazolyl)-1-indanone 2-methyl-4-(2-N-methylimidazolyl)-1-indanone 2-methyl-4-(2-N-methylbenzoimidazolyl)-1-indanone 2-methyl-4-(2-oxazolyl)-1-indanone 2-methyl-4-(N-methyltriazolyl)-1-indanone 2-methyl-4-butyl-1-indanone 2-methyl-4-cyclohexyl-1-indanone 2-methyl-4-isopropyl-1-indanone 2-methyl-4-benzyl-1-indanone 2-methyl-4-(hex-1-en-6-yl)-1-indanone 2-methyl-4-(hex-1-en-1-yl)-1-indanone 2-methyl-4-vinyl-1-indanone 2-methyl-4-(2-trimethylsilylethen-1-yl)-1-indanone 2-methyl-4-(2-phenylethyn-1-yl)-1-indanone 2-methyl-4-(2-tert-butylethyn-1-yl)-1-indanone 2-methyl-4-allyl-1-indanone 2-methyl-4-(2-trimethylsilylethyn-1-yl)-1-indanone 2-methyl-4-(2-phenylethen-1-yl)-1-indanone 2-methyl-4-trimethylstannyl-1-indanone 2-methyl-4-tributylstannyl-1-indanone 2-methyl-4-triphenylstannyl-1-indanone 2-methyl-4-(boronic acid pinacol ester)-1-indanone 2-methyl-4-(boronic acid trimethylene glycol ester)-1-indanone 2-methyl-4-(B-catecholborane)-1-indanone 2-methyl-4-diphenylphosphino-1-indanone 2-methyl-4-dibutylphosphino-1-indanone 2-methyl-4-(methoxyphenyl-methyl-phosphino)-1-indanone 2-ethyl-4-phenyl-1-indanone 2-ethyl-4-(4-tolyl)-1-indanone 2-ethyl-4-naphthyl-1-indanone 2-ethyl-4-(2-furyl)-1-indanone 2-ethyl-4-cyclohexyl-1-indanone 2-ethyl-4-butyl-1-indanone 2-n-propyl-4-phenyl-1-indanone 2-n-propyl-4-naphthyl-1-indanone 2-n-propyl-7-(4-tert-butylphenyl)-1-indanone 2-n-propyl-7-(4-methylphenyl)-1-indanone 2-n-butyl-7-phenyl-1-indanone 2-n-butyl-7-naphthyl-1-indanone 2-n-butyl-7-(4-tert-butylphenyl)-1-indanone 2-n-butyl-7-(4-methylphenyl)-1-indanone 2-isopropyl-4-(2-pyrridyl)-1-indanone 2-isopropyl-4-phenyl-1-indanone 2-isopropyl-4-naphthyl-1-indanone 2-isobutyl-4-phenyl-1-indanone 2-isobutyl-4-naphthyl-1-indanone 2-cyclohexyl-4-phenyl-1-indanone 2-trifluoromethyl-4-phenyl-1-indanone 2-trifluoromethyl-4-(4-tolyl)-1-indanone 2-trifluoromethyl-4-naphthyl-1-indanone 2-trifluoromethyl-4-(4-methoxyphenyl)-1-indanone 2-trifluoromethyl-4-(3,5-bis(trifluoromethyl)phenyl)-1-indanone 2,7-dimethyl-4-phenyl-1-indanone 2-methyl-7-methoxy-4-phenyl-1-indanone 2,6-dimethyl-4-phenyl-1-indanone 2,5-dimethyl-4-phenyl-1-indanone 2,5-dimethyl-4-p-tolyl-1-indanone 2,5-dimethyl-4-(2-thiophenyl)-1-indanone 2,7-methyl-4-naphthyl-1-indanone 2-methyl-5-phenyl-4-naphthyl-1-indanone 2-methyl-5,4-diphenyl-1-indanone 2-methyl-4-(4-fluorophenyl)-1-indanone 2-methyl-5-diphenylphosphino-4-(4-nitrophenyl)-1-indanone 2-methyl-5-chloro-4-phenyl-1-indanone 2,6-dimethyl-4-(4-methoxyphenyl)-1-indanone 2-ethyl-7-methyl-4-(3,5-bis(trifluoromethyl)phenyl)-1-indanone 2-ethyl-5-vinyl-4-(2-furyl)-1-indanone 2-isopropyl-5-trifluoromethyl-4-phenyl-1-indanone 2-cyclohexyl-5-methyl-4-(2-pyridyl)-1-indanone 2-trifluoromethyl-7-butyl-4-naphthyl-1-indanone 2,5-trifluoromethyl-4-butyl-1-indanone 2-trimethylsilyl-5-isopropyl-4-(boronic acid pinacol ester)-1-indanone 2-dimethylamino-6-cyclohexyl-4-trimethylstannyl-1-indanone 2,5,6,7-tetramethyl-4-phenyl-1-indanone 2-methyl-7-phenyl-5-methoxy-4-naphthyl-1-indanone 2-butyl-5-benzyl-6-bromo-4-(4-methoxyphenyl)-1-indanone 2-trimethylsilyloxy-7-methoxy-5-allyl-4-(2-pyridyl)-1-indanone 2-N-piperidino-7-fluoro-5,4-diphenyl-1-indanone 2-isopropyl-7-cyclohexyl-5-methyl-4-trimethylstannyl-1-indanone 2,5-dimethoxy-7-bromo-6-trifluoromethyl-4-furyl-1-indanone 2-trifluoroethoxy-7-thiomethoxy-6-butyl-4-vinyl-1-indanone 2-triethylsilyl-5,6-difluoro-4-(3-cyanophenyl)-1-indanone 2,5-diphenyl-7-fluoro-1-indanone In the process of the present invention, at least one indanone of the formula I or Ia is reacted with at least one coupling component, forming the indanones of the formulae II and IIa. In this reaction, the coupling component serves to introduce the radical $R^3$. It is also possible for the coupling component to convert one or more of the radicals $Y^1$, $Y^2$ and $Y^3$ which are as defined for X into radicals $Y^4$, $Y^5$ and $Y^6$ which are as defined for $R^3$.

The coupling components are preferably compounds containing elements of Groups 13–17 of the Periodic Table of the Elements. The coupling components are preferably compounds containing boron, carbon, silicon, germanium, tin, phosphorus or fluorine. The coupling components are particularly preferably compounds containing boron, carbon, silicon, tin or phosphorus.

Preferred boron-containing coupling components are boronic acids and boronic esters, for example of the type

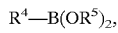

where $R^4$ is a $C_1$–$C_{40}$-group such as a linear, branched or cyclic $C_1$–$C_{20}$-alkyl group which may bear one or more identical or different halogen, OH, $OR^2$, $SR^2$, $NR^2_2$—, $PR^2_2$—, —$SiR^2_3$ or —$OSiR^2_3$ substituents, a $C_6$–$C_{22}$-aryl group which may bear one or more identical or different halogen, $OR^2$, $SR^2$, $NR^2_2$—, $NH_2$, —$N_2H_3$, $NO_2$, CN, $CO_2R^2$, $COR^2_4$, CHO, $PR^2_2$—, —$SiR^2_3$ or —$OSiR^2_3$ substituents, a $C_7$–$C_{15}$-alkylaryl group or $C_7$–$C_{15}$-arylalkyl group, where the alkyl group may bear one or more identical or different halogen, OH, $OR^2$, $SR^2$, $NR^2_2$—, $PR^2_2$—, —$SiR^2_3$ or —$OSiR^2_3$ substituents and the aryl group may bear one or more identical or different halogen, $OR^2$, $SR^2$, $NR^2_2$—, $NH_2$, —$N_2H_3$, $NO_2$, CN, $CO_2R^2$, $COR^2$, CHO, $PR^2_2$—, —$SiR^2_3$ or —$OSiR^2_3$ substituents, a $C_2$–$C_{10}$-alkenyl group which may bear one or more identical or different halogen, OH, $OR^2$, $SR^2$, $NR^2_2$—, $PR^2_2$—, —$SiR^2_3$ or —$OSiR^2_3$ substituents, a $C_2$–$C_{10}$-alkynyl group which may bear one or more identical or different halogen, OH, $OR^2$, $SR^2$, $NR^2_2$—, $PR^2_2$—, —$SiR^2_3$ or —$OSiR^2_3$ substituents, a $C_8$–$C_{12}$-arylalkenyl group which may bear one or more identical or different halogen, OH, $OR^2$, $SR^2$, $NR^2_2$—, $PR^2_2$—, —$SiR^2_3$ or —$OSiR^2_3$ substituents, or $R^4$ is a $C_1$–$C_{20}$-heterocyclic group which may in turn bear $C_1$–$C_{20}$-radicals or heteroatoms as substituents, and $R^5$ are identical or different and may each be a hydrogen atom, a linear, branched or cyclic $C_1$–$C_{40}$-group, for example a $C_{1-20}$-alkyl group or a $C_6$–$C_{14}$-aryl group, or form a ring system. Also preferred are condensation products of the abovementioned boronic acids and boronic esters.

Preferred boron-containing coupling components are, furthermore, boranes, for example of the type $R^6$—$B(R^7)_2$, where $R^6$ is a linear, branched or cyclic $C_1$–$C_{20}$-alkyl group or a $C_6$–$C_{14}$-aryl group, which may each bear one or more identical or different halogen, $OR^2$, $SR^2$, $NR^2_2$—, $NH_2$, —$N_2H_3$, $NO_2$, CN, $CO_2R^2$, $COR_2$, CHO, $PR^2_2$—, —$SiR^2_3$ or —$OSiR^2_3$ substituents, and $R^7$ are identical or different and are each halogen, a linear, branched or cyclic $C_1$–$C_{40}$-group, for example a $C_1$–$C_{20}$-alkyl group or a $C_6$–$C_{14}$-aryl group, or $R^7$ form a ring system.

Also preferred are diboranes, for example of the type

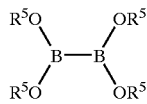

-continued

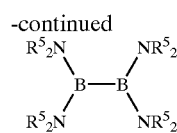

where $R^5$ is as defined above, in particular the compounds

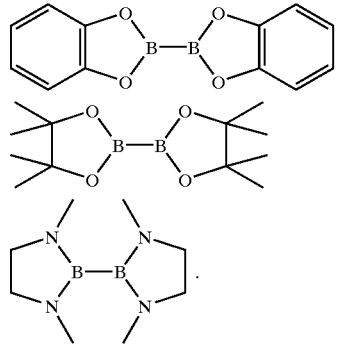

Examples of carbon-containing coupling components are alkenes and alkynes. Particular preference is given to alkenes and alkynes of the formula

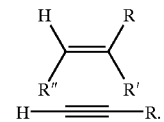

R, R' and R" are identical or different and are each H or a $C_1$–$C_{10}$-alkyl group, where one or more of the $CH_2$ groups may be replaced by identical or different O, S, $NR^2$, —CO—, —OC=O—, C(O)O, —$CONR^2$, $C_6$–$C_{14}$-arylene —$CH_2$=$CH_2$—, —C≡C— or —$SiR^2$ groups and one or more H of R may be replaced by identical or different $C_1$–$C_4$-alkyl, OH, $SiR_3^2$, halogen, —C≡N—, —$N_3$, $NR_2^2$, COOH, —$CO_2R^2$ or —OC(O)$R^2$ substituents, where R, R' and R" may form one or more ring systems and $R^2$ is as defined in formula I.

Very particular preference is given to alkenes and alkynes in which R, R' are identical or different and are each H or a $C_1$–$C_6$-alkyl group, where one or two $CH_2$ groups may be replaced by identical or different —CO—, —C(O)O—, $CONR^2$ and phenylene groups and from 1 to 3 H of R may be replaced by identical or different $SiR_3^2$, OH, F, Cl, CN and $CO_2R^2$ substituents, and in which R" is H and $R^2$ is as defined above.

Examples of silicon-containing coupling components are compounds of the type $R^4$—$Si(R^7)_3$ with the abovementioned definitions for $R^4$ and $R^7$.

Examples of tin-containing coupling components are stannanes, for example of the type $R^4$—$Sn(R^7)_3$, and also distannanes of the type $(R^7)_3Sn$—$Sn(R^7)_3$ with the abovementioned definitions for $R^4$ and $R^7$.

Examples of phosphorus-containing coupling components are compounds of the type $(R^5)_2P$—$R^8$, where the radical $R^8$ is H, $Sn(R^7)_3$ or $Si(R^7)_3$ and $R^5$ and $R^7$ are as defined above.

Examples of fluorine-containing coupling components are fluoride salts in which the cation is an element of groups 1–3 of the Periodic Table of the Elements or, particularly preferably, is a bulky peralkylated ammonium, sulfonium, amidosulfonium, phosphonium, amidophosphonium or guanidinium cation.

The coupling components described are illustrated by the following examples which do not restrict the scope of the invention.

Examples of boronic acids and boronic esters are:

phenylboronic acid p-tolylboronic acid m-tolylboronic acid o-tolylboronic acid 2,3-dimethylphenylboronic acid 2,4-dimethylphenylboronic acid 2,6-dimethylphenylboronic acid 3,5-dimethylphenylboronic acid mesitylboronic acid tetramethylphenylboronic acid butylphenylboronic acid 4-tert-butylphenylboronic acid 4-ethylphenylboronic acid tert-butylphenylboronic acid isopropylphenylboronic acid cyclohexylphenylboronic acid 4-(hex-5-en-1-yl)phenylboronic acid triisopropylsilylphenylboronic acid p-methoxyphenylboronic acid m-methoxyphenylboronic acid o-methoxyphenylboronic acid 2,4-dimethoxyphenylboronic acid 2,5-dimethoxyphenylboronic acid 3,5-dimethoxyphenylboronic acid 2,3,4-trimethoxyphenylboronic acid 2,4,6-trimethoxyphenylboronic acid 3,4,5-trimethoxyphenylboronic acid p-phenoxyphenylboronic acid p-ethoxyphenylboronic acid 2-(3'-phenylboronic acid)-1,3-dioxolane 3,4-(methylenedioxy)phenylboronic acid 3,4-(isopropylidenedioxy)phenylboronic acid p-thioanisylboronic acid m-thioanisylboronic acid o-thioanisylboronic acid p-nitrophenylboronic acid o-nitrophenylboronic acid m-nitrophenylboronic acid 3-nitro-4-methylphenylboronic acid 3-nitro-4-bromophenylboronic acid 4-(methoxycarbonyl)phenylboronic acid 3-(methoxycarbonyl)phenylboronic acid 2-(methoxycarbonyl)phenylboronic acid 4-carboxylphenylboronic acid 3-carboxylphenylboronic acid 2-carboxylphenylboronic acid formylphenylboronic acid acetylphenylboronic acid pivaloylphenylboronic acid o-fluorophenylboronic acid m-fluorophenylboronic acid p-fluorophenylboronic acid 2,3-difluorophenylboronic acid 2,4-difluorophenylboronic acid 3,5-difluorophenylboronic acid 2,3,4-trifluorophenylboronic acid 2,4,6-trifluorophenylboronic acid tetrafluorophenylboronic acid pentafluorophenylboronic acid o-chlorophenylboronic acid m-chlorophenylboronic acid p-chlorophenylboronic acid 3,5-dichlorophenylboronic acid 2,4,6-trichlorophenylboronic acid p-bromophenylboronic acid p-trifluoromethylphenylboronic acid m-trifluoromethylboronic acid o-trifluoromethylboronic acid 2,6-bis(trifluoromethyl)phenylboronic acid 3,5-bis(trifluoromethyl)phenylboronic acid p-trifluoromethyltetrafluorophenylboronic acid trifluoromethoxyphenylboronic acid o-cyanophenylboronic acid m-cyanophenylboronic acid p-cyanophenylboronic acid tetrafluorocyanophenylboronic acid m-aminophenylboronic acid p-aminophenylboronic acid tetrafluoro-4-aminophenylboronic acid 3-amino-4-methylphenylboronic acid p-dimethylaminophenylboronic acid m-dimethylaminophenylboronic acid o-dimethylaminophenylboronic acid hydrazylphenylboronic acid p-hydroxyphenylboronic acid m-hydroxyphenylboronic acid o-hydroxyphenylboronic acid 3-hydroxy-4-phenylboronic acid 2,4-dihydroxyphenylboronic acid 3,5-dihydroxyphenylboronic acid 1-naphthylboronic acid 2-naphthylboronic acid 2-methyl-1-naphthylboronic acid 4-methyl-1-naphthylboronic acid 4-methoxy-1-naphthylboronic acid 6-methoxy-2-naphthylboronic acid 2-biphenylboronic acid 3-biphenylboronic acid 4-biphenylboronic acid 3,5-diphenylphenylboronic acid p-styrylboronic acid m-styrylboronic acid o-styrylboronic acid 9-anthraceneboronic acid 9-phenanthreneboronic acid 2-furanboronic acid 3-furanboronic acid 5-methyl-2-furanboronic acid benzofuranboronic acid 2-thiopheneboronic acid 3-thiopheneboronic acid 5-methyl-2-thiopheneboronic acid benzothiopheneboronic acid N-methyl-2-pyrroleboronic acid N-methyl-3-pyrroleboronic acid 2-pyridineboronic acid 3-pyridineboronic acid 4-pyridineboronic acid pyrimidineboronic acid 2-quinolineboronic acid 3-quinolineboronic acid 4-isoquinolineboronic acid tetrafluoropyridineboronic acid vinylboronic acid but-2-en-2-ylboronic acid hexenylboronic acid cyclohexenylboronic acid 2-phenylethenylboronic acid 6-methoxyhex-1-ene-1-boronic acid allylboronic acid benzylboronic acid p-methoxybenzylboronic acid ethynylboronic acid 2-trimethylsilylethynylboronic acid 2-phenylethynylboronic acid hex-1-yne-1-boronic acid tert-butylacetyleneboronic acid n-butylboronic acid cyclohexylboronic acid isopropylboronic acid phenylboronic acid dimethyl ester phenylboronic acid diethyl ester phenylboronic acid dibutyl ester phenylboronic acid diisopropyl ester phenylboronic acid dicyclohexyl ester phenylboronic acid di-tert-butyl ester phenylboronic acid diphenyl ester p-tolylboronic acid dimethyl ester p-tolylboronic acid diethyl ester p-tolylboronic acid diisopropyl ester 3,5-dimethylphenylboronic acid dibutyl ester 3,5-bis(trifluoromethyl)phenylboronic acid methyl ester 1-naphthylboronic acid dimethyl ester 1-naphthylboronic acid diethyl ester 1-naphthylboronic acid dibutyl ester 1-naphthylboronic acid diisopropyl ester 1-naphthylboronic acid diphenyl ester 2-naphthylboronic acid dimethyl ester 2-naphthylboronic acid diisopropyl ester 2-furanboronic acid dimethyl ester 3-furanboronic acid diisopropyl ester 2-thiopheneboronic acid dimethyl ester n-methylpyrrole-2-boronic acid diisopropyl ester pyridineboronic acid dimethyl ester pyridineboronic acid diisopropyl ester B-n-butylcatecholborane B-(1-hexenyl)catecholborane B-cyclohexylcatecholborane B-phenylcatecholborane B-(1-naphthyl)catecholborane B-(2-naphthyl)catecholborane B-ethynylcatecholborane B-(2-trimethylsilylethynyl)catecholborane B-(2-phenylethynyl)catecholborane B-(hex-1-yn-1-yl)catecholborane B-(tert-butylethynyl)catecholborane phenylboronic acid pinacol ester phenylboronic acid cyclohexanediol ester phenylboronic acid trimethylene glycol ester phenylboronic acid glycol ester phenylboronic acid 2',2'-dimethylpropanediol ester 1-naphthylboronic acid cyclohexanediol ester 1-naphthylboronic acid trimethylene glycol ester 1-naphthylboronic acid pinacol ester 1-naphthylboronic acid glycol ester 2-naphthylboronic acid trimethylene glycol ester 2-naphthylboronic acid pinacol ester methoxyphenylboronic acid dimethyl ester aminophenylboronic acid tributyl ester nitrophenylboronic acid pinacol ester fluorophenylboronic acid trimethylene glycol ester chlorophenylboronic acid diisopropyl ester bromophenylboronic acid pinacol ester cyanophenylboronic acid pinacol ester 4-(methoxycarbonyl)phenylboronic acid pinacol ester 4-(methoxycarbonyl)phenylboronic acid trimethylene glycol ester vinylboronic acid dimethyl ester B-vinylcatecholborane vinylboronic acid trimethylene glycol ester hex-1-en-1-ylboronic acid diisopropyl ester B-hexenylcatecholborane cyclohexenylboronic acid diethyl ester B-cyclohexenylcatecholborane 2-phenylethenylboronic acid diphenyl ester 2-phenylethenylcatecholborane 6-methoxyhex-1-ene-1-boronic acid dimethyl ester allylboronic acid diisopropyl ester allylboronic acid pinacol ester allylcatecholborane benzylboronic acid diisopropyl ester p-methoxybenzylboronic acid trimethylene glycol ester ethynylboronic acid diisopropyl ester 2-trimethylsilylethynylboronic acid diisopropyl ester 2-trimethylsilylethynylboronic acid trimethylene glycol ester 2-phenylethynylboronic acid pinacol ester 2-phenylethynylboronic acid diisopropyl ester hex-1-yn-1-boronic acid diisopropyl ester hex-1-yn-1-boronic acid dibutyl ester tert-butylacetyleneboronic acid diisopropyl ester tert-butylacetyleneboronic acid pinacol ester n-butylboronic acid dimethyl ester n-butylboronic acid diisopropyl ester B-n-butylcatecholborane n-butylboronic acid trimethylene glycol ester n-butylboronic acid pinacol ester cyclohexylboronic acid dimethyl ester B-cyclohexylcatecholborane cyclohexylboronic acid trimethylene glycol ester isopropylboronic acid diethyl ester B-isopropylcatecholborane isopropylboronic acid pinacol ester Examples of above-described boranes are:

B-n-butyl-9-borabicyclo[3.3.1]nonane=B-n-butyl-9-BBN B-isoamyl-9-BBN B-(hex-1-en-1-yl)-9-BBN B-vinyl-9-BBN B-cyclohexyl-9-BBN B-(2-trimethylsilylethen-1-yl)-9-BBN B-phenyl-9-BBN B-(1-naphthyl)-9-BBN B-(2-naphthyl)-9-BBN B-(3,5-bis(trifluoromethyl)phenyl)-9-BBN B-(2-phenylethyn-1-yl)-9-BBN B-(2-phenylethen-1-yl)-9-BBN B-benzyl-9-BBN B-allyl-9-BBN ethyldisiamylborane n-butyldisiamylborane amyldisiamylborane cyclohexyldisiamylborane vinyldisiamylborane hex-1-en-1-yldisiamylborane 2-phenylethen-1-yldisiamylborane 2-trimethylsilylethen-1-yldisiamylborane phenyldisiamylborane naphthyldisiamylborane benzyldisiamylborane 2-trimethylsilylethyn-1-yldisiamylborane tributylborane cyclohexyldibutylborane vinyldibutylborane hex-1-en-1-yldibutylborane 2-phenylethen-1-yldibutylborane 2-trimethylsilylethen-1-yldibutylborane phenyldibutylborane naphthyldibutylborane benzyldibutylborane 2-trimethylsilylethyn-1-yldibutylborane ethyldicyclohexylborane n-butyldicyclohexylborane amyldicyclohexylborane vinyldicyclohexylborane hex-1-en-1-yldicyclohexylborane 2-phenylethen-1-yldicyclohexylborane 2-trimethylsilylethen-1-yldicyclohexylborane phenyldicyclohexylborane naphthyldicyclohexylborane benzyldicyclohexylborane 2-trimethylsilylethyn-1-yldicyclohexylborane di-n-butylthexylborane divinylthexylborane dihex-1-en-1-ylthexylborane diphenylthexylborane dinaphthylthexylborane bis-(2-trimethylsilylethen-1-yl)thexylborane n-butyldibromoborane n-butyldichloroborane amyldibromoborane cyclohexyldibromoborane vinyldibromoborane vinyldichloroborane hex-1-en-1-yldibromoborane 2-phenylethen-1-yldibromoborane 2-phenylethen-1-yldichloroborane 2-trimethylsilylethen-1-yldifluoroborane phenyldibromoborane phenyldichloroborane naphthyldibromoborane benzyldibromoborane 2-trimethylsilylethyn-1-yldibromoborane tert-butylethynyldifluoroborane butyldiisopinocamphenylborane vinyldiisopinocamphenylborane hex-1-en-1-yldiisopinocamphenylborane phenyldiisopinocamphenylborane naphthyldiisopinocamphenylborane 2-trimethylsilylethen-1-yldiisopinocamphenylborane Examples of above-described stannanes and distannanes are:

phenyltrimethylstannane phenyltributylstannane tetraphenylstannane p-tolyltrimethylstannane m-tolyltributylstannane o-tolyltrimethylstannane 2,3-dimethylphenyltrimethylstannane 2,4-dimethylphenyltributylstannane 2,6-dimethylphenyltrimethylstannane 3,5-dimethylphenyltrimethylstannane mesityltrimethylstannane tetramethylphenyltrimethylstannane butylphenyltrimethylstannane tert-butylphenyltributylstannane isopropylphenyltrimethylstannane cyclohexylphenyltrimethylstannane 4-(hex-5-en-1-yl)phenyltrimethylstannane triisopropylsilylphenyltrimethylstannane p-methoxyphenyltrimethylstannane m-methoxyphenyltributylstannane o-methoxyphenyltrimethylstannane 2,4-dimethoxyphenyltrimethylstannane 2,5-dimethoxyphenyltrimethylstannane 3,5-dimethoxyphenyltributylstannane 2,3,4-trimethoxyphenyltrimethylstannane 2,4,6-trimethoxyphenyltrimethylstannane 3,4,5-trimethoxyphenyltributylstannane p-phenoxyphenyltrimethylstannane p-ethoxyphenyltrimethylstannane 2-(3'-phenyltrimethylstannane)-1,3-dioxolane 3,4-(methylenedioxy)phenyltrimethylstannane 3,4-(isopropylidenedioxy)phenyltrimethylstannane p-thioanisyltributylstannane m-thoianisyltrimethylstannane o-thioanisyltrimethylstannane p-nitrophenyltrimethylstannane o-nitrophenyltributylstannane m-nitrophenyltrimethylstannane 3-nitro-4-methylphenyltrimethylstannane 3-nitro-4-bromophenyltrimethylstannane 4-(methoxycarbonyl)phenyltributylstannane 3-(methoxycarbonyl)phenyltrimethylstannane 2-(methoxycarbonyl)phenyltrimethylstannane 4-carboxylphenyltrimethylstannane 3-carboxylphenyltributylstannane 2-carboxylphenyltrimethylstannane formylphenyltrimethylstannane acetylphenyltrimethylstannane pivaloylphenyltrimethylstannane o-fluorophenyltrimethylstannane m-fluorophenyltrimethylstannane p-fluorophenyltributylstannane 2,3-difluorophenyltrimethylstannane 2,4-difluorophenyltrimethylstannane 3,5-difluorophenyltriethylstannane 2,3,4-trifluorophenyltrimethylstannane 2,4,6-trifluorophenyltrimethylstannane tetrafluorophenyltriethylstannane pentafluorophenyltrimethylstannane o-chlorophenyltrimethylstannane m-chlorophenyltributylstannane p-chlorophenyltrimethylstannane 3,5-dichlorophenyltrimethylstannane 2,4,6- trichlorophenyltrimethylstannane
p-bromophenyltrimethylstannane
p-trifluoromethylphenyltrimethylstannane
m-trifluoromethyltributylstannane
o-trifluoromethyltrimethylstannane 2,6-bis(trifluoromethyl)phenyltrimethylstannane 3,5-bis(trifluoromethyl)phenyltributylstannane
p-trifluoromethyltetrafluorophenyltrimethylstannane
trifluoromethoxyphenyltrimethylstannane
o-cyanophenyltrimethylstannane
m-cyanophenyltributylstannane
p-cyanophenyltrimethylstannane tetrafluorocyanophenyltrimethylstannane
m-aminophenyltrimethylstannane
p-aminophenyltrimethylstannane tetrafluoro-4-aminophenyltrimethylstannane 3-amino-4-methylphenyltrimethylstannane
p-dimethylaminophenyltrimethylstannane
m-dimethylaminophenyltrimethylstannane
o-dimethylaminophenyltrimethylstannane hydrazylphenyltrimethylstannane
p-hydroxyphenyltrimethylstannane
m-hydroxyphenyltributylstannane
o-hydroxyphenyltrimethylstannane 3-hydroxy-4-phenyltrimethylstannane 2,4-dihydroxyphenyltrimethylstannane 3,5-dihydroxyphenyltrimethylstannane
1-naphthyltrimethylstannane
1-naphthyltributylstannane
2-naphthyltrimethylstannane 2-methyl-1-naphthyltrimethylstannane 4-methyl-1-naphthyltrimethylstannane 4-methoxy-1-naphthyltrimethylstannane 6-methoxy-2-naphthyltrimethylstannane
2-biphenyltrimethylstannane
3-biphenyltrimethylstannane
4-biphenyltrimethylstannane 3,5-diphenylphenyltrimethylstannane
p-styryltrimethylstannane m-styryltrimethylstannane
o-styryltrimethylstannane
9-anthracenetrimethylstannane
9-phenanthrenetrimethylstannane
2-furantrimethylstannane 3-furantrimethylstannane
benzofurantrimethylstannane
2-thiophenetrimethylstannane
3-thiophenetrimethylstannane benzothiophenetrimethylstannane N-methyl-2-pyrroletrimethylstannane
N-methyl-3-pyrroletrimethylstannane thiazoletributylstannane N-methylimidazoletrimethylstannane
N-methylbenzoimidazoletrimethylstannane oxazoletributylstannane benzothiazoletrimethylstannane
N-methyltriazoletributylstannane
2-pyridinetrimethylstannane
3-pyridinetrimethylstannane
4-pyridinetrimethylstannane pyrimidinetrimethylstannane 2-quinolinetrimethylstannane
3-quinolinetrimethylstannane
4-isoquinolinetrimethylstannane tetrafluoropyridinetrimethylstannane vinyltrimethylstannane
2-trimethylsilylethene-1-tributylstannane but-2-en-2-yltrimethylstannane methyl 3-tributylstannyl acrylate hexenyltrimethylstannane cyclohexenyltrimethylstannane 2-phenylethenyltrimethylstannane
6-methoxyhex-1-ene-1-trimethylstannane allyltrimethylstannane benzyltrimethylstannane
p-methoxybenzyltrimethylstannane ethynyltrimethylstannane 2-trimethylsilylethynyltrimethylstannane
2-phenylethynyltrimethylstannane hex-1-ynyl-1-trimethylstannane tert-butylacetylenetrimethylstannane
n-butyltrimethylstannane cyclohexyltrimethylstannane isopropyltrimethylstannane hexamethyldistannane hexaethyldistannane hexabutyldistannane hexaphenyldistannane Examples of the above-described alkenes and alkynes are:
ethylene, styrene, α-methylstyrene, p-methylstyrene, 2,4,6-trimethylstyrene, p-methoxystyrene, p-vinylstyrene, p-dimethylaminostyrene, p-chlorostyrene, p-aminostyrene, vinylnaphthalene, p-hydroxystyrene, methyl acrylate, ethyl acrylate, butyl acrylate, octadecyl acrylate, t-butyl acrylate, dimethylaminoethyl acrylate, hydroxyethyl acrylate, acrylamide, N,N-dimethylacrylamide, methyl methacrylate, ethyl methacrylate, butyl methacrylate, octadecyl methacrylate, t-butyl methacrylate, dimethylaminoethyl methacrylate, hydroxyethyl methacrylate, N,N-diethylmethacrylamide acrylonitrile, methacrylonitrile vinylpyridines, butadiene, isoprene, phenylbutadiene, cyclohexene, cyclopentene, methyl vinyl ketone, cyclohexenone, cyclopentenone, acrolein, acetylene, propyne, hexyne, phenylacetylene, t-butylacetylene, trimethylsilylacetylene, propargyl alcohol, methyl propynoate, propargyl aldehyde, vinylacetylene, dihydrofuran, dihydropyran.

Examples of above-described silicon compounds are:
phenyltrimethylsilane phenyltrifluorosilane naphthyltrimethylsilane naphthyltrifluorosilane 2-pyridyltrimethylsilane
p-methoxyphenyltriethylsilane trifluoromethylphenyltrimethylsilane vinyltrifluorosilane vinyltrimethylsilane hex-1-en-1-yltrimethylsilane ethynyltrimethylsilane ethynyltrichlorosilane tert-butylethynyltrifluorosilane Examples of above-described phosphorus compounds are:
diphenylphosphine di(o-tolyl)phosphine di(bis(trifluoromethyl)phenylphosphine) trimethylstannyldi(p-methoxyphenyl)phosphine trimethylsilyldiphenylphosphine trimethylstannyldiphenylphosphine dibutylphosphine dimethylphosphine triethylsilyldimethylphosphine dicyclohexylphosphine trimethylsilyldicyclohexylphosphine trimethylstannylcyclohexylbutylphosphine The process of the present invention for preparing indanones of the formula II or IIa can be carried out, for example, by reacting the indanones of the formula I or Ia with the above-described coupling components such as boron-, carbon-, tin-, silicon- or phosphorus-containing compounds in a solvent, eg. a nonpolar, polar aprotic or polar protic solvent or any mixtures of components of these solvent classes.

Solvents which can be used are, for example, hydrocarbons, halogenated hydrocarbons, ethers, polyethers, ketones, esters, amides, amines, ureas, sulfoxides, sulfones, phosphoramides, alcohols, polyalcohols, water and mixtures of these.

Preferred solvents are aromatics such as benzene, toluene, xylene, mesitylene, ethylbenzene, ethers such as diethyl ether, MTBE, THF, dioxane, anisole, di-n-butyl ether, DME, diglyme, triglyme, acetone, ethyl methyl ketone, isobutyl methyl ketone, ethyl acetate, DMF, dimethylacetamide, NMP, EMPA, acetonitrile, triethylamine, water, methanol, ethanol, isopropanol, isobutanol, ethylene glycol, diethylene glycol, glycerol, triethylene glycol and mixtures of these.

Particular preference is given to toluene, xylene, diethyl ether, MTBE, THF, DME, diglyme, acetone, DMF, NMP, water, ethylene glycol and mixtures of these.

The process of the present invention can be carried out, if desired, in the presence of a catalyst and, if desired, in the presence of a base, a salt-like additive or a phase transfer catalyst.

The catalysts which can be used in the process of the present invention comprise transition metal components such as transition metals or transition metal compounds and, if desired, cocatalyst components which can act as ligands.

As transition metal components, preference is given to using transition metals of groups 6 to 12 of the Periodic Table of the Elements or compounds of these transition metals.

Particularly preferred transition metal components are transition metals of groups 8 to 10 of the Periodic Table of the Elements.

Preferred transition metal components are nickel, palladium and platinum and also compounds of these transition metals, in particular nickel and palladium and also their compounds (J. Tsuji, Palladium-Reagents and Catalysts, Wiley 1995; M. Beller et al., Angew. Chem., 107, 1995, pp. 1992–1993), which can, if desired, be used in the presence of one or more cocatalysts.

Illustrative examples of catalysts, which, however, do not restrict the Scope of the invention, are $Ni(CO_4)$, $NiCl_2(PPh_3)_2$, $NiCl_2(PBu_3)_2$, $Ni(PF_3)_4$, $Ni(COD)_2$, $Ni(PPh_3)_4$, $Ni(acac)_2$, $Ni(dppe)Cl_2$, $Ni(dppp)Cl_2$, $Ni(dppf)Cl_2$, $NiCl_2(PMe_3)_2$, $Pd(OAc)_2/PPh_3$, $Pd(OAc)_2/P(MeOPh)_3$, $Pd(OAc)_2/PBu_3$, $Pd(OAc)_2/AsPh_3$, $Pd(OAc)_2/SbPh_3$, $Pd(OAc)_2/dppe$, $Pd(OAc)_2/dppp$, $Pd(OAc)_2/dppf$, $Pd(OAc)_2/P(o\text{-tolyl})_3$, $Pd(OAc)_2/\text{tris}(m\text{-PhSO}_3\text{Na})$phosphine, $Pd(PPh_3)_4$, $Pd_2(dba)_3*CHCl_3$, $PdCl_2/PPh_3$, $PdCl_2/P(o\text{-tolyl})_3$, $PdCl_2(PPh_3)_2$, $PdCl_2(MeCN)_2$, $PdCl_2(PhCN)_2$, $Pd(acac)_2$, $[(allyl)PdCl]_2$, $PdCl_2(dppp)$, $PdCl_2(dppe)$, $PdCl_2(COD)$, $PdCl_2(dppf)$, Pd on carbon/$PPh_3$, $Pd(OAc)_2/P(OMe)_3$ and mononuclear and polynuclear palladacycles.

Very particularly preferred catalysts are $NiCl_2(PPh_3)_2$, $Ni(dppe)Cl_2$, $Ni(dppp)Cl_2$, $Ni(dppf)Cl_2$, $Pd(OAc)_2/PPh_3$, $Pd(OAc)_2/P(o\text{-tolyl})_3$, $Pd(PPh_3)_4$, $PdCl_2(PPh_3)_2$, $PdCl_2/PPh_3$, $PdCl_2(dppp)$, $PdCl_2(dppe)$, $PdCl_2(dppf)$, $Pd(OAc)_2/\text{tris}(m\text{-PhSO}_3\text{Na})$phosphine, and

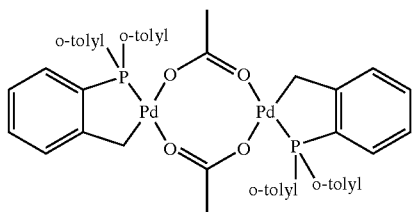

The amount of catalyst used is generally from 100 mol % to $10^{-6}$ mol %, preferably from 10 mol % to $10^{-5}$ mol %, particularly preferably from 5 mol % to $10^{-4}$ mol %, in each case based on the indanone of the formula I or Ia.

If desired, the process of the present invention is carried out in the presence of bases and/or phase transfer catalysts.

Illustrative examples of bases, which do not, however, restrict the scope of the invention, are hydroxides, alkoxides, carboxylates, carbonates and hydrogen carbonates, oxides, fluorides, phosphates and amines.

Preferred bases are $Li_2CO_3$, $Na_2CO_3$, $NaHCO_3$, $K_2CO_3$, $Cs_2CO_3$, LiOH, NaOH, KOH, CsOH, NaOMe, KO$^t$Bu, $K_3PO_4$, LiF, NaF, KF, CsF, NaOAc, KOAc, $Ca(OAc)_2$, $R(t\text{-BuCO}_2)$, CaO, BaO, $Ca(OH)_2$, $Ba(OH)_2$, $MgCO_3$, $CaCO_3$, $BaCO_3$, TlOH, $Tl_2CO_3$, $Ag_2O$, $ZnCO_3$, $Bu_4NF$, $[(Et_2N)_3S]Me_{3SiF2}$, DBU or amines such as triethylamine, diisopropylethylamine, dicyclohexylethylamine or dimethylaniline.

Phase transfer catalysts which can be used are ammonium or phosphonium salts and also crown ethers. Illustrative examples of phase transfer catalysts, which do not, however, restrict the scope of the invention are $Bu_4NCl$, $Bu_4NBr$, $Bu_4NI$, $BU_4NHSO_4$, $Et_3BnNBr$, $Me_3BnNCl$, aliquot, $Ph_4PBr$, $Ph_4PCl$, 18-crow-6, 15-crown-5, 12-crown-4, dibenzo-18-crown-6.

If desired, the reaction can be carried out in the presence of one or more salt-like additives. Illustrative examples of salt-like additives, which do not, however, restrict the scope of the invention, are LiCl, LiBr, LiF, Li, $LiBF_4$, $LiPF_6$, $LiClO_4$, $LiCF_3CO_2$, lithium triflate, $LiNTf_2$, $AgNO_3$, $AgBF_4$, $AgCF_3CO_2$, silver triflate, $AgPF_6$, CuCl, CuBr, CuJ, CuCN, $Li_2CU(CN)Cl_2$, $ZnCl_2$, $ZnBr_2$, $ZnI_2$, zinc triflate and $Zn(CF_3CO_2)_2$.

The process of the present invention is generally carried out at from –100° C. to +600° C., preferably from –78° C. to +350° C., particularly preferably at from 0° C. to 180° C.

The reaction generally takes place at a pressure of from 10 mbar to 1000 bar, preferably from 0.5 bar to 100 bar.

The reaction can be carried out in a single-phase system or in a multiphase system.

The concentration of indanone of the formula I or Ia in the reaction mixture is generally in the range from 0.0001 mol/l to 8 mol/l, preferably from 0.01 mol/l to 3 mol/l, particularly preferably from 0.1 mol/l to 2 mol/l.

The molar ratio of coupling component to indanone of the formula I or Ia is generally from 0.1 to 10, preferably from 0.5 to 3.

The molar ratio of base to indanone of the formula I or Ia is generally from 0 to 50.

The molar ratio of phase transfer catalyst to indanone of the formula I or Ia is generally from 0 to 2, preferably from 0 to 0.1.

The molar ratio of salt-like additives to indanone of the formula I or Ia is generally from 0 to 10.

The time of the reaction of indanones of the formula I or Ia with above-described coupling components to give indanones of the formula II or IIa is generally from 5 minutes to 1 week, preferably from 15 minutes to 48 hours.

The reaction of an indanone of the formula I or Ia with a boronic acid is preferably carried out under conditions in which the transition metal component used is a compound of a transition metal of groups 8 to 10 of the Periodic Table of the Elements, a base such as an alkoxide, hydroxide, carbonate, carboxylate, hydrogencarbonate, oxide, fluoride, phosphate or amine is used and a solvent such as a hydrocarbon, ether, polyether, alcohol, polyalcohol or water or any mixture of these is used and the reaction temperature is from –100° to 500° C.

Particular preference is given to conditions in which the transition metal component used is a compound of the transition metals Ni, Pd or Pt, the base used is an alkoxide, hydroxide, hydrogencarbonate, carbonate, carboxylate or phosphate, the solvent used is an aromatic hydrocarbon, ether, polyether, alcohol, polyalcohol or water or any mixture of these and the reaction temperature is from –78 to 300° C.

Very particular preference is given to conditions in which the transition metal component used is a palladium compound, the base is an alkali metal or alkaline earth metal alkoxide, hydroxide, carbonate, carboxylate or orthophosphate, the solvent is toluene, xylene, mesitylene, ethylbenzene, THF, dioxane, DME, diglyme, butanol, ethylene glycol, glycerol or water or any mixture of these and the reaction temperature is from –30° to 200° C.

Extraordinary preference is given to conditions in which the transition metal compound is a palladium compound, the base is an alkali metal or alkaline earth metal carbonate, hydroxide or orthophosphate, the solvent is toluene, xylene, THF, DME, diglyme, ethylene glycol or water or any mixture of these and the reaction temperature is from 0° C. to 160° C.

Illustrative examples of reaction conditions in the reaction of an indanone of the formula I or Ia with a boronic acid, which do not, however, restrict the scope of the invention, are:

X (in formula I or Ia)=Br; catalyst: 0.01–5 mol % of Pd(P(Ph$_3$)$_4$); base: aqueous sodium carbonate solution; solvent: toluene; reaction temperature: reflux; reaction time: 1–24 h.

X (in formula I or Ia)=Cl; catalyst: 0.01–15 mol % of NiCl$_2$(dppf); base: K$_3$PO$_4$; solvent: dioxane; reaction temperature: 80° C.; reaction time: 1–24 h.

X (in formula I or Ia)=Br; catalyst: 0.01–5 mol % of Pd(OAc)$_2$/PPh$_3$; base: aqueous potassium carbonate solution; solvent: xylene; reaction temperature: reflux; reaction time: 1–24 h.

X (in formula I or Ia)=Cl or Br; catalyst: 0.01–5 mol % of
(OAc)$_2$/P(m-HSO$_3$—Ph)$_3$; base: aqueous sodium carbonate solution; solvent: xylene/ethylene glycol; reaction temperature: reflux; reaction time: 1–24 h.

X (in formula I or Ia)=I or trifluoromethanesulfonate; catalyst: 0.01–1 mol % of PdCl$_2$(NC—Ph)$_2$; base: sodium carbonate; solvent: DME; additive: 5 mol % of tetrabutylammonium bromide; reaction temperature: reflux; reaction time: 1–24 h.

X (in formula I or Ia)=Br; catalyst: 0.01–5 mol % of Pd(OAc)$_2$/P(o-tol)$_3$; base: triethylamine; solvent: dimethylformamide (DMF); reaction temperature: 100° C.; reaction time: 1–24 h.

Preference is given to carrying out the reaction of an indanone of the formula I or Ia with a stannane to give indanones of the formula II or IIa, where R$^3$ is preferably an aryl, heteroaryl or alkenyl group, the transition metal compound is a compound of a transition metal of groups. 8–10 of the Periodic Table of the Elements, the solvent is a hydrocarbon, ether, polyether, amide or nitrile, the additive is a lithium salt, a zinc salt, a copper salt, a silver salt or a fluoride salt and the reaction temperature is from −78° C. to 300° C. and the reaction time is from 5 minutes to 1 week.

In the reaction with a stannane, particular preference is given to conditions in which R$^3$ is preferably an aryl, heteroaryl (with the heteroatoms N, O and S) or alkenyl group, and in which the transition metal component is a palladium compound, the solvent is an aromatic hydrocarbon, ether, THF, dioxane, DME, DMF, HMPA, NMP or acetonitrile, the additive is a lithium or copper(I) salt and the reaction temperature is from −30 to 200° C. and the reaction time is from 10 minutes to 48 hours.

Illustrative examples of reaction conditions in the reaction of an indanone of the formula I or Ia with a stannane, which do not, however, restrict the scope of the invention, are:

X (in formula I or Ia)=I; catalyst: 0.1–5 mol % of PdCl$_2$(PPh$_3$)$_2$; solvent: DME; additive: lithium chloride; temperature: 85° C.; reaction time: 12–24 h.

X (in formula I or Ia)=Br; catalyst: 0.5–10 mol % of Pd(OAc)$_2$/P(o-tolyl)$_3$; solvent: xylene; additive: CuI; temperature: 135° C.; reaction time: 3–6 h.

The reaction of an indanone of the formula I and Ia with an olefin is preferably carried out under conditions in which the transition metal component is a compound of a transition metal of groups 8–10 of the Period Table of the Elements, the base is an amine or carboxylate, the solvent is an amide, amine, urea, nitrile, alcohol or water and the reaction temperature is from −78 to 250° C.

Particular preference is given to conditions in which the transition metal component is a palladium compound, the base is a tertiary amine, carboxylate or DBU, the solvent is an amide, nitrile or alcohol and the reaction temperature is from 0 to 200° C.

Illustrative examples of reaction conditions in the reaction of an indanone of the formula I or Ia with an olefin, which do not, however, restrict the scope of the invention, are:

X (in formula I or Ia)=Br; olefin: butyl acrylate; catalyst: 0.01–5 mol % of Pd(OAc)$_2$/PPh$_3$; base: triethylamine; solvent: dimethylformamide; temperature 130° C.

X (in formula I or Ia)=trifluoromethanesulfonate; olefin: methyl methacrylate; catalyst: 0.01–5 mol % of Pd/C/PPh$_3$; base: diisopropylethylamine; solvent: dimethylacetamide; temperature: 130° C.

X (in formula I or Ia)=Cl; olefin: acrylonitrile; catalyst: 0.01–1 mol % of [(o-tolyl)$_2$P-(o-benzyl)Pd]$_2$(OAc)$_2$; base: sodium acetate; solvent: acetonitrile; temperature: 100° C.

The present invention also provides substituted indanones of the formula III,

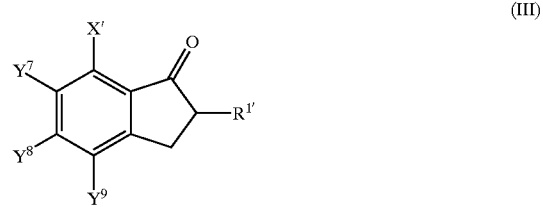

(III)

where

R$^{1'}$ is a C$_1$–C$_{40}$-hydrocarbon group which is bound via a carbon atom and may bear one or more identical or different heteroatom-containing radicals, except for nitrogen-containing radicals, as substituents, eg. a linear, branched or cyclic C$_1$–C$_{20}$-alkyl group which may bear one or more identical or different halogen, OH, OR$^2$, SR$^2$, PR$^2_2$—, —SiR$^2_3$ or —OSiR$^2_3$ substituents, a C$_6$–C$_{22}$-aryl group which may bear one or more identical or different halogen, OH, OR$^2$, SR$^2$, PR$^2_2$—, —SiR$^2_3$ or —OSiR$^2_3$ substituents, a C$_7$–C$_{20}$-alkylaryl group or a C$_7$–C$_{20}$-arylalkyl group, where the alkyl part may bear one or more identical or different halogen, OH, OR$^2$, SR$^2$, PR$^2_2$—, —SiR$^2_3$ or —OSiR$^2_3$ substituents and the aryl part may bear one or more identical or different halogen, OH, OR$^2$, SR$^2$, PR$^2_2$—, —SiR$^2_3$ or —OSiR$^2_3$ substituents, a C$_2$–C$_{10}$-alkenyl group which may bear one or more identical or different halogen, OH, OR$^2$, SR$^2$, PR$^2_2$—, —SiR$^2_3$ or —OSiR$^2_3$ substituents, a C$_2$–C$_{20}$-alkynyl group which may bear one or more identical or different halogen, OH, OR$^2$, SR$^2$, PR$^2_2$—, —SiR$^2_3$ or —OSiR$^2_3$ substituents, a C$_8$–C$_{12}$-arylalkenyl group, where the alkenyl part may bear one or more identical or different halogen, OH, OR$^2$, SR$^2$, PR$^2_2$—, —SiR$^2_3$ or —OSiR$^2_3$ substituents and the aryl part may bear one or more identical or different halogen, OH, $OR^2$, $SR^2$, $PR^2_2$—, —$SiR^2_3$ or —$OSiR^2_3$ substituents, or $R^{1'}$ is an $OR^2$, $SR^2$, $NR^2_2$, $PR^2_2$, $SiR^2_3$ or $OSiR^2_3$ group, where $R^2$ are identical or different and are each a $C_1$–$C_{20}$-hydrocarbon group such as a $C_1$–$C_{10}$-alkyl or $C_6$–$C_{14}$-aryl group which may each bear one or more identical or different halogen, OH, $OR^2$, $SR^2$, $NR^2_2$—, $PR^2_2$—, —$SiR^2_3$ or —$OSiR^2_3$ substituents, or two radicals $R^2$ may be joined to form a ring system or $R^{1'}$ is a $C_1$–$C_{20}$—, preferably $C_2$–$C_{20}$-heterocyclic group which is bound via a carbon atom and may in turn bear $C_1$–$C_{20}$-radicals or heteroatoms as substituents, X' is a leaving group, preferably a diazonium group, a halogen atom such as chlorine, bromine or iodine, or $C_1$–$C_{40}$-alkylsulfonate, $C_1$–$C_{40}$-haloalkylsulfonate, $C_6$–$C_{40}$-arylsulfonate, $C_6$–$C_{40}$-haloarylsulfonate, $C_7$–$C_{40}$-arylalkylsulfonate, $C_7$–$C_{40}$-haloarylalkylsulfonate, $C_1$–$C_{40}$-alkylcarboxylate, $C_1$–$C_{40}$-haloalkylcarboxylate, $C_6$–$C_{40}$-arylcarboxylate, $C_6$–$C_{40}$-haloarylcarboxylate, $C_7$–$C_{40}$-arylalkylcarboxylate, $C_7$–$C_{40}$-haloarylalkylcarboxylate, formate, $C_1$–$C_{40}$-alkyl carbonate, $C_1$–$C_{40}$-haloalkyl carbonate, $C_6$–$C_{40}$-aryl carbonate, $C_6$–$C_{40}$-haloaryl carbonate, $C_7$–$C_{40}$-arylalkyl carbonate, $C_7$–$C_{40}$-haloarylalkyl carbonate, $C_1$–$C_{40}$-alkyl phosphonate, $C_1$–$C_{40}$-haloalkyl phosphonate, $C_6$–$C_{40}$-aryl phosphonate, $C_6$–$C_{40}$-haloaryl phosphonate, $C_7$–$C_{40}$-arylalkyl phosphonate or $C_7$–$C_{40}$-haloarylalkyl phosphonate, $Y^7$ and $Y^8$ are identical or different and are each a hydrogen atom or are as defined for X' or are a $C_2$–$C_{40}$-hydrocarbon group which is bound via a carbon atom and may bear one or more identical or different heteroatom-containing radicals as substituents, eg. a linear, branched or cyclic $C_2$–$C_{20}$-alkyl group which may bear one or more identical or different halogen, OH, $OR^2$, $SR^2$, $NR^2_2$—, $PR^2_2$—, —$SiR^2_3$ or —$OSiR^2_3$ substituents, a $C_6$–$C_{22}$-aryl group which may bear one or more identical or different halogen, $OR^2$, $SR^2$, $NR^2_2$—, $NH_2$, —$N_2H_3$, $NO_2$, CN, $CO_2R^2$, CHO, $COR^2$, $PR^2_2$—, —$SiR^2_3$ or —$OSiR^2_3$ substituents, a $C_7$–$C_{15}$-alkylaryl group or $C_7$–$C_{15}$-arylalkyl group, where the alkyl part may bear one or more identical or different halogen, OH, $OR^2$, $SR^2$, $NR^2_2$—, $PR^2_2$—, —$SiR^2_3$ or —$OSiR^2_3$ substituents and the aryl part may bear one or more identical or different halogen, $OR^2$, $SR^2$, $NR^2_2$—, $NH_2$, —$N_2H_3$, $NO_2$, CN, $CO_2R^2$, CHO, $PR^2_2$—, —$SiR^2_3$ or —$OSiR^2_3$ substituents, a $C_2$–$C_{10}$-alkenyl group which may bear one or more identical or different halogen, OH, $OR^2$, $SR^2$, $NR^2_2$—, $PR^2_2$—, —$SiR^2_3$ or —$OSiR^2_3$ substituents, a $C_2$–$C_{10}$-alkynyl group which may bear one or more identical or different halogen, OH, $OR^2$, $SR^2$, $NR^2_2$—, $PR^2_2$—, —$SiR^2_3$ or —$OSiR^2_3$ substituents, a $C_8$–$C_{12}$-arylalkenyl group which may bear one or more identical or different halogen, OH, $OR^2$, $SR^2$, $NR^2_2$—, $PR^2_2$—, —$SiR^2_3$ or —$OSiR^2_3$ substituents, or $Y^7$ and $Y^8$ are each a halogen atom, a $NR^2_2$, $PR^2_2$, $B(OR^2)_2$, $SiR^2_3$ or $SnR^2_3$ group, where $R^2$ are identical or different and are each a $C_1$–$C_{20}$-hydrocarbon group, eg. a $C_1$–$C_{10}$-alkyl group or $C_6$–$C_{14}$-aryl group which may bear one or more identical or different halogen, OH, $OR^2$, $SR^2$, $NR^2_2$—, $PR^2_2$—, —$SiR^2_3$ or —$OSiR^2_3$ substituents, or two radicals $R^2$ may be joined to form a ring system, or $Y^7$ and $Y^8$ are each a $C_1$–$C_{20}$-heterocyclic group which is bound via a carbon atom and may in turn bear $C_1$–$C_{20}$-radicals or heteroatoms as substituents, and in formula III, at least one of the radicals $Y^7$ and $Y^8$, preferably $Y^7$, is a hydrogen atom and $Y^9$ is a hydrogen atom.

Particular preference is given to indanones of the formula III in which

X' is chlorine, bromine, iodine, triflate, nonaflate, mesylate, ethylsulfonate, benzenesulfonate, tosylate, triisopropylbenzenesulfonate, formate, acetate, trifluoroacetate, nitrobenzoate, halogenated arylcarboxylates, in particular fluorinated benzoate, methyl carbonate, ethyl carbonate, benzyl carbonate, tert-butyl carbonate, dimethyl phosphonate, diethyl phosphonate, diphenyl phosphonate or diazonium, $R^{1'}$ is a linear, branched or cyclic $C_1$–$C_8$-alkyl group which may bear one or more identical or different fluorine, chlorine, $OR^2$, —$SiR^2_3$ or —$OSiR^2_3$ substituents, a $C_6$–$C_{10}$-aryl group which may bear one or more identical or different fluorine, chlorine, $OR^2$, $SR^2$, —$SiR^2_3$ or —$OSiR^2_3$ substituents, a $C_7$–$C_{12}$-alkylaryl or arylalkyl group, where the alkyl part may bear one or more identical or different fluorine, chlorine, $OR^2$, $SR^2$, —$SiR^2_3$ or —$OSiR^2_3$ substituents and the aryl part may bear one or more identical or different fluorine, chlorine, $OR^2$, $SR^2$, —$SiR^2_3$ or —$OSiR^2_3$ substituents, a $C_2$–$C_8$-alkenyl group, $C_2$–$C_8$-alkynyl group, a $C_8$–$C_{12}$-arylalkenyl group, an $OR^2$, —$SiR^2_3$ or —$OSiR^2_3$ group, where $R^2$ are identical or different and are each a $C_1$–$C_4$-alkyl or $C_6$–$C_{10}$-aryl group, or $R^{1'}$ is a $C_1$–$C_{20}$-heterocyclic group, where preferred heteroatoms are oxygen and sulfur, which may in turn bear $C_1$–$C_{20}$-hydrocarbon radicals as substituents.

Very particular preference is given to indanones of the formula III in which

X' is chlorine, bromine, iodine, triflate or mesylate, $R^{1'}$ is a linear, branched or cyclic $C_1$–$C_8$-alkyl group which may bear one or more fluorine substituents, a $C_6$-aryl group which may bear one or more identical or different fluorine, chlorine or $OR^2$ substituents, a $C_7$–$C_{10}$-alkylaryl or arylalkyl group, where the alkyl part may bear one or more identical or different fluorine, chlorine or $OR^2$ substituents and the aryl part may bear one or more identical or different fluorine, chlorine or $OR^2$ substituents, a $C_2$–$C_8$-alkenyl group or $C_2$–$C_8$-alkynyl group which may each bear one or more identical or different fluorine or $OR^2$ substituents, a $C_8$–$C_{12}$-arylalkenyl group, an $OR^2$, $SiR^2_3$ or —$OSiR^2_3$ group, where $R^2$ are identical or different and are each a $C_1$–$C_4$-alkyl or $C_6$-aryl group, or $R^{1'}$ is a $C_1$–$C_{16}$-heterocyclic group, where preferred heteroatoms are oxygen and sulfur, and $Y^7$ is a hydrogen atom and $Y^8$ is a hydrogen atom or is as defined for X' or $Y^8$ is a linear, branched or cyclic $C_2$–$C_6$-alkyl group which may bear one or more fluorine substituents, a $C_6$–$C_{10}$-aryl group which may bear one or more fluorine substituents, a $C_7$–$C_{12}$-alkylaryl group or $C_7$–$C_{12}$-arylalkyl group, where the alkyl part may bear one or more fluorine substituents and the aryl part may bear one or more fluorine substituents, a $C_2$–$C_8$-alkenyl group, a $C_2$–$C_8$-alkynyl group, a $C_8$–$C_{10}$-arylalkenyl group or $Y^8$ is a $C_1$–$C_9$-heterocyclic group which is bound via a carbon atom and may in turn bear $C_1$–$C_6$-radicals or heteroatoms as substituents; preferably, $Y^8$ is as defined for X' or is a $C_6$–$C_{14}$-aryl group.

Extraordinary preference is given to indanones of the formula III in which

X' is chlorine, bromine or triflate,
$R^{1'}$ is a linear, branched or cyclic $C_1$–$C_6$-alkyl group, a $C_7$–$C_{10}$-alkylaryl or arylalkyl group, a $C_2$–$C_6$-alkenyl group or $C_2$–$C_6$-alkynyl group or a $C_8$–$C_{10}$-arylalkenyl group and
$Y^7$, $Y^8$ and $Y^9$ are each a hydrogen atom.

Illustrative examples of indanones of the formula III, which do not, however, restrict the scope of the invention, are:

2-methyl-7-chloro-1-indanone 2-methyl-7-bromo-1-indanone 2-methyl-7-iodo-1-indanone 2-methyl-7-trifluoroacetoxy-1-indanone 2-methyl-7-trifluoromethanesulfonoxy-1-indanone 2-methyl-7-methanesulfonoxy-1-indanone 2-methyl-7-ethanesulfonoxy-1-indanone 2-methyl-7-(p-toluenesulfonoxy)-1-indanone 2-methyl-7-bezenesulfonoxy)-1-indanone 2-methyl-7-(2,4,6-triisopropylbenzenesulfonoxy)-1-indanone 2-methyl-7-pentafluorobenzenesulfonoxy-1-indanone 2-methyl-7-nonafluorobutanesulfonoxy-1-indanone 2-methyl-7-acetoxy-1-indanone 2-methyl-7-formyloxy-1-indanone 2-methyl-7-pentafluorobenzoyloxy-1-indanone 2-methyl-7-(p-nitrobenzoyloxy)-1-indanone 2-methyl-7-methoxycarbonyloxy-1-indanone 2-methyl-7-tert-butyloxycarbonyloxy-1-indanone 2-methyl-7-ethoxycarbonyloxy-1-indanone 2-methyl-7-benzyloxycarbonyloxy-1-indanone 2-methyl-7-dimethylphosphonoxy-1-indanone 2-methyl-7-diethylphosphonoxy-1-indanone 2-methyl-7-diphenylphosphonoxy-1-indanone 2-methyl-7-diazonium-1-indanone chloride 2-methyl-7-diazonium-1-indanone tetrafluoroborate 2-methyl-7-diazonium-1-indanone sulfate 2-methyl-5-butyl-7-bromo-1-indanone 2-methyl-5-fluoro-7-bromo-1-indanone 2-methyl-5,7-dibromo-1-indanone 2-methyl-5,7-dichloro-1-indanone 2-methyl-6,7-dichloro-1-indanone 2-methyl-5-chloro-7-bromo-1-indanone 2,6-dimethyl-7-chloro-1-indanone 2-methyl-5-butyl-7-chloro-1-indanone 2-methyl-5-isopropyl-7-trifluoromethanesulfonoxy-1-indanone 2-methyl-5-tert-butyl-7-methanesulfonoxy-1-indanone 2-methyl-5-phenyl-7-bromo-1-indanone 2-methyl-5-(3,5-dimethoxyphenyl)-7-iodo-1-indanone 2-methyl-5-benzyl-7-chloro-1-indanone 2-methyl-5-vinyl-7-(p-toluenesulfonoxy)-1-indanone 2-methyl-6-bromo-7-trifluoroacetoxy-1-indanone 2-methyl-6-phenyl-7-bromo-1-indanone 2-trifluoromethyl-7-chloro-1-indanone 2-trifluoromethyl-7-bromo-1-indanone 2-trifluoromethyl-5-isobutyl-7-trifluoromethanesulfonoxy-1-indanone 2-ethyl-7-chloro-1-indanone 2-ethyl-7-bromo-1-indanone 2-ethyl-7-diazonium-1-indanone tetrafluoroborate 2-ethyl-7-methanesulfonoxy-1-indanone 2-ethyl-5-methyl-7-bromo-1-indanone 2-ethyl-7-diazonium-1-indanone tetrafluoroborate 2,6-diethyl-7-diazonium-1-indanone chloride 2-butyl-7-chloro-1-indanone 2-butyl-5-fluoro-7-chloro-1-indanone 2-n-propyl-7-chloro-1-indanone 2-n-propyl-7-bromo-1-indanone 2-butyl-5,7-dichloro-1-indanone 2-isopropyl-7-chloro-1-indanone 2-isopropyl-7-bromo-1-indanone 2-isopropyl-7-iodo-1-indanone 2-isopropyl-5-diphenylphosphino-7-nonafluorobutanesulfonoxy-1-indanone 2-phenyl-7-chloro-1-indanone 2-(2-pyridyl)-7-bromo-1-indanone 2-(2-furyl)-7-iodo-1-indanone 2-cyclohexyl-7-chloro-1-indanone 2-cyclohexyl-7-bromo-1-indanone 2-cyclohexyl-7-trifluoromethanesulfonoxy-1-indanone 2-isobutyl-7-chloro-1-indanone 2-isobutyl-7-bromo-1-indanone 2-tert-butyl-7-chloro-1-indanone 2-tert-butyl-7-iodo-1-indanone 2-benzyl-7-chloro-1-indanone 2-allyl-7-chloro-1-indanone 2-vinyl-7-trifluoromethanesulfonoxy-1-indanone 2-(2-trimethylsilylethyn-1-yl)-6-benzyl-7-chloroindanone 2-(hex-1-ynyl)-7-trifluoromethanesulfonoxy-1-indanone 2-trimethylsilyl-7-bromo-1-indanone 2-trimethylsilyloxy-7-bromo-1-indanone 2-dimethylamino-7-trifluoromethanesulfonoxy-1-indanone 2-N-pyrrolidino-7-chloro-1-indanone 2-diphenylphosphino-5-isopropyl-7-bromo-1-indanone 2-methoxy-6-allyl-7-chloro-1-indanone 2,6-dimethoxy-7-bromo-1-indanone 2-phenoxy-5-dimethylamino-7-trifluoromethanesulfonoxy-1-indanone 2-(2-methoxyethyl)-7-chloro-1-indanone 2-(3-chloropropyl)-7-chloro-1-indanone The indanones of the formula I or Ia can be prepared by methods similar to those known from the literature (eg. U.S. Pat. No. 5,489,712; U.S. Pat. No. 4,070,539; S. J. desolms et al., J. Med. Chem., 1978, 21, 437). To prepare indanones of the formula I, for example, an aryl alkyl ketone of the formula (A) can be methylenated and subsequently. subjected to a Nazarov cyclization.

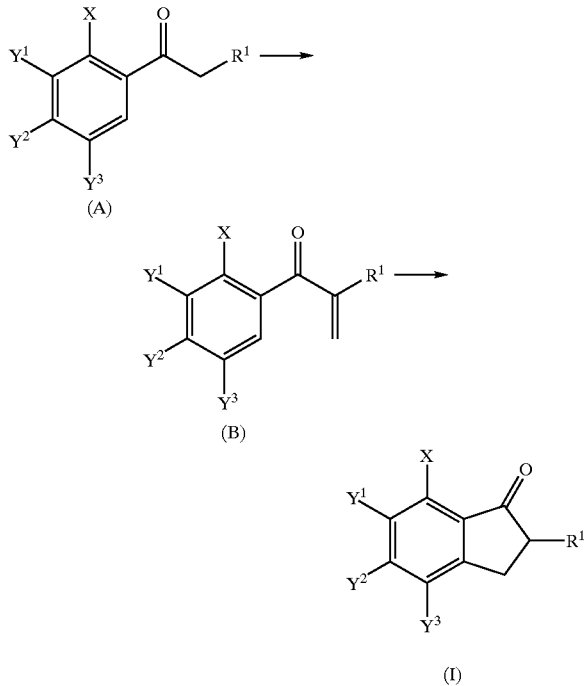

$R^1$, X, $Y^1$, $Y^2$ and $Y^3$ in the formulae A, B and I are as defined: above for formula I.

In the case of an aryl alkyl ketone, the methylene group can, for example, be introduced by an aldol condensation with formaldehyde as methylene source or by a Mannich reaction, in which, for example, N,N,N',N'-tetramethyldiaminomethane, Eschenmoser's salt or urotropien/acetic anhydride can be used as methylene source. It is indicated in the literature (U.S. Pat. No. 5,489,712) that the aldol condensation of formaldehyde, which is the most inexpensive methylene source, and aryl alkyl ketones proceeds in poor yields and the management of the reaction is said to be complicated. M. M. Curzu et al. in Synthesis (1984) 339 state that in the aldol condensation of formaldehyde and certain aryl alkyl ketones, considerable amounts of starting material remain unreacted and undesirable by-products such as the primary aldol product containing a hydroxymethyl group are present in the end product.

It has surprisingly been found that the aldol condensation (ie. the introduction of the methylene group) of aryl alkyl ketones proceeds virtually quantitatively under basic conditions using formaldehyde, and the primary aldol product containing a hydroxymethyl group cannot be observed spectroscopically. Here, preferred aryl alkyl ketones of the formula A are those in which X is a halogen.

The aldol condensation is carried out using a formaldehyde source, preferably aqueous formalin solution, and a base, preferably an alkali metal carbonate or alkaline earth metal carbonate or an alkali metal hydroxide or alkaline earth metal hydroxide, particularly preferably an aqueous sodium hydroxide solution, at 0–100° C., preferably 20–60° C.

The molar ratio of base to aryl alkyl ketone is in the range from 0.01 to 5, preferably in the range from 0.1 to 2.

The molar ratio of formaldehyde to aryl alkyl ketone is in the range from 0.5 to 1.5, preferably in the range from 0.9 to 1.2. The concentration of the aryl alkyl ketone in the reaction mixture (total volume) is in the range from 0.01 to 6 mol/l, preferably from 0.1 to 2 mol/l. The aryl alkyl ketone can be diluted with inert solvents such as ethers, hydrocarbons or halogenated hydrocarbons. The reaction can be carried out in a single-phase or multiphase system.

In the case of multiphase reaction mixtures, phase transfer catalysts can be added to accelerate the reaction.

The reaction time is usually from 15 minutes to 12 hours or longer.

The reaction can also be carried out in an inert gas atmosphere and the pressure in the reaction vessel can be either below or above atmospheric pressure.

The subsequent cyclization to form the indanone is carried out by literature methods (J. H. Burckhalter, R. C. Fuson, J. Amer. Chem. Soc., 1948, 70, 4184; E. D. Thorsett, F. R. Stermitz, Synth. Commun., 1972, 2, 375; Synth. Commun., A. Bhattacharya, B. Segmuller, A. Ybarra, 1996, 26, 1775; U.S. Pat. No. 5,489,712). The cyclization is preferably carried out under acid conditions. As cyclization reagent, it is possible to use acids such as protic acids (eg. sulfuric acid, polyphosphoric acid, methanesulfonic acid) or Lewis acids (eg. aluminum trichloride, boron trifluoride). The reaction product from the aldol condensation can be diluted with an inert solvent before addition to the cyclization reagent, or can be added in undiluted form.

To prepare indanones of the formula I and Ia in which X is an oxygen-containing leaving group, for example a triflate group, the starting materials used are preferably hydroxyindanones, some of which are known from the literature (eg. Bringmann et al., Liebigs Ann. Chem., 1985, 2116–2125), and the hydroxy group is converted by literature methods into an oxygen-containing leaving group X, eg. triflate (eg.: P. J. Stang, Synthesis, 1982, 85; V. Percec, J. Org. Chem., 1995, 60, 176; Autorenkollektiv, Organikum, VEB Deutscher Verlag der Wissenschaften, 1976).

Some of the aryl alkyl ketones are known from the literature or they can easily be prepared by literature methods (eg.: R. C. Larock, Comprehensive Organic Transformations, VCH, 1989).

The invention further provides substituted indanones of the formula IV

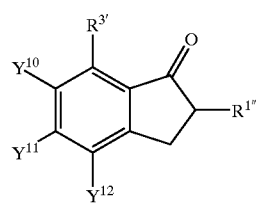

(IV)

where

R$^{1''}$ is a $C_1$–$C_{40}$-group such as a $C_1$–$C_{40}$-hydrocarbon group which is bound via a carbon atom and may bear one or more identical or different heteroatom-containing radicals as substituents, eg. a linear, branched or cyclic $C_1$–$C_{20}$-alkyl group which may bear one or more identical or different halogen, OH, OR$^2$, SR$^2$NR$^2_2$—, PR$^2_2$—, —SiR$^2_3$ or —OSiR$^2_3$ substituents, a $C_6$–$C_{22}$-aryl group which may bear one or more identical or different halogen, OH, OR$^2$, SR$^2$NR$^2_2$—, PR$^2_2$—, —SiR$^2_3$ or —OSiR$^2_3$ substituents, a $C_7$–$C_{20}$-alkylaryl group or a $C_7$–$C_{20}$-arylalkyl group, where the alkyl part may bear one or more identical or different halogen, OH, OR$^2$, SR$^2$NR$^2_2$—, PR$^2_2$—, —SiR$^2_3$ or —OSiR$^2_3$ substituents and the aryl part may bear one or more identical or different halogen, OH, OR$^2$, SR$^2$, NR$^2_2$—, PR$^2_2$—, —SiR$^2_3$ or —OSiR$^2_3$ substituents, a $C_2$–$C_{10}$-alkenyl group which may bear one or more identical or different halogen, OH, OR$^2$, SR$^2$NR$^2_2$—, PR$^2_2$—, —SiR$^2_3$ or —OSiR$^2_3$ substituents, a $C_2$–$C_{20}$-alkynyl group which may bear one or more identical or different halogen, OH, OR$^2$, SR$^2$NR$^2_2$—, PR$^2_2$—, —SiR$^2_3$ or —OSiR$^2_3$ substituents, a $C_8$–$C_{12}$-arylalkenyl group, where the alkenyl part may bear one or more identical or different halogen, OH, OR$^2$, SR$^2$NR$^2_2$—, PR$^2_2$—, —SiR$^2_3$ or —OSiR$^2_3$ substituents and the aryl part may bear one or more identical or different halogen, OH, OR$^2$, SR$^2$NR$^2_2$—, PR$^2_2$—, —SiR$^2_3$ or —OSiR$^2_3$ substituents, or R$^{1''}$ is an OR$^2$, SR$^2$, NR$^2_2$, PR$^2_2$, SiR$^2_3$ or OSiR$^2_3$ group, where R$^2$ are identical or different and are each a $C_1$–$C_{20}$-hydrocarbon group such as a $C_1$–$C_{10}$-alkyl or $C_6$–$C_{14}$-aryl group which may each bear one or more identical or different halogen, OH, OR$^2$, SR$^2$NR$^2_2$—, PR$^2_2$—, —SiR$^2_3$ or —OSiR$^2_3$ substituents, or two radicals R$^2$ may be joined to form a ring system, or R$^{1''}$ is a $C_1$–$C_{20}$-heterocyclic group which is bound via a carbon atom and may in turn bear $C_1$–$C_{20}$-radicals or heteroatoms as substituents, R$^{3'}$ is an unsaturated $C_2$–$C_{40}$-group such as an unsaturated $C_2$–$C_{40}$-hydrocarbon group which is bound via a carbon atom and may bear one or more identical or different heteroatom-containing radicals as substituents, eg. a $C_6$–$C_{22}$-aryl group which may bear one or more identical or different halogen, OR$^2$, SR$^2$NR$^2_2$—, NH$_2$, —N$_2$H$_3$, NO$_2$, CN, CO$_2$R$^2$, CHO, COR$^2$, PR$^2_2$—, —SiR$^2_3$ or —OSiR$^2_3$ substituents, a $C_7$–$C_{15}$-alkylaryl group or $C_7$–$C_{15}$-arylalkyl group, where the alkyl part may bear one or more identical or different halogen, OH, OR$^2$, SR$^2$NR$^2_2$—, PR$^2_2$—, —SiR$^2_3$ or —OSiR$^2_3$ substituents and the aryl part may bear one or more identical or different halogen, OR$^2$, SR$^2$NR$^2_2$—, NH$_2$, —N$_2$H$_3$, NO$_2$, CN, CO$_2$R$^2$, CHO, PR$^2_2$—, —SiR$^2_3$ or —OSiR$^2_3$ substituents, a $C_2$–$C_{10}$-alkenyl group which may bear one or more identical or different halogen, OH, $OR^2$, $CO_2R^2$, $COR^2$, $SR^2$, $NR^2_2$—, $PR^2_2$—, —$SiR^2_3$ or —$OSiR^2_3$ substituents, a $C_2$–$C_{10}$-alkynyl group which may bear one or more identical or different halogen, OH, $OR^2$, $SR^2$, $NR^2_2$—, $PR^2_2$—, —$SiR^2_3$ or —$OSiR^2_3$ substituents, a $C_8$–$C_{12}$-arylalkenyl group, which may bear one or more identical or different halogen, OH, $OR^2$, $CO_2R^2$, $COR^2$, $SR^2$, $NR^2_2$, $PR^2_2$—, —$SiR^2_3$ or —$OSiR^2_3$ substituents, or $R^{3\prime}$ is fluorine, a $PR^2_2$, $B(OR^2)_2$, $SiR^2_3$ or $SnR^2_3$ group, where $R^2$ are identical or different and are each a $C_1$–$C_{20}$-hydrocarbon group, eg. a $C_1$–$C_{10}$-alkyl group or $C_6$–$C_{14}$-aryl group which may each bear one or more identical or different halogen, OH, $OR^2$, $SR^2NR^2_2$—, $PR^2_2$—, —$SiR^2_3$ or —$OSiR^2_3$ substituents, or two radicals $R^2$ may be joined to form a ring system, or $R^{3\prime}$ is a $C_1$–$C_{20}$-heterocyclic group which is bound via a carbon atom and may in turn bear $C_1$–$C_{20}$-radicals or heteroatoms as substituents, and $Y^{10}$ and $Y^{11}$ are identical or different and are each a hydrogen atom or are as defined for $R^3$ in formula II, ie. are a $C_1$–$C_{40}$-hydrocarbon group which is bound via a carbon atom and may bear one or more identical or different heteroatom-containing radicals as substituents, eg. a linear, branched or cyclic $C_1$–$C_{20}$-alkyl group which may bear one or more identical or different halogen, OH, $OR^2$, $SR^2$, $NR^2_2$—, $PR^2_2$—, —$SiR^2_3$ or —$OSiR^2_3$ substituents, a $C_6$–$C_{22}$-aryl group which may bear one or more identical or different halogen, $OR^2$, $SR^2NR^2_2$—, $NH_2$, —$N_2H_3$, $NO_2$, CN, $CO_2R^2$, CHO, $COR^2$, $PR^2_2$—, —$SiR^2_3$ or —$OSiR^2_3$ substituents, a $C_7$–$C_{15}$-alkylaryl group or $C_7$–$C_{15}$-arylalkyl group, where the alkyl part may bear one or more identical or different halogen, OH, $OR^2$, $SR^2NR^2_2$—, $PR^2_2$—, —$SiR^2_3$ or —$OSiR^2_3$ substituents and the aryl part may bear one or more identical or different halogen, $OR^2$, $SR^2NR^2_2$—, $NH_2$, —$N_2H_3$, $NO_2$, CN, $CO_2R^2$, CHO, $PR^2_2$—, —$SiR^2_3$ CHO, $PR^2_2$—or —$OSiR^2_3$ substituents, a $C_2$–$C_{10}$-alkenyl group which may bear one or more identical or different halogen, OH, $OR^2$, $SR^2$, $NR^2_2$—, $PR^2_2$—, —$SiR^2_3$ or —$OSiR^2_3$ substituents, a $C_2$–$C_{10}$-alkynyl group which may bear one or more identical or different halogen, OH, $OR^2$, $SR^2$, $NR^2_2$—, $PR^2_2$—, —$SiR^2_3$ or —$OSiR^2_3$ substituents, a $C_8$–$C_{12}$-arylalkenyl group, which may bear one or more identical or different halogen, OH, $OR^2$, $CO_2R^2$, $COR^2$, $SR^2$, $NR^2_2$—, $PR^2_2$—, —$SiR^2_3$ or —$OSiR^2_3$ substituents, or $Y^{10}$ or $Y^{11}$ are a halogen atom, a $PR^2_2$, $B(OR^2)_2$, $SiR^2_3$ or $SnR^2_3$ group, where $R^2$ are identical or different and are each a $C_1$–$C_{20}$-hydrocarbon group, eg. a $C_1$–$C_{10}$-alkyl group or $C_6$–$C_{14}$-aryl group which may each bear one or more identical or different halogen, OH, $OR^2$, $SR^2NR^2_2$—, $PR^2_2$—, —$SiR^2_3$ or —$OSiR^2_3$ substituents, or two radicals $R^2$ may be joined to form a ring system, or $Y^{10}$ or $Y^{11}$ are each a $C_1$–$C_{20}$-heterocyclic group which is bound via a carbon atom and may in turn bear $C_1$–$C_{20}$-radicals or heteroatoms as substituents;

in formula IV, at least one of the radicals $Y^{10}$ and $Y^{11}$, preferably $Y^{10}$, is a hydrogen atom and $Y^{12}$ is a hydrogen atom.

Preference is given to indanones of the formula IV in which $R^1$ is a linear, branched or cyclic $C_1$–$C_8$-alkyl group which may bear ,one or more identical or different fluorine, chlorine, $OR^2$, $PR^2_2$—, $NR^2_2$—, —$SiR^2_3$ or —$OSiR^2_3$ substituents, a $C_6$–$C_{10}$-aryl group which may bear one or more identical or different fluorine, chlorine, $OR^2$, $SR^2$, $NR^2_2$—, $PR^2_2$—, —$SiR^2_3$ or —$OSiR^2_3$ substituents, a $C_7$–$C_{12}$-alkylaryl or arylalkyl group, where the alkyl part may bear one or more identical or different fluorine, chlorine, $OR^2$, $SR^2$, $NR^2_2$—, $PR^2_2$—, —$SiR^2_3$ or —$OSiR^2_3$ substituents and the aryl part may bear one or more identical or different fluorine, chlorine, $OR^2$, $SR^2NR^2_2$—, $PR^2_2$—, —$SiR^2_3$ or —$OSiR^2_3$ substituents, a $C_2$–$C_6$-alkenyl group, $C_2$–$C_6$-alkynyl group, a $C_8$–$C_{12}$-arylalkenyl group, an $OR^2$, $PR^2_2$—, $NR^2_2$—, —$SiR^2_3$ or —$OSiR^2_3$ group where $R^2$ are identical or different and are each a $C_1$–$C_4$-alkyl or $C_6$–$C_{10}$-aryl group, where the alkyl group may bear one or more identical or different fluorine, chlorine, $OR^2$, $SR^2$, $NR^2_2$—, $PR^2_2$—, —$SiR^2_3$ or —$OSiR^2_3$ substituents and the aryl group may bear 1–3 substituents such as fluorine, chlorine, $OR^2$, $SR^2$, $NR^2_2$—, $PR^2_2$—, —$SiR^2_3$ or —$OSiR^2_3$, or a $C_1$–$C_{20}$-heterocyclic group, where preferred heteroatoms are oxygen, nitrogen, sulfur, phosphorus and silicon, which may in turn bear $C_1$–$C_{10}$ radicals or heteroatoms as substituents, and $R^{3\prime}$ is an unsaturated $C_2$–$C_{20}$-group, a $C_6$–$C_{14}$-aryl group which may each bear one or more identical or different fluorine, chlorine, $OR^2$, $SR^2$, $NR^2$, $NH_2$, —$N_2H_3$, $NO_2$, CN, $CO_2R^2$, $COR^2$, CHO, $PR^2_2$—, —$SiR^2_3$ or —$OSiR^2_3$ substituents, a $C_7$–$C_{15}$-alkylaryl group or $C_7$–$C_{15}$-arylalkyl group, where the alkyl part may bear one or more identical or different fluorine, chlorine, $OR^2$, $CO_2R^2$, $COR^2$, $NR^2_2$— or —$OSiR^2_3$ substituents and the aryl part may bear one or more identical or different fluorine, chlorine, $OR^2$, $SR^2$, $NR^2_2$—, $NH_2$, —$N_2H_3$, $NO_2$, CN, $CO_2R^2$, $COR^2$, CHO, $PR^2_2$—, —$SiR^2_3$ or —$OSiR^2_3$ substituents, a $C_2$–$C_{10}$-alkenyl group which may bear one or more identical or different fluorine, chlorine, $OR^2$, $CO_2R^2$, $COR^2$, $NR^2_2$— or —$OSiR^2_3$ substituents, a $C_2$–$C_{10}$-alkynyl group which may bear one or more identical or different fluorine, chlorine, $OR^2$, $CO_2R^2$, $CONR^2_2$— or —$OSiR^2_3$ substituents, a $C_8$–$C_{12}$-arylalkenyl group which may bear one or more identical or different fluorine, chlorine, $CO_2R^2$, $COR^2$, $OR^2$, $NR^2_2$— or —$OSiR^2_3$ substituents, a $PR^2_2$, $B(OR^2)_2$, $SiR^2_3$ or $SnR^2_3$ group where $R^2$ are identical or different and are each a $C_1$–$C_4$-alkyl or $C_6$–$C_{10}$-aryl group, where the alkyl group may bear one or more identical or different fluorine, chlorine, $OR^2$, $SR^2$, $NR^2_2$—, $PR^2_2$—, —$SiR^2_3$ or —$OSiR^2_3$ substituents and the aryl group may bear one or more identical or different fluorine, chlorine, $OR^2$, $SR^2$, $NR^2_2$—, $PR^2_2$—, —$SiR^2_3$ or —$OSiR^2_3$ substituents, and, in addition, two radicals $R^2$ may be joined to one another to form a ring system, a $C_2$–$C_{20}$-heterocyclic group, where preferred heteroatoms are oxygen, nitrogen, sulfur, phosphorus and silicon, which may in turn bear $C_1$–$C_{10}$ radicals or heteroatoms as substituents.

Particular preference is given to indanones of the formula IV in which $R^{1\prime\prime}$ is a linear, branched or cyclic $C_1$–$C_8$-alkyl group which may bear one or more identical or different fluorine, chlorine, $OR^2$ or $NR^2_2$ substituents, a $C_6$–$C_{10}$-aryl group which may bear one or more identical or different fluorine, chlorine, $OR^2$ or $NR^2_2$ substituents, a $C_7$–$C_{12}$-alkylaryl or arylalkyl group, where the alkyl part may bear one or more identical or different fluorine, chlorine, $OR^2$ or $NR^2_2$ substituents and the aryl part may bear fluorine, chlorine, $OR^2$ or $NR^2_2$ substituents, a $C_2$–$C_8$-alkenyl group or $C_2$–$C_8$-alkynyl group which may each bear one or more identical or different fluorine, chlorine, $OR^2$ or $NR^2_2$ substituents, a $C_8$–$C_{12}$-arylalkenyl group which may bear one or more identical or different fluorine, chlorine, $OR^2$ or $NR^2_2$ substituents, a $OR^2$, $SiR^2_3$ or —$OSiR^2_3$ group, where $R^2$ are identical or different and are each a $C_1$–$C_4$-alkyl or phenyl group, where the alkyl group may bear one or more identical or different fluorine, chlorine, $OR^2$ or $NR^2_2$ substituents and the aryl group may bear fluorine, chlorine, $OR^2$ or $NR^2_2$ substituents, a $C_2$–$C_{16}$-heterocyclic group, where preferred heteroatoms are oxygen, nitrogen, sulfur and silicon, which may in turn bear $C_1$–$C_{10}$-radicals or heteroatoms as substituents, and $R^{3'}$ is an unsaturated $C_2$–$C_{20}$-group such as a $C_6$–$C_{14}$-aryl group which may bear fluorine, chlorine, $OR^2$, $SR^2$, $NR^2_2$, $NH_2$, $NO_2$, $CN$, $COR^2$ or $CO_2R^2$ substituents, a $C_7$–$C_{15}$-alkylaryl group or $C_7$–$C_{15}$-arylalkyl group, where the alkyl part may bear one or more identical or different fluorine, $OR^2$, $NR^2_2$— or —$OSiR^2_3$ substituents and the aryl part may bear fluorine, chlorine, $OR^2$, $SR^2$, $NR^2_2$—, $NH_2$, $NO_2$, $CN$, $COR^2$ or $CO_2R^2$ substituents, a $C_2$–$C_{10}$-alkenyl group which may bear one or more identical or different fluorine, $OR^2$, $CO_2R^2$, $COR^2$, $NR^2_2$—or —$OSiR^2_3$ substituents, a $C_2$–$C_{10}$-alkynyl group which may bear one or more identical or different fluorine, $OR^2$, $NR^2_2$—or -$OSiR^2_3$ substituents, a $C_8$–$C_{12}$-arylalkenyl group, a $PR^2_2$, $B(OR^2)_2$ or $SnR^2_3$ group, where $R^2$ are identical or different and are each a $C_1$–$C_4$-alkyl or $C_6$-aryl group, where the alkyl group may bear one or more identical or different fluorine, chlorine, $OR^2$ or $NR^2_2$ substituents and the aryl group may bear fluorine, chlorine, $OR^2$ or $NR^2_2$ substituents, and, in addition, two radicals $R^2$ may be joined to one another to form a ring system, a $C_1$–$C_{14}$-heterocyclic group, where preferred heteroatoms are oxygen, nitrogen or sulfur which may in turn bear $C_1$–$C_6$-radicals or heteroatoms as substituents.

Very particular preference is given to indanones of the formula IV in which $R^{1'''}$ is a linear, branched or cyclic $C_1$–$C_8$-alkyl group which may bear one or more identical or different fluorine, $OR^2$ or $NR^2_2$ substituents, a $C_6$-aryl group which may bear fluorine, $OR^2$ or $NR^2_2$ substituents, a $C_7$–$C_{10}$-alkylaryl or arylalkyl group, which may each bear fluorine, chlorine, $OR^2$ or $NR^2_2$ substituents, a $C_2$–$C_8$-alkenyl group, a $C_2$–$C_8$-alkynyl group which may bear fluorine, $OR^2$ or $NR^2_2$ substituents, a $C_8$–$C_{10}$-arylalkenyl group which may bear fluorine, $OR^2$ or $NR^2_2$ substituents, an $OR^2$, $SiR^2_3$ or —$OSiR^2_3$ group, where $R^2$ are identical or different and are each a $C_1$–$C_4$-alkyl or phenyl group which may bear fluorine, chlorine, $OR^{2a}$ or $NR^{2a}_2$ substituents, a $C_2$–$C_9$-heterocyclic group, where preferred heteroatoms are oxygen, nitrogen and sulfur, which may in turn bear $C_1$–$C_6$-hydrocarbon radicals or heteroatoms as substituents, and $R^{3'}$ is an unsaturated $C_2$–$C_{14}$-group such as a $C_6$–$C_{14}$-aryl group which may bear fluorine, chlorine, $R^2$, $OR^{2a}$ or $NR^{2a}_2$ substituents, a $C_7$–$C_{10}$-alkylaryl group or $C_7$–$C_{10}$-arylalkyl group, where the alkyl part may bear one or more identical or different fluorine, $OR^{2a}$, $NR^{2a}_2$ or —$OSiR^{2a}_3$ substituents and the aryl part may bear one or: more identical or different fluorine, chlorine, $OR^{2a}$ or $NR^{2a}_2$ substituents, a $C_2$–$C_8$-alkenyl group which may bear one or more identical or different fluorine, $OR^{2a}$, $CO_2R^{2a}$ or $NR^{2a}_2$ substituents, a $C_2$–$C_8$-alkynyl group which may bear one or more identical or different fluorine, $OR^{2a}$ or $NR^{2a}_2$ substituents, a $C_8$–$C_{12}$-arylalkenyl group, a $PR^{2a}_2$, $B(OR^{2a})_2$ or $SnR^{2a}_3$ group, where $R^{2a}$ are identical or different and are each a linear or branched $C_1$–$C_4$-alkyl group which may bear one or more fluorine substituents or a phenyl group which may bear one or more identical or different fluorine or $OR^{2a}$ substituents, and, in addition, two radicals $R^{2a}$ may be joined to one another to form a ring system, a $C_1$–$C_{14}$-heterocyclic group ,where preferred heteroatoms are oxygen, nitrogen or sulfur, which may in turn bear $C_1$–$C_4$-radicals or heteroatoms as substituents, and $Y^{10}$, $Y^{11}$ and $Y^{12}$ are each a hydrogen atom.

Illustrative examples of indanones of the formula IV, which do not, however, restrict the scope of the invention, are:

2-methyl-7-phenyl-1-indanone 2-methyl-7-(1-naphthyl)-1-indanone 2-methyl-7-(2-naphthyl)-1-indanone 2-methyl-7-(2-methyl-1-naphthyl)-1-indanone 2-methyl-7-(4-methyl-1-naphthyl)-1-indanone 2-methyl-7-(4-methoxy-1-naphthyl)-1-indanone 2-methyl-7-(6-methoxy-2-naphthyl)-1-indanone 2-methyl-7-(4-methylphenyl)-1-indanone 2-methyl-7-(3-methylphenyl)-1-indanone 2-methyl-7-(2-methylphenyl)-1-indanone 2-methyl-7-(3,5-dimethylphenyl)-1-indanone 2-methyl-7-(2,3-dimethylphenyl)-1-indanone 2-methyl-7-(2,4-dimethylphenyl)-1-indanone 2-methyl-7-(2,5-dimethylphenyl)-1-indanone 2-methyl-7-(3-butylphenyl)-1-indanone 2-methyl-7-(4-tert-butylphenyl)-1-indanone 2-methyl-7-mesityl-1-indanone 2-methyl-7-(4-biphenyl)-1-indanone 2-methyl-7-(3-biphenyl)-1-indanone 2-methyl-7-(2-biphenyl)-1-indanone 2-methyl-7-(3,5-diphenylphenyl)-1-indanone 2-methyl-7-(4-styryl)-1-indanone 2-methyl-7-(3-styryl)-1-indanone 2-methyl-7-(2-styryl)-1-indanone 2-methyl-7-(9-anthracenyl)-1-indanone 2-methyl-7-(9-phenanthrenyl)-1-indanone 2-methyl-7-(2-hydroxyphenyl)-1-indanone 2-methyl-7-(4-hydroxyphenyl)-1-indanone 2-methyl-7-(3-hydroxyphenyl)-1-indanone 2-methyl-7-(2,4-dihydroxyphenyl)-1-indanone 2-methyl-7-(3,5-dihydroxyphenyl)-1-indanone 2-methyl-7-(4-methoxyphenyl)-1-indanone 2-methyl-7-(3-methoxyphenyl)-1-indanone 2-methyl-7-(2-methoxyphenyl)-1-indanone 2-methyl-7-(2,4-dimethoxyphenyl)-1-indanone 2-methyl-7-(3,5-dimethoxyphenyl)-1-indanone 2-methyl-7-(3,4,5-trimethoxyphenyl)-1-indanone 2-methyl-7-(4-phenoxyphenyl)-1-indanone 2-methyl-7-(3,4-methylenedioxy)phenyl)-1-indanone 2-methyl-7-(4-thioanisyl)-1-indanone 2-methyl-7-(3-thioanisyl)-1-indanone 2-methyl-7-(4-nitrophenyl)-1-indanone 2-methyl-7-(3-nitrophenyl)-1-indanone 2-methyl-7-(2-nitrophenyl)-1-indanone 2-methyl-7-(4-methyl-3-nitrophenyl)-1-indanone 2-methyl-7-(4-methoxycarbonylphenyl)-1-indanone 2-methyl-7-(3-methoxycarbonylphenyl)-1-indanone 2-methyl-7-(2-methoxycarbonylphenyl)-1-indanone 2-methyl-7-(4- carboxylphenyl)-1-indanone 2-methyl-7-(2-carboxylphenyl)-1-indanone 2-methyl-7-(4-formylphenyl)-1-indanone 2-methyl-7-(4-acetylphenyl)-1-indanone 2-methyl-7-(4-pivaloylphenyl)-1-indanone 2-methyl-7-(4-aminophenyl)-1-indanone 2-methyl-7-(3-aminophenyl)-1-indanone 2-methyl-7-(2-aminophenyl)-1-indanone 2-methyl-7-(4-dimethylaminophenyl)-1-indanone 2-methyl-7-(3-dimethylaminophenyl)-1-indanone 2-methyl-7-(4-(1-pyrrolidino)phenyl)-1-indanone 2-methyl-7-(4-hydrazinophenyl)-1-indanone 2-methyl-7-(4-cyanophenyl)-1-indanone 2-methyl-7-(3-cyanophenyl)-1-indanone 2-methyl-7-(2-cyanophenyl)-1-indanone 2-methyl-7-(4-trifluoromethoxyphenyl)-1-indanone 2-methyl-7-(4-fluorophenyl)-1-indanone 2-methyl-7-(4-bromophenyl)-1-indanone 2-methyl-7-(2,4-difluorophenyl)-1-indanone 2-methyl-7-(4-chlorophenyl)-1-indanone 2-methyl-7-(3,5-dichlorophenyl)-1-indanone 2-methyl-7-(4-trifluoromethylphenyl)-1-indanone 2-methyl-7-(3-trifluoromethylphenyl)-1-indanone 2-methyl-7-(3,5-bis(trifluoromethyl)phenyl)-1-indanone 2-methyl-7-(2,4-bis(trifluoromethyl)phenyl)-1-indanone 2-methyl-7-(2-furyl)-1-indanone 2-methyl-7-(3-furyl)-1-indanone 2-methyl-7-(5-methyl-2-furyl)-1-indanone 2-methyl-7-(benzofuryl)-1-indanone 2-methyl-7-(2-thiophenyl)-1-indanone 2-methyl-7-(5-methyl-2-thiophenyl)-1-indanone 2-methyl-7-(3-thiophenyl)-1-indanone 2-methyl-7-(5-isobutyl-2-thiophenyl)-1-indanone 2-methyl-7-(benzothiophenyl)-1-indanone 2-methyl-7-(N-methyl-2-pyrrolyl)-1-indanone 2-methyl-7-(N-methyl-3-pyrrolyl)-1-indanone 2-methyl-7-(2-pyridyl)-1-indanone 2-methyl-7-(3-pyridyl)-1-indanone 2-methyl-7-(4-pyridyl)-1-indanone 2-methyl-7-(2-pyrimidyl)-1-indanone 2-methyl-7-(2-quinolyl)-1-indanone 2-methyl-7-(3-quinolyl)-1-indanone 2-methyl-7-(4-isoquinolyl)-1-indanone 2-methyl-7-(2-thiazolyl)-1-indanone 2-methyl-7-(2-benzothiazolyl)-1-indanone 2-methyl-7-(2-N-methylimidazolyl)-1-indanone 2-methyl-7-(2-N-methylbenzoimidazolyl)-1-indanone 2-methyl-7-(2-oxazolyl)-1-indanone 2-methyl-7-(N-methyltriazolyl)-1-indanone 2-methyl-7-benzyl-1-indanone 2-methyl-7-(hex-1-en-6-yl)-1-indanone 2-methyl-7-(hex-1-en-1-yl)-1-indanone 2-methyl-7-vinyl-1-indanone 2-methyl-7-(2-trimethylsilylethen-1-yl)-1-indanone 2-methyl-7-(2-phenylethyn-1-yl)-1-indanone 2-methyl-7-(2-tert-butylethyn-1-yl)-1-indanone 2-methyl-7-allyl-1-indanone 2-methyl-7-(2-trimethylsilylethyn-1-yl)-1-indanone 2-methyl-7-(2-phenylethen-1-yl)-1-indanone 2-methyl-7-trimethylstannyl-1-indanone 2-methyl-7-tributylstannyl-1-indanone 2-methyl-7-triphenylstannyl-1-indanone 2-methyl-7-(boronic acid pinacol ester)-1-indanone 2-methyl-7-(boronic acid trimethylene glycol ester)-1-indanone 2-methyl-7-(B-catecholborane)-1-indanone 2-methyl-7-diphenylphosphino-1-indanone 2-methyl-7-dibutylphosphino-1-indanone 2-methyl-7-(methoxyphenyl-methyl-phosphino)-1-indanone 2-ethyl-7-phenyl-1-indanone 2-ethyl-7-(4-tolyl)-1-indanone 2-ethyl-7-naphthyl-1-indanone 2-ethyl-7-(2-furyl)-1-indanone 2-isopropyl-7-(2-pyridyl)-1-indanone 2-isopropyl-7-phenyl-1-indanone 2-isopropyl-7-naphthyl-1-indanone 2-isobutyl-7-phenyl-1-indanone 2-isobutyl-7-naphthyl-1-indanone 2-cyclohexyl-7-phenyl-1-indanone 2-trifluoromethyl-7-phenyl-1-indanone 2-trifluoromethyl-7-(4-tolyl)-1-indanone 2-trifluoromethyl-7-naphthyl-1-indanone 2-trifluoromethyl-7-(4-methoxyphenyl)-1-indanone 2-trifluoromethyl-7-(3,5-bis(trifluoromethyl)phenyl)-1-indanone 2-methyl-4-methoxy-7-phenyl-1-indanone 2,6-dimethyl-7-phenyl-1-indanone 2,5-dimethyl-7-phenyl-1-indanone 2,5-dimethyl-7-p-tolyl-1-indanone 2,5-dimethyl-7-(2-thiophenyl)-1-indanone 2-methyl-5-phenyl-7-naphthyl-1-indanone 2-methyl-5,7-diphenyl-1-indanone 2-methyl-7-(4-fluorophenyl)-1-indanone 2-methyl-5-diphenylphosphino-7-(4-nitrophenyl)-1-indanone 2-methyl-5-chloro-7-phenyl-1-indanone 2,6-dimethyl-7-(4-methoxyphenyl)-1-indanone 2-ethyl-5-vinyl-7-(2-furyl)-1-indanone 2-isopropyl-5-trifluoromethyl-7-phenyl-1-indanone 2-cyclohexyl-5-methyl-7-(2-pyridyl)-1-indanone 2-trifluoromethyl-7-naphthyl-1-indanone 2-trimethylsilyl-5-isopropyl-7-(boronic acid pinacol ester)-1-indanone 2-dimethylamino-6-cyclohexyl-7-trimethylstannyl-1-indanone 2-ethyl-7-(9-phenanthrenyl)-1-indanone 2-ethyl-7-(2-pyridyl)-1-indanone 2-butyl-7-phenyl-1-indanone 2-butyl-7-(4-tolyl)-1-indanone 2-butyl-7-naphthyl-1-indanone 2-butyl-7-(2-furyl)-1-indanone 2-butyl-7-(p-phenanthrenyl)-1-indanone 2-butyl-7-(2-pyridyl)-1-indanone 2-ethyl-7-(4-tert-butylphenyl)-1-indanone 2-n-propyl-7-phenyl-1-indanone 2-n-propyl-7-naphthyl-1-indanone 2-n-propyl-7-(4-tert-butylphenyl)-1-indanone 2-n-propyl-7-(4-methylphenyl)-1-indanone 2-n-butyl-7-phenyl-1-indanone 2-n-butyl-7-naphthyl-1-indanone 2-n-butyl-7-(4-tert-butylphenyl)-1-indanone 2-n-butyl-7-(4-methylphenyl)-1-indanone Both indanones of the formulae I and Ia and also indanones of the formulae II and IIa are suitable, inter alia, as intermediates in the preparation of metallocenes and active compounds in the fields of pharmacy and crop protection.

The indanones of the formulae II and IIa can easily be converted into the indenes of the formulae V and Va by literature methods (eg.: R. C. Larock, Comprehensive Organic Transformations, VCH, 1989, EP 0 629 632 A2).

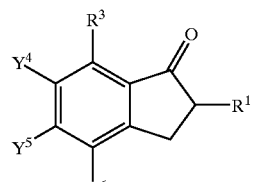

(II)

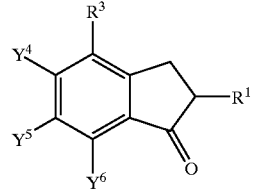

(IIa)

-continued

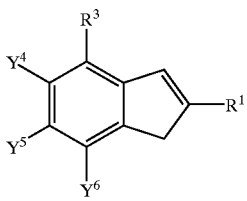

(V)

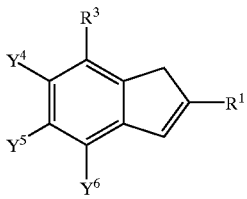

(Va)

In the formulae II, IIa, V and Va, the radicals $R^1$, $R^3$, $Y^4$, $Y^5$ and $Y^6$ are as defined above for formulae II and Ia.

Metallocenes can be prepared from the indenes of the formulae V and Va by literature methods (eg. EP 576 970, EP 629 632). Preference is given to unbridged or bridged metallocenes of the formula (VI)

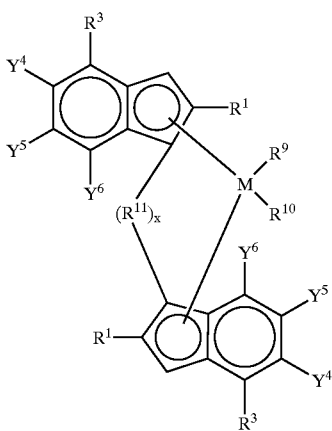

(VI)

where $R^1$, $R^3$, $Y^4$, $Y^5$ and $Y^6$ are as defined above for formula II, M is a transition element of group 4, 5 or 6 of the Periodic Table of the Elements, eg. titanium, zirconium, hafnium, vanadium, niobium, tantalum, chromium, molybdenum, tungsten, preferably titanium, zirconium, hafnium, particularly preferably zirconium, $R^9$ and $R^{10}$ are identical or different and are each a hydrogen atom, hydroxy or a halogen atom or a $C_1$–$C_{40}$-group such as $C_1$–$C_{10}$-alkyl, $C_1$–$C_{10}$-alkoxy, $C_6$–$C_{10}$-aryl, $C_6$–$C_{10}$-aryloxy, $C_2$–$C_{10}$-alkenyl, $C_7$–$C_{40}$-arylalkyl, $C_7$–$C_{40}$-alkylaryl, $C_8$–$C_{40}$-arylalkenyl, preferably hydrogen, $C_1$–$C_3$-alkyl, in particular methyl, $C_1$–$C_3$-alkoxy, $C_6$-aryl, $C_6$-aryloxy, $C_2$–$C_{10}$-alkenyl, $C_7$–$C_{10}$-arylalkyl, $C_7$–$C_{10}$-alkylaryl, $C_8$–$C_{10}$-arylalkenyl or a halogen atom, in particular chlorine, x is zero or 1, $R^{11}$ is a bridge such as

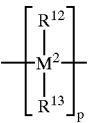

where $M^2$ is carbon, silicon, germanium or tin, preferably silicon or carbon, in particular silicon, p is 1, 2 or 3, preferably 1 or 2, in particular 1, $R^{12}$ and $R^{13}$ are identical or different and are each a hydrogen atom, a halogen atom or a $C_1$–$C_{20}$-group such as $C_1$–$C_{20}$-alkyl, $C_6$–$C_{14}$-aryl, $C_1$–$C_{10}$-alkoxy, $C_2$–$C_{10}$-alkenyl, $C_7$–$C_{20}$-arylalkyl, $C_7$–$C_{20}$-alkylaryl, $C_6$–$C_{10}$-aryloxy, $C_1$–$C_{10}$-fluoroalkyl, $C_6$–$C_{10}$-haloaryl or $C_2$–$C_{10}$-alkynyl or $R^{12}$ and $R^{13}$ together with the atom connecting them form a ring; preferably, $R^{12}$ and $R^{13}$ are hydrogen, $C_1$–$C_6$-alkyl, $C_6$–$C_{10}$-aryl, $C_1$–$C_6$-alkoxy, $C_2$–$C_4$-alkenyl, $C_7$–$C_{10}$-arylalkyl, $C_7$–$C_{10}$-alkylaryl, particularly preferably $C_1$–$C_6$-alkyl or $C_6$–$C_{10}$-aryl, or $R^{12}$ and $R^{13}$ together with the atom connecting them form a ring.

$R^3$ are identical or different, preferably identical, and are preferably each a $C_6$–$C_{40}$-aryl group which may contain heteroatoms. Preference is given to $C_6$–$C_{40}$-aryl groups which may be halogenated, in particular fluorinated, or may bear halogenated, in particular fluorinated, $C_1$–$C_{20}$-hydrocarbon radicals. $R^3$ are particularly preferably each a phenyl, naphthyl, phenanthryl or anthracenyl group which is fluorinated and/or bears fluorinated, in particular perfluorinated, $C_1$–$C_{10}$-hydrocarbon radicals such as $CF_3$ or $C_2F_5$.

Particularly suitable metallocenes of the formula VI comprise the following molecular fragments:

$MR^9R^{10}$: $ZrCL_2$, $Zr(CH_3)_2$, $HfCl_2$, $Hf(CH_3)_2$ $R^1$: linear $C_1$–$C_{10}$-alkyl $Y^4$, $Y^5$, $Y^6$: hydrogen $R^3$: 4-($C_4$–$C_8$-alkyl)phenyl, where the 4-($C_4$–$C_8$-alkyl) group is preferably a branched $C_4$–$C_8$-alkyl group, in particular a tert-butyl group, $R^{11}$: dimethylsilyl, diphenylsilyl, methylphenylsilyl.

Further preferred metallocene components of the metallocenes of the formula VI are combinations of the following molecular fragments:

$MR^9R^{10}$: $ZrCl_2$, $Zr(CH_3)_2$, $R^1$: $C_1$–$C_4$-alkyl such as methyl, ethyl, isopropyl, n-butyl, sec-butyl, $Y^6$: hydrogen $Y^4$, $Y^5$: hydrogen, $C_1$–$C_4$-alkyl, $C_6$–$C_{10}$-aryl, $R^3$: 4-fluorophenyl, 3,5-difluorophenyl, pentafluorophenyl, 4-trifluoromethylphenyl, 3-trifluoromethylphenyl, 2-trifluoromethylphenyl, 3,5-ditrifluoromethylphenyl, 2,6-ditrifluoromethylphenyl, pentatrifluoromethylphenyl, 4-pentafluoroethylphenyl, 3-pentafluoroethylphenyl, 2-pentafluoroethylphenyl, 3,5-dipentafluoroethylphenyl, 2,6-dipentafluoroethylphenyl, mono-, di-, tri- and tetrafluoronaphthyl, penta(pentafluoroethyl)-phenyl, $R^{11}$: dimethylsilanediyl, dimethylgermanediyl, $CH_2$—$CH_2$, $CH(CH_3)$—$CH_2$, $CH(CH_3)$—$CH(CH_3)$, $C(CH_3)_2$—$CH_2$, $C(CH_3)_2$—$C(CH_3)_2$.

Radicals having the same designation on the two indenyl ligands: can be identical to or different from one another.

Thus, the two indenyl ligands can be identical or can be different from one another (eg. when one $Y^6$=H, and the other $Y^6$=$CH_3$ or when one $Y^6$=$CH_3$ and the other $Y^6$=$C_2H_5$).

Illustrative examples of metallocenes which can be prepared, which do not, however, restrict the scope of the invention, are:

dimethylsilanediylbis(2-methyl-4-(4-fluorophenyl)indenyl)$ZrCl_2$ dimethylsilanediylbis(2-methyl-4-(3,5-difluorophenyl)indenyl)$ZrCl_2$ dimethylsilanediylbis(2-methyl-4-(2,6-difluorophenyl)indenyl)$ZrCl_2$ dimethylsilanediylbis(2-methyl-4-(pentafluorophenyl)indenyl)$ZrCl_2$ dimethylsilanediylbis(2-methyl-4-(4-trifluoromethylphenyl)indenyl)$ZrCl_2$ dimethylsilanediylbis(2-methyl-4-(3,5-ditrifluoromethylphenyl)indenyl)$ZrCl_2$ dimethylsilanediylbis(2-methyl-4-(2,6-ditrifluoromethylphenyl)indenyl)$ZrCl_2$ dimethylsilanediylbis(2-methyl-4-(pentatrifluoromethylphenyl)indenyl)$ZrCl_2$ dimethylsilanediylbis(2-methyl-4-(4-pentafluoroethylphenyl)indenyl)$ZrCl_2$ dimethylsilanediylbis(2-methyl-4-(3,5-dipentafluoroethylphenyl)indenyl)$ZrCl_2$ dimethylsilanediylbis(2-methyl-4-(2,6-dipentafluoroethylphenyl)indenyl)$ZrCl_2$ dimethylsilanediylbis(2-methyl-4-(penta(pentafluoroethyl)phenyl)indenyl)$ZrCl_2$ dimethylsilanediylbis(2-methyl-4-(3,5-difluorophenyl)-6-phenylindenyl)$ZrCl_2$ dimethylsilanediylbis(2-methyl-4-(3,5-difluoromethylphenyl)-6-phenylindenyl)$ZrCl_2$ dimethylsilanediylbis(2-methyl-4-(4-pentafluoroethylphenyl)-6-phenylindenyl)$ZrCl_2$ dimethylsilanediylbis(2-methyl-4-(3,5-dipentafluoroethylphenyl)-6-phenylindenyl)$ZrCl_2$ dimethylsilanediylbis(2-methyl-4-(pentafluorophenyl)-6-phenylindenyl)$ZrCL_2$ dimethylsilanediylbis(2-methyl-4-(3,5-ditrifluoromethylphenyl)-6-methylindenyl)$ZrCl_2$ dimethylsilanediylbis(2-methyl-4-(3,5-ditrifluoromethylphenyl)-6-isopropylindenyl)$ZrCl_2$ dimethylsilanediylbis[1-(2-n-propyl-4-(4-tert-butylphenyl)indenyl)]zirconium dichloride dimethylsilanediylbis[1-n-butyl-4-(4-tert-butylphenyl)indenyl)]zirconium dichloride dimethylsilanediylbis[1-(2-n-pentyl-4-(4-tert-butylphenyl)indenyl)]zirconium dichloride dimethylsilanediylbis(2-n-butyl-4-(3,5-difluorophenyl)indenyl)$ZrCl_2$ dimethylsilanediylbis(2-n-butyl-4-(4-trifluoromethylphenyl)indenyl)$ZrCl_2$ dimethylsilanediylbis(2-n-butyl-4-(3,5-ditrifluoromethylphenyl)indenyl)$ZrCl_2$ dimethylsilanediylbis(2-n-butyl-4-(4-pentafluoroethylphenyl)indenyl)$ZrCl_2$ dimethylsilanediylbis(2-n-butyl-4-(3,5-dipentafluoroethylphenyl)indenyl)$ZrCl_2$ dimethylsilanediylbis(2-n-butyl-4-(pentafluorophenyl)indenyl)$ZrCl_2$ dimethylsilanediylbis(2-n-butyl-4-(3,5-difluorophenyl)indenyl)$ZrCl_2$ dimethylsilanediylbis(2-n-butyl-4-(pentafluorophenyl)indenyl)$ZrCl_2$ dimethylsilanediylbis(2-sec-butyl-4-(3,5-difluorophenyl)indenyl)$ZrCl_2$ dimethylsilanediylbis(2-sec-butyl-4-(4-trifluoromethylphenyl)indenyl)$ZrCl_2$ dimethylsilanediylbis(2-sec-butyl-4-(3,5-ditrifluoromethylphenyl)indenyl)$ZrCl_2$ dimethylsilanediylbis(2-sec-butyl-4-(4-pentafluoroethylphenyl)indenyl)$ZrCl_2$ dimethylsilanediylbis(2-sec-butyl-4-(3,5-dipentafluoroethylphenyl)indenyl)$ZrCl_2$ dimethylsilanediylbis(2-sec-butyl-4-(pentafluorophenyl)indenyl)$ZrCl_2$ dimethylsilanediylbis(2-sec-butyl-4-(3,5-difluorophenyl)indenyl)$ZrCl_2$ dimethylsilanediylbis(2-sec-butyl-4-(pentafluorophenyl)indenyl)$ZrCl_2$ dimethylsilanediylbis(2-isobutyl-4-(3,5-difluorophenyl)indenyl)$ZrCl_2$ dimethylsilanediylbis(2-isobutyl-4-(4-trifluoromethylphenyl)indenyl)$ZrCl_2$ dimethylsilanediylbis(2-isobutyl-4-(3,5-ditrifluoromethylphenyl)indenyl)$ZrCl_2$ dimethylsilanediylbis(2-isobutyl-4-(4-pentafluoroethylphenyl)indenyl)$ZrCl_2$ dimethylsilanediylbis(2-isobutyl-4-(3,5-dipentafluoroethylphenyl)indenyl)$ZrCl_2$ dimethylsilanediylbis(2-isobutyl-4-(pentafluorophenyl)indenyl)$ZrCl_2$ dimethylsilanediylbis(2-ethyl-4-(3,5-difluorophenyl)indenyl)$ZrCl_2$ dimethylsilanediylbis(2-ethyl-4-(4-trifluoromethylphenyl)indenyl)$ZrCl_2$ dimethylsilanediylbis(2-ethyl-4-(3,5-ditrifluoromethylphenyl)indenyl)$ZrCl_2$ dimethylsilanediylbis(2-ethyl-4-(4-pentafluoroethylphenyl)indenyl)$ZrCl_2$ dimethylsilanediylbis(2-ethyl-4-(3,5-dipentafluoroethylphenyl)indenyl)$ZrCl_2$ dimethylsilanediylbis(2-ethyl-4-(pentafluorophenyl)indenyl)$ZrCl_2$ 1,2-ethanediylbis(2-methyl-4-phenylindenyl)zirconium dichloride 1,2-ethanediylbis(2-ethyl-4-phenylindenyl)zirconium dichloride 1,2-ethanediylbis(2-isobutyl-4-phenylindenyl)zirconium dichloride 1,2-ethanediylbis(2-n-butyl-4-phenylindenyl)zirconium dichloride 1,2-ethanediylbis(2-sec-butyl-4-phenylindenyl)zirconium dichloride 1,2-ethanediylbis(2-methyl-4-(1-naphthyl)indenyl)zirconium dichloride 1,2-ethanediylbis(2-ethyl-4-(1-naphthyl)indenyl)zirconium dichloride 1,2-ethanediylbis(2-isobutyl-4-(1-naphthyl)indenyl)zirconium dichloride 1,2-ethanediylbis(2-n-butyl-4-(1-naphthyl)indenyl)zirconium dichloride 1,2-ethanediylbis(2-sec-butyl-4-(1-naphthyl)indenyl)zirconium dichloride 1,2-ethanediylbis(2-methyl-4-(2-naphthyl)indenyl)zirconium dichloride 1,2-ethanediylbis(2-ethyl-4-(2-naphthyl)indenyl)zirconium dichloride 1,2-ethanediylbis(2-isobutyl-4-(2-naphthyl)indenyl)zirconium dichloride 1,2-ethanediylbis(2-n-butyl-4-(2-naphthyl)indenyl)zirconium dichloride 1,2-ethanediylbis(2-sec-butyl-4-(2-naphthyl)indenyl)zirconium dichloride 1,2-ethanediylbis(2-methyl-4-phenanthrylindenyl)zirconium dichloride 1,2-ethanediylbis(2-ethyl-4-phenanthrylindenyl)zirconium dichloride 1,2-ethanediylbis(2-isobutyl-4-phenanthrylindenyl)zirconium dichloride 1,2-ethanediylbis(2-n-butyl-4-phenanthrylindenyl)zirconium dichloride 1,2-ethanediylbis(2-sec-butyl-4-phenanthrylindenyl)zirconium dichloride 1,2-ethanediylbis(2-methyl-4-(3,5-dimethylphenyl)indenyl)zirconium dichloride 1,2-ethanediylbis(2-ethyl-4-(3,5-dimethylphenyl)indenyl)zirconium dichloride 1,2-ethanediylbis(2-n-butyl-4-(3,5-dimethylphenyl)indenyl)zirconium dichloride 1,2-ethanediylbis(2-sec-butyl-4-(3,5-dimethylphenyl)indenyl)zirconium dichloride 1,2-ethanediylbis(2-methyl-4-(4-methylphenyl)indenyl)zirconium dichloride 1, 2-ethanediylbis(2-ethyl-4-(4-methylphenyl)indenyl)zirconium dichloride 1,2- ethanediylbis(2-isobutyl-4-(4-methylphenyl)indenyl) zirconium dichloride 1,2-ethanediylbis(2-n-butyl-4-(4-methylphenyl)indenyl)zirconium dichloride 1,2-ethanediylbis(2-sec-butyl-4-(4-methylphenyl)indenyl) zirconium dichloride 1,2-ethanediylbis(2-methyl-4-anthracenylindenyl)zirconium dichlobride 1,2-ethanediylbis(2-ethyl-4-anthracenylindenyl)zirconium dichloride 1,2-ethanediylbis(2-isobutyl-4-anthracenylindenyl)zirconium dichloride 1,2-ethanediylbis(2-n-butyl-4-anthracenylindenyl) zirconium dichloride 1,2-ethanediylbis(2-sec-butyl-4-anthracenylindenyl)zirconium dichloride Also preferred are the corresponding dimethylzirconium compounds and the corresponding compounds having a 1,2-(1-methylethane-diyl), 1,2-(1,1-dimethylethanediyl) or 1,2-(1,2-dimethylethane-diyl) bridge.

dimethylsilanediylbis[1-(2-methyl-4-phenylindenyl)] zirconium dichloride dimethylsilanediylbis[1-(2-methyl-4-(1-naphthyl)indenyl)]zirconium dichloride dimethylsilanediylbis[1-(2-methyl-4-(2-naphthyl) indenyl)]zirconium dichloride dimethylsilanediylbis[1-(2-methyl-4-(4-methylphenyl)indenyl)]zirconium dichloride dimethylsilanediylbis[1-(2-methyl-4-(3-methylphenyl)indenyl)]zirconium dichloride dimethylsilanediylbis[1-(2-methyl-4-(2-methylphenyl) indenyl)]zirconium dichloride dimethylsilanediylbis[1-(2-methyl-4-(4-ethylphenyl)indenyl)]zirconium dichloride dimethylsilanediylbis[1-(2-methyl-4-(3-ethylphenyl)indenyl)]zirconium dichloride dimethylsilanediylbis[1-(2-methyl-4-(2-ethylphenyl) indenyl)]zirconium dichloride dimethylsilanediylbis[1-(2-methyl-4-(4-butylphenyl)indenyl)]zirconium dichloride dimethylsilanediylbis[1-(2-methyl-4-(4-isopropylphenyl)indenyl)]zirconium dichloride dimethylsilanediylbis[1-(2-methyl-4-(3-isopropylphenyl)indenyl)]zirconium dichloride dimethylsilanediylbis[1-(2-methyl-4-(2-isopropylphenyl)indenyl)]zirconium dichloride dimethylsilanediylbis[1-(2-methyl-4-(4-tert-butylphenyl)indenyl)]zirconium dichloride dimethylsilanediylbis[1-(2-methyl-4-(3-tert-butylphenyl)indenyl)]zirconium dichloride dimethylsilanediylbis[1-(2-methyl-4-(4-cyclohexylphenyl)indenyl)]zirconium dichloride dimethylsilanediylbis[1-(2-methyl-4-(3-cyclohexylphenyl)indenyl)]zirconium dichloride dimethylsilanediylbis[1-(2-methyl-4-(4-triisopropylsilylphenyl)indenyl)]zirconium dichloride dimethylsilanediylbis[1-(2-methyl-4-(4-biphenyl) indenyl)]zirconium dichloride dimethylsilanediylbis[1-(2-methyl-4-(3-biphenyl)indenyl)]zirconium dichloride dimethylsilanediylbis[1-(2-methyl-4-(2-biphenyl) indenyl)]zirconium dichloride dimethylsilanediylbis[1-(2-methyl-4-(4-biphenyl)indenyl)]zirconium dichloride dimethylsilanediylbis[1-(2-methyl-4-(4-styryl)indenyl)]zirconium dichloride dimethylsilanediylbis[1-(2-methyl-4-(3-styryl) indenyl)]zirconium dichloride dimethylsilanediylbis[1-(2-methyl-4-(2-styryl)indenyl)]zirconium dichloride dimethylsilanediylbis[1-(2-methyl-4-(9-anthracenyl) indenyl)]zirconium dichloride dimethylsilanediylbis[1-(2-methyl-4-(9-phenanthrenyl)indenyl)]zirconium dichloride dimethylsilanediylbis[1-(2-methyl-4-(4-methyl-1-naphthyl)indenyl)]zirconium dichloride dimethylsilanediylbis[1-(2-methyl-4-(2-methyl-1-naphthyl)indenyl)]zirconium dichloride dimethylsilanediylbis[1-(2-methyl-4-(2,4-dimethylphenyl)indenyl)]zirconium dichloride dimethylsilanediylbis[1-(2-methyl-4-(2,3-dimethylphenyl)indenyl)]zirconium dichloride dimethylsilanediylbis[1-(2-methyl-4-(3,5-dimethylphenyl)indenyl)]zirconium dichloride dimethylsilanediylbis[1-(2-methyl-4-(3,4-dimethylphenyl)indenyl)]zirconium dichloride dimethylsilanediylbis[1-(2-methyl-4-(2,6-dimethylphenyl)indenyl)]zirconium dichloride dimethylsilanediylbis[1-(2-methyl-4-(2,3,4-trimethylphenyl)indenyl)]zirconium dichloride dimethylsilanediylbis[1-(2-methyl-4-(3,4,5-trimethylphenyl)indenyl)]zirconium dichloride dimethylsilanediylbis[1-(2-methyl-4-(2,4,5-trimethylphenyl)indenyl)]zirconium dichloride dimethylsilanediylbis[1-(2-methyl-4-(2,3,4-trimethylphenyl)indenyl)]zirconium dichloride dimethylsilanediylbis[1-(2-methyl-4-mesitylindenyl)] zirconium dichloride dimethylsilanediylbis[1-(2-methyl-4-(3,5-diphenylphenyl)indenyl)]zirconium dichloride dimethylsilanediylbis[1-(2-methyl-4-(3,5-diisopropylphenyl)indenyl)]zirconium dichloride dimethylsilanediylbis[1-(2-methyl-4-(4-methoxyphenyl)indenyl)]zirconium dichloride dimethylsilanediylbis[1-(2-methyl-4-(3-methoxyphenyl)indenyl)]zirconium dichloride dimethylsilanediylbis[1-(2-methyl-4-(2-methoxyphenyl)indenyl)]zirconium dichloride dimethylsilanediylbis[1-(2-methyl-4-(2,4-dimethoxyphenyl)indenyl)]zirconium dichloride dimethylsilanediylbis[1-(2-methyl-4-(3,5-dimethoxyphenyl)indenyl)]zirconium dichloride dimethylsilanediylbis[1-(2-methyl-4-(3,4-dimethoxyphenyl)indenyl)]zirconium dichloride dimethylsilanediylbis[1-(2-methyl-4-(3,4,5-trimethoxyphenyl)indenyl)]zirconium dichloride dimethylsilanediylbis[1-(2-methyl-4-(2,4,6-trimethoxyphenyl)indenyl)]zirconium dichloride dimethylsilanediylbis[1-(2-methyl-4-(4-phenoxyphenyl)indenyl)]zirconium dichloride dirmethylsilanediylbis[1-(2-methyl-4-(4-isopropoxyphenyl)indenyl)]zirconium dichloride dimethylsilanediylbis[1-(2-methyl-4-(4-fluorophenyl) indenyl)]zirconium dichloride dimethylsilanediylbis[1-(2-methyl-4-(3-fluorophenyl)indenyl)]zirconium dichloride dimethylsilanediylbis[1-(2-methyl-4-(2,4-difluorophenyl)indenyl)]zirconium dichloride dimethylsilanediylbis[1-(2-methyl-4-(3,5-difluorophenyl)indenyl)]zirconium dichloride dimethylsilanediylbis[1-(2-methyl-4-(2,3,5,6-tetrafluoro-4-methylphenyl)indenyl)]zirconium dichloride dimethylsilanediylbis[1-(2-methyl-4-(4-N,N-dimethylaminophenyl)indenyl)]zirconium dichloride dimethylsilanediylbis[1-(2-methyl-4-(3-N,N-dimethylaminophenyl)indenyl)]zirconium dichloride dimethylsilanediylbis[1-(2-methyl-4-(2-N,N-dimethylaminophenyl)indenyl)]zirconium dichloride dimethylsilanediylbis[1-(2-methyl-4-(4-(1-pyrrolidino)phenyl)indenyl)]zirconium dichloride dimethylsilanediylbis[1-(2-methyl-4-(4-(1-piperidino) phenyl)indenyl)]zirconium dichloride dimethylsilanediylbis[1-(2-methyl-4-(4-trifluoromethylphenyl)indenyl)]zirconium dichloride dimethylsilanediylbis[1-(2-methyl-4-(3-trifluoromethylphenyl)indenyl)]zirconium dichloride dimethylsilanediylbis[1-(2-methyl-4-(2-trifluoromethylphenyl)indenyl)]zirconium dichloride dimethylsilanediylbis[1-(2-methyl-4-(3,5-bis(trifluoromethyl)phenyl)indenyl)]zirconium dichloride
dimethylsilanediylbis[1-(2-methyl-4-(2,4-bis(trifluoromethyl)phenyl)indenyl)]zirconium dichloride
dimethylsilanediylbis[1-(2-methyl-4-(3-trifluoromethoxyphenyl)indenyl)]zirconium dichloride
dimethylsilanediylbis[1-(2-methyl-4-(methyl-4-trifluoromethoxyphenyl)indenyl)]zirconium dichloride
dimethylsilanediylbis[1-(2-methyl-4-(4-pentafluoroethylphenylindenyl))]zirconium dichloride
dimethylsilanediylbis[1-(2-methyl-4-(4-thioanisylphenyl)indenyl)]zirconium dichloride
dimethylsilanediylbis[1-(2-methyl-4-(3-thioanisylphenyl)indenyl)]zirconium dichloride
dimethylsilanediylbis[1-(2-methyl-4-(2-thioanisylphenyl)indenyl)]zirconium dichloride
dimethylsilanediylbis[1-(2-methyl-4-(2-pyridyl)indenyl)]zirconium dichloride dimethylsilanediylbis[1-(2-methyl-4-(3-pyridyl)indenyl)]zirconium dichloride
dimethylsilanediylbis[1-(2-methyl-4-(4-pyridyl)indenyl)]zirconium dichloride dimethylsilanediylbis[1-(2-methyl-4-(2-pyrimidyl)indenyl)]zirconium dichloride dimethylsilanediylbis[1-(2-methyl-4-(2-furyl)indenyl)]zirconium dichloride dimethylsilanediylbis[1-(2-methyl-4-(3-furyl)indenyl)]zirconium dichloride
dimethylsilanediylbis[1-(2-methyl-4-(5-methyl-2-furyl)indenyl)]zirconium dichloride
dimethylsilanediylbis[1-(2-methyl-4-(2-benzofuryl)indenyl)]zirconium dichloride dimethylsilanediylbis[1-(2-methyl-4-(2-thiophenyl)indenyl)]zirconium dichloride dimethylsilanediylbis[1-(2-methyl-4-(3-thiophenyl)indenyl)]zirconium dichloride
dimethylsilanediylbis[1-(2-methyl-4-(5-methyl-2-thiophenyl)indenyl)]zirconium dichloride
dimethylsilanediylbis[1-(2-methyl-4-(5-isobutyl-2-thiophenyl)indenyl)]zirconium dichloride
dimethylsilanediylbis[1-(2-methyl-4-(2-benzothiophenyl)indenyl)]zirconium dichloride
dimethylsilanediylbis[1-(2-methyl-4-(2-thiazolyl)indenyl)]zirconium dichloride dimethylsilanediylbis[1-(2-methyl-4-(2-benzothiazolyl)indenyl)]zirconium dichloride dimeethylsilanediylbis[1-(2-methyl-4-(2-oxazolyl)indenyl)]zirconium dichloride
dimethylsilanediylbis[1-(2-methyl-4-(N-methyl-2-pyrrolyl)indenyl)]zirconium dichloride
dimethylsilanediylbis[1-(2-methyl-4-(N-methyl-3-pyrrolyl)indenyl)]zirconium dichloride
dimethylsilanediylbis[1-(2-methyl-4-(2-quinolyl)indenyl)]zirconium dichloride dimethylsilanediylbis[1-(2-methyl-4-(3-quinolyl)indenyl)]zirconium dichloride
dimethylsilanediylbis[1-(2-methyl-4-(isoquinolyl)indenyl)]zirconium dichloride dimethylsilanediylbis[1-(2-methyl-4-(N-methyltriazolyl)indenyl)]zirconium dichloride dimethylsilanediylbis[1-(2-methyl-4-(N-methyl-2-imidazolyl)indenyl)]zirconium dichloride
dimethylsilanediylbis[1-(2-methyl-4-(N-methyl-2-benzoimidazolyl)indenyl)]zirconium dichloride
dimethylsilanediylbis[1-(2-methyl-4-butylindenyl)]zirconium dichloride dimethylsilanediylbis[1-(2-methyl-4-cyclohexylindenyl)]zirconium dichloride
dimethylsilanediylbis[1-(2-methyl-4-isopropylindenyl)]zirconium dichloride
dimethylsilanediylbis[1-(2-methyl-4-benzylindenyl)]zirconium dichloride dimethylsilanediylbis[1-(2-methyl-4-isobutylindenyl)]zirconium dichloride
dimethylsilanediylbis[1-(2-methyl-4-(hex-1-en-6-yl)indenyl)]zirconium dichloride dimethylsilanediylbis[1-(2-methyl-4-(hex-1-en-1-yl)indenyl)]zirconium dichloride dimethylsilanediylbis[1-(2-methyl-4-vinylindenyl)]zirconium dichloride
dimethylsilanediylbis[1-(2-methyl-4-(2-trimethylsilylethen-1-yl)indenyl)]zirconium dichloride
dimethylsilanediylbis[1-(2-methyl-4-(2-phenylethyn-1-yl)indenyl)]zirconium dichloride
dimethylsilanediylbis[1-(2-methyl-4-(2-tert-butylethyn-1-yl)indenyl)]zirconium dichloride
dimethylsilanediylbis[1-(2-methyl-4-allylindenyl)]zirconium dichloride dimethylsilanediylbis[1-(2-methyl-4-(2-trimethylsilylethyn-1-yl)indenyl)]zirconium dichloride dimethylsilanediylbis[1-(2-methyl-4-(2-phenylethen-1-yl)indenyl)]zirconium dichloride dimethylsilanediylbis[1-(2-methyl-4-(diphenylphosphino)indenyl)]zirconium dichloride
dimethylsilanediylbis[1-(2-methyl-4-(dibutylphosphino)indenyl)]zirconium dichloride
dimethylsilanediylbis[1-(2-methyl-4-(dimethylphosphino)indenyl)]zirconium dichloride
dimethylsilanediylbis[1-(2-ethyl-4-phenylindenyl)]zirconium dichloride dimethylsilanediylbis[1-(2-ethyl-4-(1-naphthyl)indenyl)]zirconium dichloride
dimethylsilanediylbis[1-(2-ethyl-4-(2-naphthyl)indenyl)]zirconium dichloride dimethylsilanediylbis[1-(2-ethyl-4-(4-methylphenyl)indenyl)]zirconium dichloride dimethylsilanediylbis[1-(2-ethyl-4-(3-methylphenyl)indenyl)]zirconium dichloride
dimethylsilanediylbis[1-(2-ethyl-4-(2-methylphenyl)indenyl)]zirconium dichloride dimethylsilanediylbis[1-(2-ethyl-4-(4-ethylphenyl)indenyl)]zirconium dichloride dimethylsilanediylbis[1-(2-ethyl-4-(3-ethylphenyl)indenyl)]zirconium dichloride
dimethylsilanediylbis[1-(2-ethyl-4-(2-ethylphenyl)indenyl)]zirconium dichloride dimethylsilanediylbis[1-(2-ethyl-4-(4-butylphenyl)indenyl)]zirconium dichloride dimethylsilanediylbis[1-(2-ethyl-4-(4-isopropylphenyl)indenyl)]zirconium dichloride
dimethylsilanediylbis[1-(2-ethyl-4-(3-isopropylphenyl)indenyl)]zirconium dichloride
dimethylsilanediylbis[1-(2-ethyl-4-(2-isopropylphenyl)indenyl)]zirconium dichloride
dimethylsilanediylbis[1-(2-ethyl-4-(4-tert-butylphenyl)indenyl)]zirconium dichloride
dimethylsilanediylbis[1-(2-ethyl-4-(3-tert-butylphenyl)indenyl)]zirconium dichloride
dimethylsilanediylbis[1-(2-ethyl-4-(4-cyclohexylphenyl)indenyl)]zirconium dichloride
dimethylsilanediylbis[1-(2-ethyl-4-(3-cyclohexylphenyl)indenyl)]zirconium dichloride
dimethylsilanediylbis[1-(2-ethyl-4-(4-triisopropylsilylphenyl)indenyl)]zirconium dichloride
dimethylsilanediylbis[1-(2-ethyl-4-(4-biphenyl)indenyl))]zirconium dichloride dimethylsilanediylbis[1-(2-ethyl-4-(3-biphenyl)indenyl)]zirconium dichloride dimethylsilanediylbis[1-(2-ethyl-4-(2-biphenyl)indenyl)]zirconium dichloride dimethylsilanediylbis[1-(2-ethyl-4-(4-biphenyl)indenyl)]zirconium dichloride dimethylsilanediylbis[1-(2-ethyl-4-(4-styryl)indenyl)]zirconium dichloride dimethylsilanediylbis[1-(2-ethyl-4-(3-styryl)indenyl)]zirconium dichloride dimethylsilanediylbis[1-(2-ethyl-4-(2-styryl)indenyl)]zirconium dichloride dimethylsilanediylbis[1-(2-ethyl-4-(9-anthracenyl)indenyl)]zirconium dichloride dimethylsilanediylbis[1-(2-ethyl-4-(9-phenanthrenyl)indenyl)]zirconium dichloride dimethylsilanediylbis[1-(2-ethyl-4-(4-methyl-1-naphthyl)indenyl)]zirconium dichloride dimethylsilanediylbis[1-(2-ethyl-4-(2-methyl-1-naphthyl)indenyl)]zirconium dichloride dimethylsilanediylbis[1-(2-ethyl-4-(2,4-dimethylphenyl)indenyl)]zirconium dichloride dimethylsilanediylbis[1-(2-ethyl-4-(2,3-dimethylphenyl)indenyl)]zirconium dichloride dimethylsilanediylbis[1-(2-ethyl-4-(3,5-dimethylphenyl)indenyl)]zirconium dichloride dimethylsilanediylbis[1-(2-ethyl-4-(3,4-dimethylphenyl)indenyl)]zirconium dichloride dimethylsilanediylbis[1-(2-ethyl-4-(2,6-dimethylphenyl)indenyl)]zirconium dichloride dimethylsilanediylbis[1-(2-ethyl-4-(2,3,4-trimethylphenyl)indenyl)]zirconium dichloride dimethylsilanediylbis[1-(2-ethyl-4-(3,4,5-trimethylphenyl)indenyl)]zirconium dichloride dimethylsilanediylbis[1-(2-ethyl-4-(2,4,5-trimethylphenyl)indenyl)]zirconium dichloride dimethylsilanediylbis[1-(2-ethyl-4-(2,3,4-trimethylphenyl)indenyl)]zirconium dichloride dimethylsilanediylbis[1-(2-ethyl-4-mesitylindenyl)]zirconium dichloride dimethylsilanediylbis[1-(2-ethyl-4-(3,5-diphenylphenyl)indenyl)]zirconium dichloride dimethylsilanediylbis[1-(2-ethyl-4-(3,5-diisopropylphenyl)indenyl)]zirconium dichloride dimethylsilanediylbis[1-(2-ethyl-4-(4-methoxyphenyl)indenyl)zirconium dichloride dimethylsilanediylbis[1-(2-ethyl-4-(3-methoxyphenyl)indenyl)]zirconium dichloride dimethylsilanediylbis[1-(2-ethyl-4-(2-methoxyphenyl)indenyl)]zirconium dichloride dimethylsilanediylbis[1-(2-ethyl-4-(2,4-dimethoxyphenyl)indenyl)]zirconium dichloride dimethylsilanediylbis[1-(2-ethyl-4-(3,5-dimethoxyphenyl)indenyl)]zirconium dichloride dimethylsilanediylbis[1-(2-ethyl-4-(3,4-dimethoxyphenyl)indenyl)]zirconium dichloride dimethylsilanediylbis[1-(2-ethyl-4-(3,4,5-trimethoxyphenyl)indenyl)]zirconium dichloride dimethylsilanediylbis[1-(2-ethyl-4-(2,4,6-trimethoxyphenyl)indenyl)]zirconium dichloride dimethylsilanediylbis[1-(2-ethyl-4-(4-phenoxyphenyl)indenyl)]zirconium dichloride dimethylsilanediylbis[1-(2-n-propyl-4-phenylindenyl)]zirconium dichloride dimethylsilanediylbis[1-(2-n-propyl-4-naphthylindenyl)]zirconium dichloride dimethylsilanediylbis[1-(2-n-propyl-4-(4-tert-butylphenyl)indenyl)]zirconium dichloride dimethylsilanediylbis[1-(2-n-propyl-4-p-tolylindenyl)]zirconium dichloride dimethylsilanediylbis[1-(2-ethyl-4-(4-isopropoxyphenyl)indenyl)]zirconium dichloride dimethylsilanediylbis[1-(2-ethyl-4-(4-fluorophenyl)indenyl)]zirconium dichloride dimethylsilanediylbis[1-(2-ethyl-4-(3-fluorophenyl)indenyl)]zirconium dichloride dimethylsilanediylbis[1-(2-ethyl-4-(2,4-difluorophenyl)indenyl)]zirconium dichloride dimethylsilanediylbis[1-(2-ethyl-4-(3,5-difluorophenyl)indenyl)]zirconium dichloride dimethylsilanediylbis[1-(2-ethyl-4-(2,3,5,6-tetrafluoro-4-methylphenyl)indenyl)]zirconium dichloride dimethylsilanediylbis[1-(2-ethyl-4-(4-N,N-dimethylaminophenyl)indenyl)]zirconium dichloride dimethylsilanediylbis[1-(2-ethyl-4-(3-N,N-dimethylaminophenyl)indenyl)]zirconium dichloride dimethylsilanediylbis[1-(2-ethyl-4-(2-N,N-dimethylaminophenyl)indenyl)]zirconium dichloride dimethylsilanediylbis[1-(2-ethyl-4-(4-(1-pyrrolidino)phenyl)indenyl)]zirconium dichloride dimethylsilanediylbis[1-(2-ethyl-4-(4-(1-piperidino)phenyl)indenyl)]zirconium dichloride dimethylsilanediylbis[1-(2-ethyl-4-(4-trifluoromethylphenyl)indenyl)]zirconium dichloride dimethylsilanediylbis[1-(2-ethyl-4-(3-trifluoromethylphenyl)indenyl)]zirconium dichloride dimethylsilanediylbis[1-(2-ethyl-4-(2-trifluoromethylphenyl)indenyl)]zirconium dichloride dimethylsilanediylbis[1-(2-ethyl-4-(3,5-bis(trifluoromethyl)phenyl)indenyl)]zirconium dichloride dimethylsilanediylbis[1-(2-ethyl-4-(2,4-bis(trifluoromethyl)phenyl)indenyl)]zirconium dichloride dimethylsilanediylbis[1-(2-ethyl-4-(3-trifluoromethoxyphenyl)indenyl)]zirconium dichloride dimethylsilanediylbis[1-(2-ethyl-4-(2-ethyl-4-trifluoromethoxyphenyl)indenyl)]zirconium dichloride dimethylsilanediylbis[1-(2-ethyl-4-(4-pentafluoroethylphenyl)indenyl)]zirconium dichloride dimethylsilanediylbis[1-(2-ethyl-4-(4-thioanisylphenyl)indenyl)]zirconium dichloride dimethylsilanediylbis[1-(2-ethyl-4-(3-thioanisylphenyl)indenyl)]zirconium dichloride dimethylsilanediylbis[1-(2-ethyl-4-(2-thioanisylphenyl)indenyl)]zirconium dichloride dimethylsilanediylbis[1-(2-ethyl-4-(2-pyridyl)indenyl)]zirconium dichloride dimethylsilanediylbis[1-(2-ethyl-4-(3-pyridyl)indenyl)]zirconium dichloride dimethylsilanediylbis[1-(2-ethyl-4-(4-pyridyl)indenyl)]zirconium dichloride dimethylsilanediylbis[1-(2-ethyl-4-(2-pyrimidyl)indenyl)]zirconium dichloride dimethylsilanediylbis[1-(2-ethyl-4-(2-furyl)indenyl)]zirconium dichloride dimethylsilanediylbis[1-(2-ethyl-4-(3-furyl)indenyl)]zirconium dichloride dimethylsilanediylbis[1-(2-ethyl-4-(5-methyl-2-furyl)indenyl)]zirconium dichloride dimethylsilanediylbis[1-(2-ethyl-4-(2-benzofuryl)indenyl)]zirconium dichloride dimethylsilanediylbis[1-(2-ethyl-4-(2-thiophenyl)indenyl)]zirconium dichloride dimethylsilanediylbis[1-(2-ethyl-4-(3-thiophenyl)indenyl)]zirconium dichloride dimethylsilanediylbis[1-(2-ethyl-4-(5-methyl-2-thiophenyl)indenyl)]zirconium dichloride dimethylsilanediylbis[1-(2-ethyl-4-(5-isobutyl-2-thiophenyl)indenyl)]zirconium dichloride dimethylsilanediylbis[1-(2-ethyl-4-(2-benzothiophenyl)indenyl)]zirconium dichloride dimethylsilanediylbis[1-(2-ethyl-4-(2-thiazolyl)indenyl)]zirconium dichloride dimethylsilanediylbis[1-(2-ethyl-4-(2-benzothiazolyl)indenyl)]zirconium dichloride dimethylsilanediylbis[1-(2-ethyl-4-(2-oxazolyl)indenyl)]zirconium dichloride dimethylsilanediylbis[1-(2-ethyl-4-(N-methyl-2-pyrrolyl)indenyl)]zirconium dichloride dimethylsilanediylbis[1-(2-ethyl-4-(N-methyl-3-pyrrolyl)indenyl)]zirconium dichloride dimethylsilanediylbis[1-(2-ethyl-4-(2-quinolyl)indenyl)]zirconium dichloride dimethylsilanediylbis[1-(2-ethyl-4-(3-quinolyl)indenyl)]zirconium dichloride dimethylsilanediylbis[1-(2-ethyl-4-(isoquinolyl)indenyl)]zirconium dichloride dimethylsilanediylbis[1-(2-ethyl-4-(N-methyltriazole)indenyl)]zirconium dichloride dimethylsilanediylbis[1-(2-ethyl-4-(N-methyl-2-imidazolyl)indenyl)]zirconium dichloride dimethylsilanediylbis[1-(2-ethyl-4-(N-methyl-2-benzoimidazolyl)indenyl)]zirconium dichloride dimethylsilanediylbis[1-(2-ethyl-4-butylindenyl)]zirconium dichloride dimethylsilanediylbis[1-(2-ethyl-4-cyclohexylindenyl)]zirconium dichloride dimethylsilanediylbis[1-(2-ethyl-4-isopropylindenyl)]zirconium dichloride dimethylsilanediylbis[1-(2-ethyl-4-benzylindenyl)]zirconium dichloride dimethylsilanediylbis[1-(2-ethyl-4-isobutylindenyl)]zirconium dichloride dimethylsilanediylbis[1-(2-ethyl-4-(hex-1-en-6-yl)indenyl)]zirconium dichloride dimethylsilanediylbis[1-(2-ethyl-4-(hex-1-en-1-yl)indenyl)]zirconium dichloride dimethylsilanediylbis[1-(2-ethyl-4-vinylindenyl)]zirconium dichloride dimethylsilanediylbis[1-(2-ethyl-4-(2-trimethylsilylethen-1-yl)indenyl)]zirconium dichloride dimethylsilanediylbis[1-(2-ethyl-4-(2-phenylethyn-1-yl)indenyl)]zirconium dichloride dimethylsilanediylbis[1-(2-ethyl-4-(2-tert-butylethyn-1-yl)indenyl)]zirconium dichloride dimethylsilanediylbis[1-(2-ethyl-4-allylindenyl)]zirconium dichloride dimethylsilanediylbis[1-(2-ethyl-4-(2-trimethylsilylethyn-1-yl)indenyl)]zirconium dichloride dimethylsilanediylbis[1-(2-ethyl-4-(2-phenylethen-1-yl)indenyl)]zirconium dichloride dimethylsilanediylbis[1-(2-ethyl-4-(diphenylphosphino)indenyl)]zirconium dichloride dimethylsilanediylbis[1-(2-ethyl-4-(dibutylphosphino)indenyl)]zirconium dichloride dimethylsilanediylbis[1-(2-ethyl-4-(dimethylphosphino)indenyl)]zirconium dichloride dimethylsilanediylbis[1-(2-isopropyl-4-phenylindenyl)]zirconium dichloride dimethylsilanediylbis[1-(2-isopropyl-4-(1-naphthyl)indenyl)]zirconium dichloride dimethylsilanediylbis[1-(2-isopropyl-4-(2-naphthyl)indenyl)]zirconium dichloride dimethylsilanediylbis[1-(2-isopropyl-4-(4-methylphenyl)indenyl)]zirconium dichloride dimethylsilanediylbis[1-(2-isopropyl-4-(3,5-dimethylphenyl)indenyl)]zirconium dichloride dimethylsilanediylbis[1-(2-isopropyl-4-(4-trifluoromethylphenyl)indenyl)]zirconium dichloride dimethylsilanediylbis[1-(2-isopropyl-4-(3,5-bis(trifluoromethyl)phenyl)indenyl)]zirconium dichloride dimethylsilanediylbis[1-(2-isopropyl-4-(4-methoxyphenyl)indenyl)]zirconium dichloride dimethylsilanediylbis[1-(2-isopropyl-4-(2-furyl)indenyl)]zirconium dichloride dimethylsilanediylbis[1-(2-isopropyl-4-(2-pyridyl)indenyl)]zirconium dichloride dimethylsilanediylbis[1-(2-isopropyl-4-(2-thiophenyl)indenyl)]zirconium dichloride dimethylsilanediylbis[1-(2-isopropyl-4-(2-oxazolyl)indenyl)]zirconium dichloride dimethylsilanediylbis[1-(2-isopropyl-4-allylindenyl)]zirconium dichloride dimethylsilanediylbis[1-(2-isopropyl-4-cyclohexylindenyl)]zirconium dichloride dimethylsilanediylbis[1-(2,4-diisopropylindenyl)]zirconium dichloride dimethylsilanediylbis[1-(2-isopropyl-4-butylindenyl)]zirconium dichloride dimethylsilanediylbis[1-(2-isopropyl-4-benzylindenyl)]zirconium dichloride dimethylsilanediylbis[1-(2-isopropyl-4-(hex-1-en-6-yl)indenyl)]zirconium dichloride dimethylsilanediylbis[1-(2-isopropyl-4-(hex-1-en-1-yl)indenyl)]zirconium dichloride dimethylsilanediylbis[1-(2-isopropyl-4-vinylindenyl)]zirconium dichloride dimethylsilanediylbis[1-(2-isopropyl-4-(2-trimethylsilylethen-1-yl)indenyl)]zirconium dichloride dimethylsilanediylbis[1-(2-isopropyl-4-(2-phenylethyn-1-yl)indenyl)]zirconium dichloride dimethylsilanediylbis[1-(2-isopropyl-4-(2-tert-butylethyn-1-yl)indenyl)]zirconium dichloride dimethylsilanediylbis[1-(2-isobutyl-4-phenylindenyl)]zirconium dichloride dimethylsilanediylbis[1-(2-isobutyl-4-(1-naphthyl)indenyl)]zirconium dichloride dimethylsilanediylbis[1-(2-isobutyl-4-(2-naphthyl)indenyl)]zirconium dichloride dimethylsilanediylbis[1-(2-isobutyl-4-(4-methylphenyl)indenyl)]zirconium dichloride dimethylsilanediylbis[1-(2-isobutyl-4-(3,5-dimethylphenyl)indenyl)]zirconium dichloride dimethylsilanediylbis[1-(2-isobutyl-4-(4-trifluoromethylphenyl)indenyl)]zirconium dichloride dimethylsilanediylbis[1-(2-isobutyl-4-(3,5-bis(trifluoromethyl)phenyl)indenyl)]zirconium dichloride dimethylsilanediylbis[1-(2-isobutyl-4-(4-methoxyphenyl)indenyl)]zirconium dichloride dimethylsilanediylbis[1-(2-isobutyl-4-(2-furyl)indenyl)]zirconium dichloride dimethylsilanediylbis[1-(2-isobutyl-4-(2-pyridyl)indenyl)]zirconium dichloride dimethylsilanediylbis[1-(2-isobutyl-4-(2-thiophenyl)indenyl)]zirconium dichloride dimethylsilanediylbis[1-(2-isobutyl-4-(2-oxazolyl)indenyl)]zirconium dichloride dimethylsilanediylbis[1-(2-isobutyl-4-allylindenyl)]zirconium dichloride dimethylsilanediylbis[1-(2-isobutyl-4-cyclohexylindenyl)]zirconium dichloride dimethylsilanediylbis[1-(2,4-diisobutylindenyl)]zirconium dichloride dimethylsilanediylbis[1-(2-isobutyl-4-butylindenyl)]zirconium dichloride dimethylsilanediylbis[1-(2-isobutyl-4-benzylindenyl)]zirconium dichloride dimethylsilanediylbis[1-(2-isobutyl-4-(hex-1-en-6-yl)indenyl)]zirconium dichloride dimethylsilanediylbis[1-(2-isobutyl-4-(hex-1-en-1-yl)indenyl)]zirconium dichloride dimethylsilanediylbis[1-(2-isobutyl-4-vinylindenyl)]zirconium dichloride dimethylsilanediylbis[1-(2-isobutyl-4-(2-trimethylsilylethen-1-yl)indenyl)]zirconium dichloride dimethylsilanediylbis[1-(2-isobutyl-4-(2-phenylethyn-1-yl)indenyl)]zirconium dichloride dimethylsilanediylbis[1-(2-isobutyl-4-(2-tert-butylethyn-1-yl)indenyl)]zirconium dichloride dimethylsilanediylbis[1-(2-trifluoromethyl-4-phenylindenyl)]zirconium dichloride dimethylsilanediylbis[1-(2-trifluoromethyl-4-(1-naphthyl)indenyl)]zirconium dichloride dimethylsilanediylbis[1-(2-trifluoromethyl-4-(2-naphthyl)indenyl)]zirconium dichloride dimethylsilanediylbis[1-(2-trifluoromethyl-4-(4-methylphenyl)indenyl)]zirconium dichloride dimethylsilanediylbis[1-(2-trifluoromethyl-4-(3,5-dimethylphenyl)indenyl)]zirconium dichloride dimethylsilanediylbis[1-(2-trifluoromethyl-4-(4-trifluoromethylphenyl)indenyl)]zirconium dichloride dimethylsilanediylbis[1-(2-trifluoromethyl-4-(3,5-bis(trifluoromethyl)phenyl)indenyl)]zirconium dichloride dimethylsilanediylbis[1-(2-trifluoromethyl-4-(4-methoxyphenyl)indenyl)]zirconium dichloride dimethylsilanediylbis[1-(2-trifluoromethyl-4-(2-furyl)indenyl)]zirconium dichloride dimethylsilanediylbis[1-(2-trifluoromethyl-4-(2-pyridyl)indenyl)]zirconium dichloride dimethylsilanediylbis[1-(2-trifluoromethyl-4-(2-thiophenyl)indenyl)]zirconium dichloride dimethylsilanediylbis[1-(2-trifluoromethyl-4-(2-oxazolyl)indenyl)]zirconium dichloride dimethylsilanediylbis[1-(2-trifluoromethyl-4-allylindenyl)]zirconium dichloride dimethylsilanediylbis[1-(2-trifluoromethyl-4-cyclohexylindenyl)]zirconium dichloride dimethylsilanediylbis[1-(2,4-bis(trifluoromethylindenyl)]zirconium dichloride dimethylsilanediylbis[1-(2-trifluoromethyl-4-butylindenyl)]zirconium dichloride
dimethylsilanediylbis[1-(2-trifluoromethyl-4-benzylindenyl)]zirconium dichloride
dimethylsilanediylbis[1-(2-trifluoromethyl-4-(hex-1-en-6-yl)indenyl)]zirconium dichloride
dimethylsilanediylbis[1-(2-trifluoromethyl-4-(hex-1-en-1-yl)indenyl)]zirconium dichloride
dimethylsilanediylbis[1-(2-trifluoromethyl-4-vinylindenyl)]zirconium dichloride
dimethylsilanediylbis[1-(2-trifluoromethyl-4-(2-trimethylsilylethen-1-yl)indenyl)]zirconium dichloride
dimethylsilanediylbis[1-(2-trifluoromethyl-4-(2-phenylethyn-1-yl)indenyl)]zirconium dichloride
dimethylsilanediylbis[1-(2-trifluoromethyl-4-(2-tert-butylethyn-1-yl)indenyl)]zirconium dichloride
dimethylsilanediylbis[1-(2,5-dimethyl-4-phenylindenyl)]zirconium dichloride
dimethylsilanediylbis[1-(2,7-dimethyl-4-phenylindenyl)]zirconium dichloride
dimethylsilanediylbis[1-(2,6-dimethyl-4-phenylindenyl)]zirconium dichloride
dimethylsilanediylbis[1-(2,6-dimethyl-4-(1-naphthyl)indenyl)]zirconium dichloride
dimethylsilanediylbis[1-(2,6-dimethyl-4-(2-naphthyl)indenyl)]zirconium dichloride
dimethylsilanediylbis[1-(2,6-dimethyl-4-(4-methylphenyl)indenyl)]zirconium dichloride
dimethylsilanediylbis[1-(2,6-dimethyl-4-(4-methoxyphenyl)indenyl)]zirconium dichloride
dimethylsilanediylbis[1-(2,6-dimethyl-4-(2-pyridyl)indenyl)]zirconium dichloride
dimethylsilanediylbis[1-(2,7-dimethyl-4-(1-naphthyl)indenyl)]zirconium dichloride
dimethylsilanediylbis[1-(2,7-dimethyl-4-(2-naphthyl)indenyl)]zirconium dichloride
dimethylsilanediylbis[1-(2,7-dimethyl-4-(2-pyridyl)indenyl)]zirconium dichloride
dimethylsilanediylbis[1-(2-methyl-6-methoxy-4-phenylindenyl)]zirconium dichloride
dimethylsilanediylbis[1-(2-methyl-4,6-diphenylindenyl)]zirconium dichloride
dimethylsilanediylbis[1-(2-ethyl-4,6-diphenylindenyl)]zirconium dichloride
dimethylsilanediylbis[1-(2-cyclohexyl-6-methyl-4-phenylindenyl]zirconium dichloride
dimethylsilanediylbis[1-(2-methyl-6-vinyl-4-phenylindenyl)]zirconium dichloride
dimethylsilanediylbis[1-(2-methyl-6-benzyl-4-naphthylindenyl)]zirconium dichloride
dimethylsilanediylbis[1-(2-ethyl-5-methyl-4-(3,5-dimethylphenylindenyl)]zirconium dichloride
dimethylsilanediylbis[1-(2-phenyl-4-phenylindenyl)]zirconium dichloride
dimethylsilanediylbis[1-(2-phenyl-4-(1-naphthyl)indenyl)]zirconium dichloride
dimethylsilanediylbis[1-(2-phenyl-4-(2-naphthyl)indenyl)]zirconium dichloride
dimethylsilanediylbis[1-(2-phenyl-4-(4-methylphenyl)indenyl)]zirconium dichloride
dimethylsilanediylbis[1-(2-phenyl-4-(3,5-dimethylphenyl)indenyl)]zirconium dichloride
dimethylsilanediylbis[1-(2-phenyl-4-(4-trifluoromethylphenyl)indenyl)]zirconium dichloride
dimethylsilanediylbis[1-(2-phenyl-4-(3,5-bis(trifluoromethyl)phenyl)indenyl)]zirconium dichloride
dimethylsilanediylbis[1-(2-phenyl-4-(4-methoxyphenyl)indenyl)]zirconium dichloride
dimethylsilanediylbis[1-(2-phenyl-4-(2-furyl)indenyl)]zirconium dichloride
dimethylsilanediylbis[1-(2-phenyl-4-(2-pyridyl)indenyl)]zirconium dichloride
dimethylsilanediylbis[1-(2-phenyl-4-(2-thiophenyl)indenyl)]zirconium dichloride
dimethylsilanediylbis[1-(2-phenyl-4-(2-oxazolyl)indenyl)]zirconium dichloride
dimethylsilanediylbis[1-(2-phenyl-4-allylindenyl)]zirconium dichloride
dimethylsilanediylbis[1-(2-phenyl-4-cyclohexylindenyl)]zirconium dichloride
dimethylsilanediylbis[1-(2,4-diphenylindenyl)]zirconium dichloride
dimethylsilanediylbis[1-(2-phenyl-4-butylindenyl)]zirconium dichloride
dimethylsilanediylbis[1-(2-phenyl-4-benzylindenyl)]zirconium dichloride
dimethylsilanediylbis[1-(2-phenyl-4-(hex-1-en-6-yl)indenyl)]zirconium dichloride
dimethylsilanediylbis[1-(2-phenyl-4-(hex-1-en-1-yl)indenyl)]zirconium dichloride
dimethylsilanediylbis[1-(2-phenyl-4-vinylindenyl)]zirconium dichloride
dimethylsilanediylbis[1-(2-phenyl-4-(2-trimethylsilylethen-1-yl)indenyl)]zirconium dichloride
dimethylsilanediylbis[1-(2-phenyl-4-(2-phenylethyn-1-yl)indenyl)]zirconium dichloride
dimethylsilanediylbis[1-(2-phenyl-4-(2-tert-butylethyn-1-yl)indenyl)]zirconium dichloride
dimethylsilanediylbis[1-(2-cyclohexyl-4-phenylindenyl)]zirconium dichloride
dimethylsilanediylbis[1-(2-cyclohexyl-4-(1-naphthyl)indenyl)]zirconium dichloride
dimethylsilanediylbis[1-(2-cyclohexyl-4-(2-naphthyl)indenyl)]zirconium dichloride
dimethylsilanediylbis[1-(2-cyclohexyl-4-(4-methylphenyl)indenyl)]zirconium dichloride
dimethylsilanediylbis[1-(2-cyclohexyl-4-(3,5-dimethylphenyl)indenyl)]zirconium dichloride
dimethylsilanediylbis[1-(2-cyclohexyl-4-(4-trifluoromethylphenyl)indenyl)]zirconium dichloride
dimethylsilanediylbis[1-(2-cyclohexyl-4-(3,5-bis(trifluoromethyl)phenyl)indenyl)]zirconium dichloride
dimethylsilanediylbis[1-(2-cyclohexyl-4-(4-methoxyphenyl)indenyl)]zirconium dichloride
dimethylsilanediylbis[1-(2-cyclohexyl-4-(2-furyl)indenyl)]zirconium dichloride
dimethylsilanediylbis[1-(2-cyclohexyl-4-(2-pyridyl)indenyl)]zirconium dichloride
dimethylsilanediylbis[1-(2-cyclohexyl-4-(2-thiophenyl)indenyl)]zirconium dichloride
dimethylsilanediylbis[1-(2-cyclohexyl-4-(2-oxazolyl)indenyl)]zirconium dichloride
dimethylsilanediylbis[1-(2-cyclohexyl-4-allylindenyl)]zirconium dichloride
dimethylsilanediylbis[1-(2-cyclohexyl-4-cyclohexylindenyl)]zirconium dichloride
dimethylsilanediylbis[1-(2,4-dicyclohexylindenyl)]zirconium dichloride
dimethylsilanediylbis[1-(2-cyclohexyl-4-butylindenyl)]zirconium dichloride
dimethylsilanediylbis[1-(2-cyclohexyl-4-benzylindenyl)]zirconium dichloride
dimethylsilanediylbis[1-(2-cyclohexyl-4-(hex-1-en-6-yl)indenyl)]zirconium dichloride
dimethylsilanediylbis[1-(2-cyclohexyl-4-(hex-1-en-1-yl)indenyl)]zirconium dichloride
dimethylsilanediylbis[1-(2-cyclohexyl-4-vinylindenyl)]zirconium dichloride
dimethylsilanediylbis[1-(2-cyclohexyl-4-(2-trimethylsilylethen-1-yl)indenyl)]zirconium dichloride
dimethylsilanediylbis[1-(2-cyclohexyl-4-(2-phenylethyn-1-yl)indenyl)]zirconium dichloride
dimethylsilanediylbis[1-(2-cyclohexyl-4-(2-tert-butylethyn-1-yl)indenyl)]zirconium dichloride
dimethylsilanediylbis[1-(2-butyl-4-phenylindenyl)]zirconium dichloride
dimethylsilanediylbis[1-(2-butyl-4-(1-naphthyl)indenyl)]zirconium dichloride
dimethylsilanediylbis[1-(2-butyl-4-(2-naphthyl)indenyl)]zirconium dichloride
dimethylsilanediylbis[1-(2-butyl-4-(4-methylphenyl)indenyl)]zirconium dichloride dimethylsilanediylbis[1-(2-butyl-4-(3,5-dimethylphenyl)indenyl)]zirconium dichloride dimethylsilanediylbis[1-(2-butyl-4-(4-trifluoromethylphenyl)indenyl)]zirconium dichloride dimethylsilanediylbis[1-(2-butyl-4-(3,5-bis(trifluoromethyl)phenyl)indenyl)]zirconium dichloride dimethylsilanediylbis[1-(2-butyl-4-(4-methoxyphenyl)indenyl)]zirconium dichloride dimethylsilanediylbis[1-(2-butyl-4-(2-furyl)indenyl)]zirconium dichloride dimethylsilanediylbis[1-(2-butyl-4-(2-pyridyl)indenyl)]zirconium dichloride dimethylsilanediylbis[1-(2-butyl-4-(2-thiophenyl)indenyl)]zirconium dichloride dimethylsilanediylbis[1-(2-butyl-4-(2-oxazolyl)indenyl)]zirconium dichloride dimethylsilanediylbis[1-(2-butyl-4-allylindenyl)]zirconium dichloride dimethylsilanediylbis[1-(2-butyl-4-cyclohexylindenyl)]zirconium dichloride dimethylsilanediylbis[1-(2,4-dibutylindenyl)]zirconium dichloride dimethylsilanediylbis[1-(2-butyl-4-benzylindenyl)]zirconium dichloride dimethylsilanediylbis[1-(2-butyl-4-(hex-1-en-6-yl)indenyl)]zirconium dichloride dimethylsilanediylbis[1-(2-butyl-4-(hex-1-en-1-yl)indenyl)]zirconium dichloride dimethylsilanediylbis[1-(2-butyl-4-vinylindenyl)]zirconium dichloride dimethylsilanediylbis[1-(2-butyl-4-(2-trimethylsilylethen-1-yl)indenyl)]zirconium dichloride dimethylsilanediylbis[1-(2-butyl-4-(2-phenylethyn-1-yl)indenyl)]zirconium dichloride dimethylsilanediylbis[1-(2-butyl-4-(2-tert-butylethyn-1-yl)indenyl)]zirconium dichloride dimethylsilanediylbis[1-(2-methyl-4-phenylindenyl)]dimethylzirconium dimethylsilanediylbis[1-(2-methyl-4-phenylindenyl)]zirconium diethoxide dimethylsilanediylbis[1-(2-methyl-4-phenylindenyl)]zirconium diphenoxide dimethylsilanediylbis[1-(2-methyl-4-(1-naphthyl)indenyl)]-dimethylzirconium dimethylsilanediylbis[1-(2-methyl-4-(1-naphthyl)indenyl)]-dibenzylzirconium dimethylsilanediylbis[1-(2-methyl-4-(1-naphthyl)indenyl)]zirconium bis(dimethylamide) dimethylsilanediylbis[1-(2-methyl-4-(2-naphthyl)indenyl)]zirconium bis(diethylamide) dimethylsilanediylbis[1-(2-methyl-4-(pyridyl)indenyl)]dimethylzirconium dimethylsilanediylbis[1-(2-methyl-4-(3,5-bis(trifluoromethyl)phenyl)indenyl)]dimethylzirconium dimethylsilanediylbis[1-(2-methyl-4-(3,5-bis(trifluoromethyl)phenyl)indenyl)]zirconium dimethoxide dimethylsilanediylbis[1-(2-ethyl-4-(3,5-dimethylphenyl)indenyl)]-dimethylzirconium dimethylsilanediylbis[1-(2-dimethylamino-4-phenylindenyl)]-dimethylzirconium dimethylsilanediylbis[1-(2-N-piperino-4-naphthylindenyl)]zirconium dichloride dimethylsilanediylbis[1-(2-trimethylsilyl-4-cyclohexylindenyl)]-dimethylzirconium dimethylsilanediylbis[1-(2-trimethylsilyloxy-4-phenylindenyl)]zirconium dichloride dimethylsilanediylbis[1-(2,6-dimethyl-4-phenylindenyl)]zirconium dichloride dimethylsilanediylbis[1-(2-methyl-4,6-diphenylindenyl)]zirconium dichloride dimethylsilanediylbis[1-(2,5-dimethyl-4-naphthylindenyl)]zirconium dichloride dimethylsilanediylbis[1-(2-cyclohexyl-6-methyl-4-phenylindenyl)]zirconium dichloride dimethylsilanediylbis[1-(2,5,6-trimethyl-4-phenylindenyl)]zirconium dichloride dimethylsilanediylbis[1-(2-isopropyl-5,6-difluoro-4-phenylindenyl)]zirconium dichloride 1,2-ethanediylbis[1-(2-methyl-4-phenylindenyl)]zirconium dichloride 1,2-ethanediylbis[1-(2-methyl-4-phenylindenyl)]dimethylzirconium 1,2-ethanediylbis[1-(2-methyl-4-(1-naphthyl)indenyl)]zirconium dichloride 1,2-ethanediylbis[1-(2-methyl-4-(2-naphthyl)indenyl)]zirconium dichloride 1,2-ethanediylbis[1-(2-ethyl-4-(3,5-bis(trifluoromethyl)phenyl)indenyl)]zirconium dichloride 1,2-ethanediylbis[1-(2-butyl-4-(2-pyridyl)indenyl)]zirconium dichloride 1,2-ethanediylbis[1-(2-methyl-4-(2-furyl)indenyl)]zirconium dichloride 1,2-ethanediylbis[1-(2-methyl-4-(2-thiophenyl)indenyl)]zirconium dichloride 1,2-ethanediylbis[1-(2-isopropyl-4-(4-methoxyphenyl)indenyl)]zirconium dichloride 1,2-ethanediylbis[1-(2-methyl-4-(4-methylphenyl)indenyl))]zirconium dichloride 1,2-ethanediylbis[1-(2-isobutyl-4-phenylindenyl)]zirconium dichloride 1,2-ethanediylbis[1-(2-methyl-4-(3-dimethylaminophenyl)indenyl)]zirconium dichloride 1,2-butanediylbis[1-(2-methyl-4-phenylindenyl)]zirconium dichloride 1,2-butanediylbis[1-(2-methyl-4-phenylindenyl)]dimethylzirconium 1,2-butanediylbis[1-(2-methyl-4-(1-naphthyl)indenyl)]zirconium dichloride 1,2-butanediylbis[1-(2-methyl-4-(2-naphthyl)indenyl)]zirconium dichloride 1,2-butanediylbis[1-(2-ethyl-4-(3,5-bis(trifluoromethyl)phenyl)indenyl)]zirconium dichloride 1,2-butanediylbis[1-(2-butyl-4-(2-pyridyl)indenyl)]zirconium dichloride 1,2-butanediylbis[1-(2-methyl-4-(2-furyl)indenyl)]zirconium dichloride 1,2-butanediylbis[1-(2-phenyl-4-(2-thiophenyl)indenyl)]zirconium dichloride 1,2-butanediylbis[1-(2-isopropyl-4-(4-methoxyphenyl)indenyl)]zirconium dichloride 1,2-butanediylbis[1-(2,5-dimethyl-4-(4-methylphenyl)indenyl)]zirconium dichloride 1,2-butanediylbis[1-(2-isobutyl-4-phenylindenyl)]zirconium dichloride 1,2-butanediylbis[1-(2-methyl-4-(3-dimethylaminophenyl)indenyl)]zirconium dichloride bis[2-methyl-4-phenylindenyl]zirconium dichloride bis[2-methyl-4-phenylindenyl]dimethylzirconium bis[2-methyl-4-(1-naphthyl)indenyl]zirconium dichloride bis[2-methyl-4-(2-naphthyl)indenyl]zirconium dichloride bis[2-ethyl-4-(3,5-bis(trifluoromethyl)phenyl)indenyl]zirconium dichloride bis[2-butyl-4-(2-pyridyl)indenyl]zirconium dichloride bis[2-methyl-4-(2-furyl)indenyl]zirconium dichloride bis[2-methyl-4-(2-thiophenyl)indenyl]zirconium dichloride bis[2-isopropyl-4-(4-methoxyphenyl)indenyl]zirconium dichloride bis[2-methyl-4-(4-methylphenyl)indenyl]zirconium dichloride bis[2-isobutyl-4-phenylindenyl]zirconium dichloride bis[(2-methyl-4-(3-dimethylaminophenyl)indenyl]zirconium dichloride bis[2-methyl-4-(3,5-dimethylphenyl)indenyl]zirconium dichloride bis[2-N-piperidino-4-(3,5-dimethylphenyl)indenyl]zirconium dichloride [2-butyl-4-(2-pyridyl)indenyl]cyclopentadienylzirconium dichloride [2-ethyl-4-(3,5-bis(trifluoromethyl)phenylindenyl)]-[1-methylboratabenzene]zirconium dichloride [2-methyl-4-(3,5-dimethylphenyl)indenyl]fluorenylzirconium dichloride [2-isobutyl-4-(4-methoxyphenyl)indenyl)]-[2-methylindenyl]zirconium dichloride [2-cyclohexyl-4-(3-fluorophenylindenyl] trimethylcyclopentadienylzirconium dichloride [2-phenyl-4-(3-dimethylaminophenylindenyl))]-[tert-butylmethylcyclopentadienyl]zirconium dichloride methylphenylsilanediylbis[1-(2-methyl-4-phenylindenyl)]zirconium dichloride methylphenylsilanediylbis[1-(2-methyl-4- phenylindenyl)]dimethylzirconium methylphenylsilanediylbis[1-(2-methyl-4-(1-naphthyl)indenyl))]zirconium dichloride methylphenylsilanediylbis[1-(2-methyl-4-(2-naphthyl)indenyl)]zirconium dichloride methylphenylsilanediylbis[1-(2-ethyl-4-(3,5-trifluoromethyl)phenyl)indenyl)]zirconium dichloride methylphenylsilanediylbis[1-(2-butyl-4-(2-pyridyl)indenyl)]zirconium dichloride methylphenylsilanediylbis[1-(2-methyl-4-(2-furyl)indenyl)]zirconium dichloride methylphenylsilanediylbis[1-(2-methyl-4-(2-thiophenyl)indenyl)]zirconium dichloride methylphenylsilanediylbis[1-(2-isopropyl-4-(4-methoxyphenyl)indenyl)]zirconium dichloride methylphenylsilanediylbis[1-(2-methyl-4-(4-methylphenyl)indenyl)]zirconium dichloride methylphenylsilanediylbis[1-(2-isobutyl-4-phenylindenyl)]zirconium dichloride methylphenylsilanediylbis[1-(2-methyl-4-(3-dimethylaminophenyl)indenyl)]zirconium dichloride isopropylidenebis[1-(2-methyl-4-phenylindenyl)]zirconium dichloride isopropylidenebis[1-(2-methyl-4-phenylindenyl)]dimethylzirconium isoprbpylidenebis[1-(2-methyl-4-(1-naphthyl)indenyl)]zirconium dichloride isopropylidenebis[1-(2-methyl-4-(2-naphthyl)indenyl)]zirconium dichloride isopropylidenebis[1-(2-ethyl-4-(3,5-bis(trifluoromethyl)phenyl)indenyl)]zirconium dichloride isopropylidenebis[1-(2-butyl-4-(2-pyridyl)indenyl)]zirconium dichloride isopropylidenebis[1-(2-methyl-4-(2-furyl)indenyl)]zirconium dichloride isopropylidenebis[1-(2-methyl-4-(2-thiophenyl)indenyl)]zirconium dichloride isopropylidenebis[1-(2-isopropyl-4-(4-methoxyphenyl)indenyl)]zirconium dichloride isopropylidenebis[1-(2-methyl-4-(4-methylphenyl)indenyl)]zirconium dichloride isopropylidenebis[1-(2-isobutyl-4-phenylindenyl)]zirconium dichloride isopropylidenebis[1-(2-methyl-4-(3-dimethylaminophenyl)indenyl)]zirconium dichloride dimethylsilanediyl[1-(2-methyl-4-phenylindenyl)]cyclopentadienylzirconium dichloride dimethylsilanediyl[1-(2-methyl-4-phenylindenyl)]-[(1-(2-methylindenyl)]zirconium dichloride dimethylsilanediyl[1-(2-methyl-4-phenylindenyl)]trimethylcyclopentadienylzirconium dichloride dimethylsilanediyl[1-(2-methyl-4-phenylindenyl)]-[tert-butylmethylcyclopentadienyl]zirconium dichloride dimethylsilanediyl[1-(2-methyl-4-phenylindenyl)]fluorenylzirconium dichloride dimethylsilanediyl[1-(2-ethyl-4-naphthylindenyl)]tetramethylcyclopentadienylzirconium dichloride dimethylsilanediyl[1-(2-methyl-4-(3,5-bistrifluoromethyl)indenyl)]cyclopentadienylzirconium dichloride dimethylsilanediyl[1-(2-methyl-4-(2-pyridyl)indenyl)]tetramethylcyclopentadienylzirconium dichloride dimethylsilanediyl[1-(2-methyl-4-(2,4-dimethoxyphenyl)indenyl)]-[1-methylboratabenzene]zirconium dichloride dimethylgermanediylbis[1-(2-methyl-4-phenylindenyl)]zirconium dichloride dimethylgermanediylbis[1-(2-methyl-4-phenylindenyl)]dimethylzirconium dimethylgermanediylbis[1-(2-methyl-4-(1-naphthyl)indenyl)]zirconium dichloride dimethylgermanediylbis[1-(2-methyl-4-(2-naphthyl)indenyl)]zirconium dichloride dimethylgermanediylbis[1-(2-ethyl-4-(3,5-bis(trifluoromethyl)phenyl)indenyl)]zirconium dichloride dimethylgermanediylbis[1-(2-butyl-4-(2-pyridyl)indenyl)]zirconium dichloride dimethylgermanediylbis[1-(2-methyl-4-(2-furyl)indenyl)]zirconium dichloride dimethylgermanediylbis[1-(2-methyl-4-(2-thiophenyl)indenyl)]zirconium dichloride dimethylgermanediylbis[1(2-isopropyl-4-(4-methoxyphenyl)indenyl)]zirconium dichloride dimethylgermanediylbis[1-(2-methyl-4-(4-methylphenyl)indenyl)]zirconium dichloride dimethylgermanediylbis[1-(2-isobutyl-4-phenylindenyl)]zirconium dichloride dimethylgermanediylbis[1-(2-methyl-4-(3-dimethylaminophenyl)indenyl)]zirconium dichloride Further examples are the titanocenes and hafnocenes corresponding to the zirconocenes listed above.

The metallocenes which can be prepared from indanones via indenes are highly active catalyst components for olefin polymerization. Depending on the substitution pattern of the ligands, the metallocenes can be formed as a mixture of isomers. For the polymerization, the metallocenes are preferably used in isomerically pure form. The use of the racemate is sufficient in most cases.

However, it is also possible to use the pure enantiomer in the (+) or (−) form. An optically active polymer can be prepared using the pure enantiomers. However, the configurational isomers of the metallocenes should be separated off, since the polymerization-active center (the metal atom) in these compounds usually produces a polymer having different properties. For certain applications, for example flexible moldings, this can be quite desirable.

The present invention therefore also provides a process for preparing a polyolefin by polymerization of at least one olefin in the presence of a catalyst comprising at least one cocatalyst and at least one stereorigid metallocene compound of the formula I. For the purposes of the present invention, the term polymerization encompasses both homopolymerization and copolymerization.

In the process of the present invention, preference is given to polymerizing one or more olefins of the formula $R^\alpha$—CH=CH—$R^\beta$, where $R^\alpha$ and $R^\beta$ are identical or different and are each a hydrogen atom: or a hydrocarbon radical having from 1 to 20 carbon atoms, in particular from 1 to 10 carbon atoms, and $R^\alpha$ and $R^\beta$ together with the atoms connecting them may form one or more rings. Examples of such olefins are 1-olefins having from 2 to 40 carbon atoms, preferably 2–10 carbon atoms, for example ethylene, propylene, 1-butene, 1-pentene, 1-hexene, 4-methyl-1-pentene or 1-octene, styrene, dienes such as 1,3-butadiene, isoprene, 1,4-hexadiene or cyclic olefins such as norbornene or ethylidenenorbornene. In the process of the present invention, preference is given to homopolymerizing ethylene or propylene or copolymerizing ethylene with one or more cyclic olefins such as norbornene and/or one or more acyclic 1-olefins having from 3 to 20 carbon atoms, eg. propylene, and/or one or more dienes having from 4 to 20 carbon atoms, eg. 1,3-butadiene or 1,4-hexadiene. Examples of such copolymers are ethylene-norbornene copolymers, ethylene-propylene copolymers and ethylene-propylene-1,4-hexadiene copolymers. The polymerization is preferably carried out at from −60 to 250° C., particularly preferably from 50 to 200° C. The pressure is preferably from 0.5 to 2000 bar, particularly preferably from 5 to 64 bar.

The polymerization can be carried out in solution, in bulk, in suspension or in the gas phase, continuously or batchwise, in one or more stages. Preferred embodiments are gas-phase and solution polymerization.

The catalyst used in the process of the present invention preferably comprises one metallocene compound. It is also possible to use mixtures of two or more metallocene compounds, eg. for preparing polyolefins having a broad or multimodal molar mass distribution.

In principle, suitable cocatalysts for the process of the present invention are all compounds which, owing to their Lewis acidity, can convert the neutral metallocene into a cation and stabilize the latter ("labile coordination"). Furthermore, the catalyst or the anion formed therefrom should undergo no further reactions with the metallocene cation formed (EP 427 697). The cocatalyst used is preferably an aluminum compound and/or a boron compound.

The boron compound preferably has the formula $R^a_x NH_{4-x} BR^b_4$, $R^a_x PH_{4-x} BR^b_4$, $R^a_3 CBR^b_4$ or $BR^b_3$, where x is from 1 to 4, preferably 3, the radicals $R^a$ are identical or different, preferably identical, and are $C_1–C_{10}$-alkyl or $C_8–C_{18}$-aryl or two radicals $R^a$ together with the atoms connecting them form a ring, and the radicals $R^b$ are identical or different, preferably identical, and are $C_6–C_{18}$-aryl which may be substituted by alkyl, haloalkyl or fluorine. In particular, $R^a$ is ethyl, propyl, butyl or phenyl and $R^b$ is phenyl, pentafluorophenyl, 3,5-bistrifluoromethylphenyl, mesityl, xylyl or tolyl (EP 277 003, EP 277 004 and EP 426 638).

As cocatalyst, preference is given to using an aluminum compound such as aluminoxane and/or an aluminum alkyl.

The cocatalyst used is particularly preferably an aluminoxane, in particular of the formula C for the linear type and/or the formula D for the cyclic type,

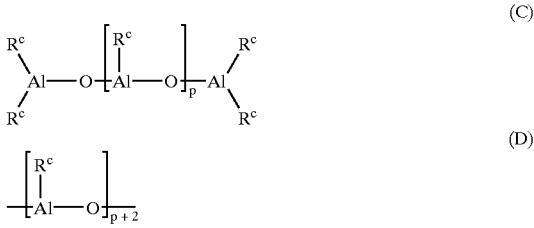

where, in the formulae C and D, the radicals $R^C$ are identical or different and are each hydrogen or a $C_1–C_{20}$-hydrocarbon group such as a $C_1–C_{18}$-alkyl group, a $C_6–C_{18}$-aryl group or benzyl, and p is an integer from 2 to 50, preferably from 10 to 35.

Preferably, the radicals $R^C$ are identical and are hydrogen, methyl, isobutyl, phenyl or benzyl, particularly preferably methyl.

If the radicals $R^C$ are different, they are preferably methyl and hydrogen or alternatively methyl and isobutyl, with hydrogen or isobutyl preferably being present in a numerical proportion of from 0.01 to 40% (of the radicals $R^C$).

The methods of preparing the aluminoxanes are known. The precise spatial structure of the aluminoxanes is not known (J. Am. Chem. Soc. (1993) 115, 4971). For example, it is conceivable that chains and rings are joined to form larger two-dimensional or three-dimensional structures.

Regardless of the method of preparation, all aluminoxane solutions have in common a variable content of unreacted aluminum starting compound which is present in free form or as adduct.

It is possible to preactivate the metallocene compound with a cocatalyst, in particular an aluminoxane, before use in the polymerization reaction. This significantly increases the polymerization activity. The preactivation of the metallocene compound is preferably carried out in solution. Here, the metallocene compound is preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The metallocene can be used in the same concentration but it is preferably used in an amount of from $10^{-4}$ to 1 mol per mol of aluminoxane. The preactivation time is from 5 minutes to 60 hours, preferably from 5 to 60 minutes. The preactivation is carried out at from −78 to 100° C., preferably from 0 to 80° C.

The metallocene compound is preferably employed in a concentration, based on the transition metal, of from $10^{-3}$ to $10^{-8}$ mol, preferably from $10^{-4}$ to $10^{-7}$ mol, of transition metal per dm$^3$ of solvent or per dm$^3$ of reactor volume. The aluminoxane is preferably used in a concentration of from $10^{-6}$ to $10^{-1}$ mol, preferably from $10^{-5}$ to $10^{-2}$ mol, per dm$^3$ of solvent or per dm$^3$ of reactor volume. The other cocatalysts mentioned are used in approximately equimolar amounts to the metallocene compound. However, higher concentrations are also possible in principle.

The aluminoxane can be prepared in various ways by known methods. One of the methods is, for example, reacting an aluminum-hydrocarbon compound and/or a hydridoaluminum-hydrocarbon compound with water (gaseous, solid, liquid or bound—for example as water of crystallization) in an inert solvent (for example toluene). To prepare an aluminoxane having different radicals $R^C$, for example, two different aluminum trialkyls corresponding to the desired composition are reacted with water.

To remove catalyst poisons present in the olefin, a purification step using an aluminum compound, preferably an aluminum alkyl such as trimethylaluminum or triethylaluminum, is advantageous. This purification can be carried out either in the polymerization system itself or the olefin is brought into contact with the aluminum compound and subsequently separated off again before addition to the polymerization system.

As molar mass regulator and/or to increase the catalyst activity, hydrogen can be added in the process of the present invention. This makes it possible to obtain low molecular weight polyolefins such as waxes.

In the process of the present invention, the metallocene compound is preferably reacted with the cocatalyst outside the polymerization reactor in a separate step using a suitable solvent. In this step, the catalyst can be applied to a support.

In the process of the present invention, a prepolymerization can be carried out by means of the metallocene compound. The prepolymerization is preferably carried out using the (or one of the) olefin(s) used in the polymerization.

The catalyst used in the process of the present invention can be supported. The application to a support enables, for example, the particle morphology of the polyolefin prepared to be controlled.

Here, the metallocene compound can be reacted first with the support and subsequently with the cocatalyst. The cocatalyst can also be supported first and subsequently reacted with the metallocene compound. It is also possible to apply the reaction product of metallocene compound and cocatalyst to a support. Suitable support materials are, for example, silica gels, aluminum oxides, solid aluminoxane or other inorganic support materials such as magnesium chloride. Another suitable support material is a polyolefin powder in finely divided form. The supported cocatalyst can be prepared, for example, as described in EP 567 952.

Preferably, the cocatalyst, eg. aluminoxane, is applied to a support such as silica gels, aluminum oxides, solid aluminoxane, other inorganic support materials or else a polyolefin powder in finely divided form and then reacted with the metallocene.

As inorganic supports, it is possible to use oxides which have been produced flame-pyrolytically by combustion of element halides in a hydrogen/oxygen flame or can be prepared as silica gels having particular particle size distributions and particle shapes.

The preparation of the supported cocatalyst can be carried out, for example, as described in EP 578 838 in the following manner in a stainless steel reactor having an explosion-proof design with a pumped circulation system and a pressure rating of 60 bar, with inert gas supply, temperature control by means of jacket cooling and a second cooling circuit via a heat exchanger on the pumped circulation system. The pumped circulation system draws in the reactor contents via a connection in the bottom of the reactor by means of a pump and pushes it into a mixer and through a riser line via a heat exchanger back into the reactor. The mixer is configured such that in the inlet there is located a constricted tube cross section where the flow velocity is increased and into the turbulence zone of which there is introduced, axially and opposite to the flow direction, a thin feed line through which, pulsed, a defined amount of water under 40 bar of argon can be fed in. The reaction is monitored by means of a sampler on the pumped circulation system.

However, other reactors are also suitable in principle.

The above-described reactor having a volume of 16 dm$^3$ is charged with 5 dm$^3$ of decane under inert conditions. 0.5 dm$^3$ (=5.2 mol) of trimethylaluminum are added at 25° C. 250 g of silica gel SD 3216-30 (Grace AG), which have been dried beforehand at 120° C. in an argon-fluidized bed, are then introduced into the reactor through a solids funnel and are homogeneously distributed by means of the stirrer and the pumped circulation system. A total amount of 76.5 g of water is added to the reactor in portions of 0.1 cm$^3$ every 15 seconds over a period of 3.25 hours. The pressure, caused by the argon and the gases evolved, is kept constant at 10 bar by means of a pressure regulation valve. After all the water has been introduced, the pumped circulation system is switched off and stirring is continued for another 5 hours at: 25° C.

The supported cocatalyst prepared in this way is used as a 10% strength suspension in n-decane. The aluminum content is 1.06 mmol of Al per cm$^3$ of suspension. The isolated solid contains 31% by weight of aluminum and the suspension medium contains 0.1% by weight of aluminum.

Further possible ways of preparing a supported cocatalyst are described in EP 578 838.

The metallocene of the present invention is then applied to the; supported cocatalyst by stirring the dissolved metallocene with the supported cocatalyst. The solvent is removed and replaced by a hydrocarbon in which both cocatalyst and the metallocene are insoluble.

The reaction to form the supported catalyst system is carried out at from −20 to +120° C., preferably from 0 to 100° C., particularly preferably from 15 to 40° C. The metallocene is reacted with the supported cocatalyst by combining the cocatalyst as a suspension having a concentration of from 1 to 40% by weight, preferably from 5 to 20% by weight, in an aliphatic, inert suspension medium such as n-decane, hexane, heptane or diesel oil with a solution of the metallocene in an inert solvent such as toluene, hexane, heptane or dichloromethane or with the finely milled solid metallocene. Conversely, a solution of the metallocene can also: be reacted with the solid cocatalyst.

The reaction is carried out by intensive mixing, for example by: stirring, at a molar Al/M$^1$ ratio of from 100/1 to 10,000/1, preferably from 100/1 to 3000/1, and a reaction time of from 5 to 120 minutes, preferably from 10 to 60 minutes, particularly preferably from 10 to 30 minutes, under inert conditions. During the reaction time for preparing the supported catalyst system, particularly when using the metallocenes of the present invention having absorption maxima in the visible region, changes occur in the color of the reaction mixture and these enable the progress of the reaction to be followed.

After the reaction time has expired, the supernatant solution is separated off, for example by filtration or decantation. The remaining solid is washed from 1 to 5 times with an inert suspension medium such as toluene, n-decane, hexane, diesel oil or dichloromethane to remove soluble constituents in the catalyst formed, in particular to remove unreacted and therefore soluble metallocene.

The supported catalyst system prepared in this way can be resuspended as vacuum-dried powder or while still moist with solvent and metered into the polymerization system as a suspension in one of the abovementioned inert suspension media.

If the polymerization is carried out as a suspension or solution polymerization, an inert solvent customary for the Ziegler low-pressure process is used. For example, the polymerization is carried out in an aliphatic or cycloaliphatic hydrocarbon, for example propane, butane, hexane, heptane, isooctane, cyclohexane or methylcyclohexane. It is also possible to use a petroleum or hydrogenated diesel oil fraction. Toluene can also be used. Preference is given to carrying out the polymerization in the liquid monomer.

Before addition of the catalyst, in particular the supported catalyst system (comprising the metallocene of the present invention and a supported cocatalyst), it is possible to introduce, in addition, another aluminum alkyl compound such as trimethylaluminum, triethylaluminum, triisobutylaluminum, trioctylaluminum or isoprenylaluminum into the reactor to make the polymerization system inert (for example to remove catalyst poisons present in the olefin). This is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents. This makes it possible to select a small molar Al/M$^1$ ratio in the synthesis of a supported catalyst system. If inert solvents are used, the monomers are metered in in gaseous or liquid form.

The following abbreviations are used in the present application:

| | |
|---|---|
| acac | acetylacetonate |
| 9-BBN | 9-borabicyclo[3.3.1]nonane |
| Bn | benzyl |
| Bu | butyl |
| i-Bu | isobutyl |
| $^t$BU | tertiary butyl |
| COD | 1,5-cyclooctadiene |
| dba | dibenzylideneacetone |
| DBU | 1,8-diazabicyclo[5.4.0]undec-7-ene |
| diglyme | diethylene glycol dimethyl ether |
| DME | 1,2-dimethoxyethane |
| DMF | dimethylformamide |
| dppe | 1,2-bis (diphenylphosphino) ethane |
| dppf | 1,1'-bis (diphenylphosphino) ferrocene |
| dppp | 1,3-bis (diphenylphosphino) propane |
| Et | ethyl |
| HMPA | hexamethylphosphoramide |
| Me | methyl |
| MTBE | methyl tert-butyl ether |
| NMP | N-methyl-2-pyrrolidinone |
| nonaflate | nonafluorobutylsulfonate |

-continued

| OAc | acetate |
| --- | --- |
| Ph | phenyl |
| PTE | periodic Table of the Elements |
| Tf | trifluoromethanesulfonate |
| THF | tetrahydrofuran |
| TMSCl | trimethylsilyl chloride |
| triflate | trifluoromethanesulfonate |
| triglyme | triethylene glycol dimethyl ether |

EXAMPLES

The invention is illustrated by the following examples which do not restrict the scope of the invention.

1. 7-Chloro-2-methyl-1-indanone (1)

50 g (0.3 mol) of 2-chloropropiophenone (B. L. Jenson et al., Tetrahedron, 1978, 1627) together with 24.55 ml (0.33) of 37% strength formaldehyde solution were placed in the reaction vessel. A solution of 12 g of sodium hydroxide in 600 ml of water was added thereto. The mixture was stirred for 2.5 hours at 40° C. The phases were separated, the aqueous phase was extracted 3 times with 50 ml each time of methylene chloride, the combined organic phases were washed with 100 ml of 1N HCl solution and dried over magnesium sulfate. The methylene chloride solution was added while stirring to 400 g of hot (65° C.) concentrated sulfuric acid over a period of 2.25 hours. The methylene chloride distilled off during this procedure. After the addition was complete, stirring was continued for another 0.5 hour at 65° C. At room temperature, the cool sulfuric acid solution was slowly added to an ice-cold mixture of 325 ml of methylene chloride and 325 ml of water. The phases were separated, the sulfuric acid solution was extracted twice with 250 ml each time of methylene chloride, the combined organic phases were washed with 200 ml of saturated sodium hydrogencarbonate solution, 200 ml of water and 200 ml of saturated sodium chloride solution and dried over magnesium sulfate. After removal of the solvent, the brown liquid was distilled via a 10 cm Vigreux column with column head under a full oil pump vacuum. This gave 39.6 g of (1) as a pale yellow liquid which slowly crystallized.

B.p.: 95–98° C (0.3–0.25 mbar); m.p.: 42–43° C.; $^1$H-NMR (300 MHz, CDCl$_3$): 7.41 (t, 1H), 7.28 (m, 1H), 7.22 (m, 1H), 3.31 (m, 1H), 2.59–2.27 (m, 2H), 1.25 (d, J =7.3 Hz, 3H).

2. 7-Bromo-2-methyl-1-indanone (2)

Using a method similar to Example 1, 57.2 g of (2) were obtained as solid from 78.2 g (0.37 mol) of 2-bromopropiophenone (S. Wang et al., J. Org. Chem., 1989, 54, 5364).

M.p.: 55–61° C.; $^1$H-NMR (300 MHz, CDCl$_3$): 7.50 (1H), 7.37 (2H), 3.34 (m, 1H), 2.9–2.6 (m, 2H), 1.3 (d, 3H).

3. 2-Methyl-7-trifluoromethanesulfonoxy-1-indanone (3)

16.2 g (0.1 mol) of 7-hydroxy-2-methyl-1-indanone (G. Bringmann et al., Liebigs Ann. Chem., 1985, 2116) together with 20 ml of dry pyridine in 150 ml of dry methylene chloride were placed in the reaction vessel. At −78° C., 20 ml (0.12 mol) of trifluoromethanesulfonic anhydride were added and the mixture was slowly warmed to 0° C. on an ice bath. The reaction mixture was stirred for 16 hours at 20° C., subsequently diluted with 750 ml of ether, the precipitated pyridinium salt was filtered off, the ether phase was washed twice with 100 ml each time of 2N hydrochloric acid, twice with 100 ml each time of water and once with 200 ml of saturated sodium chloride solution and dried over magnesium sulfate. After removal of the solvent, the residue was chromatographed on silica gel using heptane/ethyl acetate (9:1). 27.1 g of (3) were obtained.

$^1$H-NMR (300 MHz, CDCl$_3$): 7.5–7.3 (3H), 3.3 (m, 1H), 2.7–2.4 (m, 2H), 1.3 (d, 3H).

4. 7-Iodo-2-methyl-1-indanone (4)

Using a method similar to Example 2, 12.8 g of (4) as solid were obtained (the cyclization was carried out in polyphosphoric acid instead of in sulfuric acid) from 30.6 g (0.118 mol) of 2-iodopropiophenone (as described by S. Wang et al., J. Org. Chem., 1989, 54, 5364; but the ethyl Grignard was converted into the cuprate by addition of CuI).

$^1$H-NMR (300 MHz, CDCl$_3$): 7.50–7.30 (3H), 3.3 (m, 1H), 2.9–2.6 (m, 2H), 1.3 (d, 3H).

5. 7-Chloro-2-butyl-1-indanone (5)

Using a method similar to U.S. Pat. No. 5,489,712 or A. Bhattacharya, Synthetic Communications, 1996, 26, 1775, 18.5 g of (5) were obtained from 32.0 g (0.15 mol) of 2-chlorophenyl pentyl ketone (preparation similar to that of 2-chloropropiophenone).

$^1$H-NMR (300 MHz, CDCl$_3$): 7.5–7.4 (1H), 7.35–7.1 (2H), 3.3–3.1 (1H), 2.8–2.7 (1H), 2.7–2.5 (2H), 2.0–1.8 (1H), 1.55–1.2 (5H), 0.9 (t, 3H).

6. 7-Chloro-2-cyclohexyl-1-indanone (6)

Using a method similar to U.S. Pat. No. 5,489,712 or A. Bhattacharya, Synthetic Communications, 1996, 26, 1775, 14 g of 7-chloro-2-cyclohexyl-1-indanone (6) were obtained from 20.0 g (0.085 mol) of 2-chlorophenyl methylcyclohexyl ketone (preparation similar to that of 2-chloropropiophenone).

$^1$H-NMR (300 MHz, CDCl$_3$): 7.47–7.25 (3H), 3.11 (dd, 1H), 2.92 (dd, 1H), 2.65 (m, 1H), 2.10–1.98 (m, 1H), 1.80–1.60 (m, 4H), 1.46–1.0 (m, 6H).

7. 7-Chloro-2-phenyl-1-indanone (7)

Using a method similar to Example 5, 14.5 g of (7) were obtained from 23.0 g (0.1 mol) of benzyl 2-chlorophenyl ketone (preparation similar to that of 7-chloropropiophenone).

8. 7-Bromo-2-isopropyl-1-indanone (8)

Using a method similar to Example 5, 32.8 g of (8) were obtained from 48.2 g (0.2 mol) of 2-bromophenyl 2-methylpropyl ketone (preparation similar to that of 7-bromopropiophenone).

9. 7-Bromo-2-(2-methylpropyl)-1-indanone (9)

Using a method similar to Example 5, 15.7 g of (9) were obtained from 25.5 g (0.1 mol) of 2-bromophenyl 3-methylbutyl ketone (preparation similar to that of 7-bromopropiophenone).

10. 7-Bromo-5-fluoro-2-methyl-1-indanone (10)

Using a method similar to Example 2, 7.1 g of (10) were obtained from 15 g (0.065 mol) of 2-bromo-4-fluoropropiophenone.

11. 5,7-Dichloro-2-methyl-1-indanone (11)

Using a method similar to Example 1, 26.42 g of (11) were obtained from 50 g (0.246 mol) of 2,4-dichloropropiophenone.

12. 6,7-Dichloro-2-methyl-1-indanone (12)

Using a method similar to Example 1, 23.3 g of (12) were obtained from 40 g (0.197 mol) of 2,3-dichloropropiophenone.

13. 7-Bromo-2,6-dimethyl-1-indanone (13)

Using a method similar to Example 2, 6.8 g of (13) were obtained from 10 g (0.044 mol) of 2-bromo-3-methylpropiophenone.

14. 7-Chloro-2-methyl-5-trifluoromethyl-1-indanone (14)

Using a method similar to Example 1, 4.5 g of (14) were obtained from 16 g (0.067 mol) of 2-chloro-4-trifluoromethylpropiophenone.

15. 2-Methyl-7-phenyl-1-indanone (15)

a) 22.5 g (0.1 mol) of 7-bromo-2-methyl-1-indanone (2), 13.4 g (0.11 mol) of phenylboronic acid and 23.3 g (0.22 mol) of sodium carbonate were placed in 380 ml of dimethoxyethane and 120 ml of water in the reaction vessel, the mixture was degassed a number of times and saturated with argon. 450 mg (2 mmol) of palladium acetate and 1.05 g (4 mmol) of triphenylphosphine (TPP) were added and the reaction mixture was stirred for 2 hours at 80° C. After addition of 300 ml of water, the mixture was extracted 3 times with 250 ml each time of diethyl ether, the ether phase was washed twice with 100 ml each time of water and dried over magnesium sulfate. Removal of the solvent gave 21.1 g of (15) as solid.
M.p.: 81.5–83° C.; $^1$H-NMR (300 MHz, CDCl$_3$): 7.6 (t, 1H), 7.5–7.3 (m, 6H), 7.25 (1H), 3.4 (m, 1H), 2.8–2.6 (m, 2H), 1.3 (d, 3H).

b) 2.5 g (13.8 mmol) of 7-chloro-2-methyl-1-indanone (1), 2.11 g (17.3 mmol) of phenylboronic acid and 3.66 g (34.6 mmol) of sodium carbonate were placed in 40 ml of o-xylene/5 ml of water in the reaction vessel, the mixture was degassed a number of times and saturated with argon. After addition of 1.55 mg (0.0069 mmol) of palladium acetate and 7.3 mg (0.027 mmol) of triphenylphosphine, the reaction mixture was stirred for 8 hours at 100° C. After 2, 4 and 6 hours, the same amount of palladium acetate and triphenylphosphine were added again each time. After addition of 40 ml of water, the phases were separated, the aqueous phase was extracted 3 times with 40 ml each time of ether, the combined organic phases were washed with 40 ml of water and 40 ml of saturated sodium chloride solution and dried over magnesium sulfate. Removal of the solvent gave 2.9 g of (15) as solid. The $^1$H-NMR indicated a conversion of about 85%.

c) 0.9 g (5 mmol) of (1), 0.73 g (6 mmol) of phenylboronic acid and 1.32 g (12.5 mmol) of sodium carbonate were placed in 15 ml of ethylene glycol/3 ml of water in the reaction vessel, the mixture was degassed a number of times and saturated with argon. After addition of 33.7 mg (0.15 mmol) of palladium acetate and 0.34 g (0.6 mmol) of (m-NaO$_3$S-phenyl)$_3$phosphine (TMSPP), the reaction mixture was stirred for 5 hours at 125° C. After addition of 20 ml of water, the aqueous phase was extracted 5 times with 30 ml each time of ether, the combined ether phases were washed with 40 ml of water and 40 ml of saturated sodium chloride solution and dried over magnesium sulfate. Removal of the solvent gave 0.76 g of (15) as solid.

16. 2-Methyl-7-(1-naphthyl)1-indanone (16)

a) Using a method similar to Example 15a), 56.3 g (0.25 mol) of 7-bromo-2-methyl-1-indanone (2), 47.3 g (0.275 mol) of 1-naphthylboronic acid and 58 g (0.55 mol) of sodium carbonate were placed in 950 ml of dimethoxyethane and 300 ml of water in the reaction vessel, the mixture was degassed a number of times and saturated with argon. 560 mg (2.5 mmol) of palladium acetate and 1.31 g (5 mmol) of triphenylphosphine (TPP) were added and the reaction mixture was stirred for 2 hours at 80° C. After addition of 700 ml of water, the mixture was extracted 5 times with 300 ml each time of diethyl ether, the ether phase was washed twice with 300 ml each time of water and with 300 ml of saturated sodium chloride solution and dried over magnesium sulfate. Removal of the solvent gave 63.3 g of (16) as solid.
M.p: 104–105° C.; $^1$H-NMR (300 MHz, CDCl$_3$): 7.9 (d, 2H), 7.65 (m, 1H), 7.6–7.25 (m, 7H), 3.5 (m, 1H), 2.9–2.6 (m, 2H), 1.25 (d, 3H).

b) Using a method similar to Example 15b), 2.5 g (13.8 mmol) of 7-chloro-2-methyl-1-indanone (1), 2.97 g (17.3 mmol) of naphthylboronic acid and 3.66 g (34.6 mmol) of sodium carbonate were placed in 40 ml of o-xylene/5 ml of water in the reaction vessel, the mixture was degassed a number of times and saturated with argon. After addition of 1.55 mg (0.0069 mmol) of palladium acetate and 7.3 mg (0.027 mmol) of triphenylphosphine, the reaction mixture was stirred for 8 hours at 100° C. After 2, 4 and 6 hours, the same amount of palladium acetate and triphenyl phosphine were added again each time. After addition of 40 ml of water, the phases were separated, the aqueous phase was extracted 3 times with 40 ml each time of ether, the combined organic phases were washed with 40 ml of water and 40 ml of saturated sodium chloride solution and dried over magnesium sulfate. Removal of the solvent gave 3.26 g of (16) as solid.

c) 2.5 g (13.8 mmol) of 7-chloro-2-methyl-1-indanone (1), 2.86 g (16.6 mmol) of naphthylboronic acid, 0.22 g (0.68 mmol) of tetrabutylammonium bromide and 3.66 g (34.6 mmol) of sodium carbonate were placed in 40 ml of o-xylene in the reaction vessel, the mixture was degassed a number of times and saturated with argon. After addition of 1.55 mg (0.0069 mmol) of palladium acetate and 7.3 mg (0.027 mmol) of triphenylphosphine, the reaction mixture was stirred for 9 hours at 125° C. After addition of 40 ml of water, the phases were separated, the aqueous phase was extracted 3 times with 40 ml each time of ether, the combined organic phases were washed with 40 ml of water and 40 ml of saturated sodium chloride solution and dried over magnesium sulfate. Removal of the solvent gave 3.38 g of (16) as solid.

d) Using a method similar to Example 15c), 2.5 g (13.84 mmol) of (1), 2.86 g (16.6 mmol) of naphthylboronic acid and 3.66 g (34.6 mmol) of sodium carbonate were placed in 41 ml of ethylene glycol/8.3 ml of water in the reaction vessel, the mixture was degassed a number of times and saturated with argon. After addition of 1 mg (0.0046 mmol) of palladium acetate and 10.4 mg (0.0184 mmol) of TMSPP, the reaction mixture was stirred for 5 hours at 125° C. The aqueous phase was extracted twice with 50 ml each time of ether, the combined ether phases were washed with 40 ml of water and 40 ml of saturated sodium chloride solution and dried over magnesium sulfate. Removal of the solvent gave 3.08 g of (16) as solid.

17. 7-(3,5-Dimethylphenyl)-2-methyl-1-indanone (17)

Using a method similar to Example 16b), 16.25 g (0.09 mol) of (1), 14.85 g (0.1 mol) of 3,5-dimethylphenylboronic acid, 21.2 g (0.2 mol) of sodium carbonate were placed in 240 ml of o-xylene/80 ml of water in the reaction vessel, the mixture was degassed a number of times and saturated with argon. After addition of 101 mg (0.45 mmol) of palladium acetate and 472 mg (1.8 mmol) of TPP, the reaction mixture was stirred for 8 hours at 100° C. After 2, 4 and 6 hours, the same amounts of palladium acetate and triphenylphosphine were added again each time. After addition of 150 ml of water, the phases were separated, the aqueous phase was extracted 3 times with 200 ml each time of ether, the combined organic phases were washed with 200 ml of water and 200 ml of saturated sodium chloride solution and dried over magnesium sulfate. Removal of the solvent gave 20.3 g of (17) as an oil.

$^1$H-NMR (300 MHz, CDCl$_3$): 7.55 (t, 1H), 7.4 (m, 1H), 7.23 (1H), 7.05 (m, 2H), 7.02 (1H), 3.34 (m, 1H), 2.78–2.64 (m, 2H), 2.35 (s, 6H), 1.27 (d, 3H).

18. 7-(3,5-bis(Trifluoromethyl)phenyl)-2-methyl-1-indanone (18)

Using a method similar to Example 15a), 6.75 g (0.03 mol) of (2), 8.5 g (0.033 mol) of 3,5-bis(trifluoromethyl)phenylboronic acid and 7.0 g (0.066 mol) of sodium carbonate were placed in 120 ml of dimethoxyethane and 36 ml of water in the reaction vessel, the mixture was degassed a number of times and saturated with argon. 120 mg (0.5 mmol) of palladium acetate and 282 mg (1.1 mmol) of TPP were added and the reaction mixture was stirred for 2 hours at 80° C. After addition of 150 ml of water, the mixture was extracted 3 times with 150 ml each time of diethyl ether, the combined ether phases were washed 3 times with 150 ml each time of water and dried over magnesium sulfate. Removal of the solvent gave 9.93 g of (18) as an oil.

$^1$H-NMR (300 MHz, CDCl$_3$): 7.9 (s, 2H), 7.66 (t, 1H), 7.53 (dd, 1H), 7.3–7.24 (2H), 3.46 (m, 1H), 2.83–2.70 (m, 2H), 1.29 (d, 3H).

19. 2-Methyl-7-(2-naphthyl)1-indanone (19)

Using a method similar to Example 16d), 2.16 g (0.012 mol) of (1), 2.27 g (0.0132 mol) of 2-naphthylboronic acid, 2.8 g (0.0264 mol) of sodium carbonate were placed in 40 ml of ethylene glycol/8 ml of water in the reaction vessel, the mixture was degassed a number of times and saturated with argon. After addition of 13.5 mg (0.06 mmol) of palladium acetate and 0.102 g (0.18 mmol) of TMSPP, the reaction mixture was stirred for 2 hours at 125° C. After addition of 40 ml of water, the aqueous phase was extracted 4 times with 50 ml each time of ether, the combined ether phases were washed with 50 ml of water and 50 ml of saturated sodium chloride solution and dried over magnesium sulfate. Removal of the solvent gave 3.0 g of (19) as an oil which tends to crystallize.

$^1$H-NMR (300 MHz, CDCl$_3$): 7.92 (m, 4H), 7.62 (2H), 7.56–7.49 (m, 2H), 7.46 (dd, 1H), 7.39 (d, 1H), 3.45 (m, 1H), 2.84–2.68 (m, 2H), 2.35 (s, 6H), 1.33 (d, 3H).

20. 7-(4-Methoxyphenyl)-2-methyl-1-indanone (20)

Using a method similar to Example 16d), 3.84 g (0.021 mol) of (1), 3.58 g (0.024 mol) of 4-methoxyphenylboronic acid, 4.98 g (0.047 mol) of sodium carbonate were placed in 60 ml of ethylene glycol/10 ml of water in the reaction vessel, the mixture was degassed a number of times and saturated with argon. After addition of 23.9 mg (0.106 mmol) of palladium acetate and 0.12 g (0.21 mmol) of TMSPP, the reaction mixture was stirred for 2 hours at 125° C. After addition of 60 ml of water, the aqueous phase was extracted 4 times with 60 ml each time of ether, the combined ether phases were washed with 60 ml of water and 60 ml of saturated sodium chloride solution and dried over magnesium sulfate. Removal of the solvent gave 3.75 g of (20) as an oil.

$^1$H-NMR (300 MHz, CDCl$_3$): 7.55 (t, 1H), 7.40 (m, 2H), 7.36 (m, 1H), 7.24 (m, 1H), 6.94 (m, 2H), 3.84 (s, 3H), 3.39 (m, 1B), 2.77–2.63 (m, 2H), 1.28 (d, 3H).

21. 2-Methyl-7-(4-methylphenyl)-1-indanone (21)

Using a method similar to Example 16d), 3.61 g (0.020 mol) of (1), 3.0 g (0.022 mol) of 4-methylphenylboronic acid, 4.66 g (0.044 mol) of sodium carbonate were placed in 60 ml of ethylene glycol/12 ml of water in the reaction vessel, the mixture was degassed a number of times and saturated with argon. After addition of 22.4 mg (0.1 mmol) of palladium acetate and 0.114 g (0.2 mmol) of TMSPP, the reaction mixture was stirred for 2 hours at 125° C. After addition of 60 ml of water, the aqueous phase was extracted 4 times with 50 ml each time of ether, the combined ether phases were washed with 50 ml of water and 50 ml of saturated sodium chloride solution and dried over magnesium sulfate. Removal of the solvent gave 4.5 g of (21) as solid.

$^1$H-NMR (300 MHz, CDCl$_3$): 7.56 (t, 1H), 7.42–7.14 (m, 6H), 3.40 (m, 1H), 2.78–2.64 (m, 2H), 2.40 (s, 3H), 1.28 (d, 3H).

22. 2-Methyl-7-(2-thienyl)-1-indanone (22)

Using a method similar to Example 15a), 11.25 g (0.05 mol) of (2), 13.4 g (0.055 mol) of thiophenylboronic acid and 11.7 g (0.11 mol) of sodium carbonate were placed in 190 ml of dimethoxyethane and 60 ml of water in the reaction vessel, the mixture was degassed a number of times and saturated with argon. 225 mg (1 mmol) of palladium acetate and 0.609 g (2 mmol) of tris(o-tolylphenyl)phosphine were added and the reaction mixture was stirred for 2 hours at 80° C. After addition of 150 ml of water, the mixture was extracted 4 times with 100 ml each time of diethyl ether, the ether phase was washed twice with 50 ml each time of water and dried over magnesium sulfate. Removal of the solvent gave 8.6 g of (22) as an oil.

$^1$H-NMR (300 MHz, CDCl$_3$): 7.6 (t, 1H), 7.5–7.3 (m, 6H), 7.25 (1H), 3.4 (m, 1H), 2.8–2.6 (m, 2H), 1.3 (d, 3H).

23. 2-Methyl-7-(2-furanyl)-1-indanone (23)

Using a method similar to Example 22, 33.7 g (0.15 mol) of (2), 18.5 g (0.165 mol) of furanylboronic acid and 34.9 g (0.33 mol) of sodium carbonate were placed in 570 ml of dimethoxyethane and 180 ml of water in the reaction vessel, the mixture was degassed a number of times and saturated with argon. 675 mg (3 mmol) of palladium acetate and 1.83 g (6 mmol) of tris(o-tolylphenyl)phosphine were added and the reaction mixture was stirred for 2 hours at 80° C. After addition of 450 ml of water, the mixture was extracted 4 times with 300 ml each time of diethyl ether, the ether phase was washed twice with 200 ml each time of water and dried over magnesium sulfate. Removal of the solvent gave 27.06 g of (23) as an oil.

¹H-NMR (300 MHz, CDCl₃): 7.86 (m, 2H), 7.57 (t, 1H), 7.51 (m, 1H), 7.4–7.2 (m, 2H), 3.37 (m, 1H), 2.78–2.66 (m, 2H), 1.32 (d, 3H).

24. 2-Methyl-7-(2-pyridyl)-1-indanone (24)

16.9 g (75 mmol) of (2) and 20 g (90 mmol) of 2-trimethylstannylpyridine were placed in 165 ml of tetrahydrofuran in the reaction vessel, the mixture was degassed a number of times and saturated with argon. 350 mg (0.37 mmol) of trans-di(μ-acetato)bis[o-(di-o-tolylphosphino)benzyl]dipalladium (II) were added and the reaction mixture was refluxed for 24 hours. After addition of 200 ml of water, the mixture was extracted 4 times with 150 ml each time of diethyl ether, the ether phase was washed with 100 ml of water and 100 ml of saturated sodium chloride solution and dried over magnesium sulfate. Removal of the solvent and drying for 24 hours at 0.1 mbar at 60° C. (removal of the trimethylstannyl bromide) gave 15.07 g of (24) as an oil.

¹H-NMR (300 MHz, CDCl₃): 8.66 (m, 1H), 7.66–7.20 (5H), 3.40 (m, 1H), 2.78–2.64 (m, 2H), 1.25 (d, 3H).

25. 2-Methyl-7-(2-methylphenyl)-1-indanone (25)

Using a method similar to Example 16d), 2.0 g (0.011 mol) of (1), 1.82 g (0.013 mol) of 2-methylphenylboronic acid and 2.6 g (24.6 mmol) of sodium carbonate were placed in 55 ml of ethylene glycol/5 ml of water in the reaction vessel, the mixture was degassed a number of times and saturated with argon. After addition of 18 mg (0.09 mmol) of palladium acetate and 0.15 g (0.27 mmol) of TMSPP, the reaction mixture was stirred for 2 hours at 125° C. After addition of 60 ml of water, the aqueous phase was extracted 4 times with 60 ml each time of ether, the combined ether phases were washed with 60 ml of water and 60 ml of saturated sodium chloride solution and dried over magnesium sulfate. Removal of the solvent gave 2.1 g of 2-methyl-7-(2-methylphenyl)-1-indanone as solid.

¹H-NMR (300 MHz, CDCl₃): 7.66–7.10 (m, 7H), 3.48 (m, 1H), 2.86–2.64 (m, 2H), 2.13/2.11 (s, 3H, stereoisomers), 1.33/1.29 (d, 3H, stereoisomers).

26. 2-Methyl-7-(4-dimethylaminophenyl)-1-indanone (26)

Using a method similar to Example 22, 8.0 g (0.032 mol) of (2), 5.85 g (0.038 mol) of 4-dimethylaminophenylboronic acid and 7.4 g (0.07 mol) of sodium carbonate were placed in 122 ml of dimethoxyethane and 37 ml of water in the reaction vessel, the mixture was degassed a number of times and saturated with argon. 142 mg (0.6 mmol) of palladium acetate and 385 mg (1.3 mmol) of tris(o-tolylphenyl)phosphine were added and the reaction mixture was stirred for 4 hours at 80° C. After addition of 150 ml of water, the mixture was extracted 4 times with 100 ml each time of diethyl ether, the ether phase was washed twice with 50 ml each time of water and dried over magnesium sulfate. Removal of the solvent and column filtration through neutral aluminum oxide (dichloromethane) gave 6.5 g of 2-methyl-7-(4-dimethylaminophenyl)-1-indanone as an oil.

¹H-NMR (300 MHz, CDCl₃): 7.58–7.24 (m, 5H), 6.78 (d, 2H), 3.38 (m, 1H), 3.01 (s, 6H), 2.78–2.65 (m, 2H), 1.28 (d, 2H).

27. 2-Methyl-7-(2,3-dimethylphenyl)-1-indanone (27)

Using a method similar to Example 16d), 2.0 g (0.011 mol) of (1), 1.95 g (0.013 mol) of 2,3-dimethylphenylboronic acid and 2.6 g (24.6 mmol) of sodium carbonate were placed in 55 ml of ethylene glycol/5 ml of water in the reaction vessel, the mixture was degassed a number of times and saturated with argon. After addition of 18 mg (0.09 mmol) of palladium acetate and 0.15 g (0.27 mmol) of TMSPP, the reaction mixture was stirred for 2 hours at 125° C. After addition of 60 ml of water, the aqueous phase was extracted 4 times with 60 ml each time of ether, the combined ether phases were washed with 60 ml of water and 60 ml of saturated sodium chloride solution and dried over magnesium sulfate. Removal of the solvent gave 2.9 g of 2-methyl-7-(2,3-dimethylphenyl)-1-indanone as solid.

¹H-NMR (300 MHz, CDCl₃): 7.61–6.92 (m, 6H), 3.40 (m, 1H), 2.80–2.60 (m, 2H), 2.34/2.32 (s, 3H, stereoisomers), 1.97/1.93 (s, 3H,: stereoisomers), 1.26/1.23 (d, 3H, stereoisomers).

28. 2-Methyl-7-(4-vinylphenyl)-1-indanone (28)

Using a method similar to Example 16d), 2.0 g (0.011 mol) of (1), 1.92 g (0.013 mol) of 4-styreneboronic acid and 2.6 g (24.6 mmol) of sodium carbonate were placed in 55 ml of ethylene glycol/5 ml of water in the reaction vessel, the mixture was degassed a number of times and saturated with argon. After addition of 18 mg (0.09 mmol) of palladium acetate and 0.15 g (0.27 mmol) of TMSPP, the reaction mixture was stirred for 2 hours at 125° C. After addition of 60 ml of water, the aqueous phase was extracted 4 times with 60 ml each time of ether, the combined ether phases were washed with 60 ml of water and 60 ml of saturated sodium chloride solution and dried over magnesium sulfate. Removal of the solvent gave 2.2 g of 2-methyl-7-(4-vinylphenyl)-1-indanone.

¹H-NMR (300 MHz, CDCl₃): 7.60–7.26 (m, 7H), 6.78 (dd, 1H), 5.81 (d, 1H)., 5.28 (d, 1H), 3.42 (m, 1H), 2.80–2.67 (m, 2H), 1.31 (d, 3H).

29. 2-Methyl-7-(4-trifluoromethylphenyl)-1-indanone (29)

Using a method similar to Example 16d), 6.28 g (0.035 mol) of (1), 7.6 g (0.040 mol) of 4-trifluoromethylphenylboronic acid and 8.16 g (77.3 mmol) of sodium carbonate were placed in 160 ml of ethylene glycol/17 ml of water in the reaction vessel, the mixture was degassed a number of times and saturated with argon. After addition of 57 mg (0.283 mmol) of palladium acetate and 0.47 g (0.848 mmol) of TMSPP, the reaction mixture was stirred for 2 hours at 125° C. After addition of 170 ml of water, the aqueous phase was extracted 4 times with 100 ml each time of ether, the combined ether phases were washed with 60 ml of water and 60 ml of saturated sodium chloride solution and dried over magnesium sulfate. Removal of the solvent gave 9.54 g of 2-methyl-7-(4-trifluoromethylphenyl)-1-indanone.

¹H-NMR (300 MHz, CDCl₃): 7.80–7.26 (m, 7H), 3.42 (m, 1H), 2.80–2.67 (m, 2H), 1.31 (d, 3H).

30. 2-Methyl-7-(4-biphenyl)-1-indanone (30)

Using a method similar to Example 15a), 6.75 g (0.03 mol) of (2), 6.53 g (0.033 mol) of 4-biphenylphenylboronic acid and 7.0 g (0.066 mol) of sodium carbonate were placed in 120 ml of dimethoxyethane and 36 ml of water in the reaction vessel, the mixture was degassed a number of times and saturated with argon. 120 mg (0.5 mmol) of palladium acetate and 282 mg (1.1 mmol) of TPP were added and the reaction mixture was stirred for 2 hours at 80° C. After addition of 150 ml of water, the mixture was extracted 3 times with 150 ml each time of diethyl ether, the combined ether phases were washed 3 times with 150 ml each time of water and dried over magnesium sulfate. Removal of the solvent gave 7.78 g of 2-methyl-7-(4-biphenyl)-1-indanone.

$^1$H-NMR (300 MHz, CDCl$_3$): 7.67–7.14 (12H), 3.49–3.37 (m, 1H), 2.80–2.67 (m, 2H), 1.30 (d, 3H).

31. 2-Methyl-7-(4-tert-butylphenyl)-1-indanone (31)

Using a method similar to Example 16d), 2.0 g (0.011 mol) of (1), 2.31 g (0.013 mol) of 4-tert-butylphenylboronic acid and 2.6 g (24.6 mmol) of sodium carbonate were placed in 55 ml of ethylene glycol/5 ml of water in the reaction vessel, the mixture was degassed a number of times and saturated with argon. After addition of 18 mg (0.09 mmol) of palladium acetate and 0.15 g (0.27 mmol) of TMSPP, the reaction mixture was stirred for 2 hours at 125° C. After addition of 60 ml of water, the aqueous phase was extracted 4 times with 60 ml each time of ether, the combined ether phases were washed with 60 ml of water and 60 ml of saturated sodium chloride solution and dried over magnesium sulfate. Removal of the solvent gave 2.8 g of 2-methyl-7-(4-tert-butylphenyl)-1-indanone.

$^1$H-NMR (300 MHz, CDCl$_3$): 7.60–7.26 (m, 7H), 3.42 (m, 1H), 2.80–2.67 (m, 2H), 1.31 (9H), 1.28 (d, 3H).

32. 2-Methyl-7-(3,5-difluorophenyl)-1-indanone (32)

2.25 g (0.01 mol) of 7-bromo-2-methyl-1-indanone (2), 1.74 g (0.011 mol) of 3,5-difluorophenylboronic acid and 2.33 g (0.022 mol) of sodium carbonate were placed in 38 ml of dimethoxyethane and 12 ml of water in the reaction vessel, the mixture was degassed a number of times and saturated with argon. 45 mg (0.2 mmol) of palladium acetate and 0.1 g (0.4 mmol) of triphenylphosphine (TPP) were added and the reaction mixture was stirred for 2 hours at 80° C. After addition of 50 ml of water, the mixture was extracted 3 times with 30 ml each time of diethyl ether, the ether phase was washed twice with water and dried over magnesium sulfate. Removal of the solvent gave 2.4 g of 2-methyl-7-(3,5-difluorophenyl)-1-indanone as solid.

$^1$H-NMR (300 MHz, CDCl$_3$): 7.62–7.31 (m, 6H), 3.43 (m, 1H), 2.8–2.6 (m, 2H), 1.29 (d, 3H).

33. 2-Butyl-7-phenyl-1-indanone (33)

Using a method similar to Example 16d), 10.02 g (0.045 mol) of 2-butyl-7-chloro-1-indanone, 6.58 g (0.054 mol) of phenylboronic acid and 11.9 g (0.122 mol) of sodium carbonate were placed in 135 ml of ethylene glycol/27 ml of water in the reaction vessel, the mixture was degassed a number of times and saturated with argon. After addition of 5 mg (0.022 mmol) of palladium acetate and 0.051 g (0.09 mmol) of TMSPP, the reaction mixture was stirred for 5 hours at 125° C. After addition of 120 ml of water, the aqueous phase was extracted 4 times with 100 ml each time of ether, the combined ether phases were washed with 50 ml of water and 50 ml of saturated sodium chloride solution and dried over magnesium sulfate. Removal of the solvent gave 12.0 g of (33) as an oil.

$^1$H-NMR (300 MHz, CDCl$_3$): 7.58 (t, 1H), 7.47–7.35 (6H), 7.28–7.23 (1H), 3.34 (dd, 1H), 2.83 (dd, 1H), 2.65 (m, 1H), 1.94 (m, 1H), 1.41 (m, 5H), 0.91 (t, 3H).

34. 2-Butyl-7-(1-naphthyl)1-indanone (34)

Using a method similar to Example 16d), 10.02 g (0.045 mol) of 2-butyl-7-chloro-1-indanone, 10.06 g (0.0585 mol) of 1-naphthylboronic acid and 11.9 g (0.122 mol) of sodium carbonate were placed in 135 ml of ethylene glycol/27 ml of water in the reaction vessel, the mixture was degassed a number of times and saturated with argon. After addition of 5 mg (0.022 mmol) of palladium acetate and 0.051 g (0.09 mmol) of TMSPP, the reaction mixture was stirred for 5 hours at 125° C. After addition of 120 ml of water, the aqueous phase was extracted 4 times with 100 ml each time of ether, the combined ether phases were washed with 50 ml of water and 50 ml of saturated sodium chloride solution and dried over magnesium sulfate. Removal of the solvent gave 12.2 g of (34) as an oil.

$^1$H-NMR (300 MHz, CDCl$_3$): 7.93 (d, 2H), 7.71–7.20 (8H), 3.39 (m, 1H), 2.92 (m, 1H), 2.64 (m, 1H), 1.88 (m, 1H), 1.41 (m, 5H), 0.93 (t, 3H).

35. 2-Cyclohexyl-7-phenyl-1-indanone (35)

Using a method similar to Example 16d), 2.73 g (0.011 mol) of 2-cyclohexyl-7-chloro-1-indanone, 1.59 g (0.013 mol) of phenylboronic acid and 2.6 g (24.6 mmol) of sodium carbonate were placed in 55 ml of ethylene glycol/5 ml of water in the reaction vessel, the mixture was degassed a number of times and saturated with argon. After addition of 18 mg (0.09 mmol) of palladium acetate and 0.15 g (0.27 mmol) of TMSPP, the reaction mixture was stirred for 2 hours at 125° C. After addition of 60 ml of water, the aqueous phase was extracted 4 times with 60 ml each time of ether, the combined ether phases were washed with 60 ml of water and 60 ml of saturated sodium chloride solution and dried over magnesium sulfate. Removal of the solvent gave 2.9 g of 2-cyclohexyl-7-phenyl-1-indanone.

$^1$H-NMR (300 MHz, CDCl$_3$): 7.60–7.16 (m, 8H), 3.11 (dd, 1H), 2.92 (dd, 1H), 2.65 (m, 1H), 2.10–1.98 (m, 1H), 1.80–1.60 (m, 4H), 1.46–1.0 (m, 6H).

36. 2-Cyclohexyl-7-(1-naphthyl)1-indanone (36)

Using a method similar to Example 16d), 2.73 g (0.011 mol) of 2-cyclohexyl-7-chloro-1-indanone, 2.24 g (0.013 mol) of naphthylboronic acid and 2.6 g (24.6 mmol) of sodium carbonate were placed in 55 ml of ethylene glycol/5 ml of water in the reaction vessel, the mixture was degassed a number of times and saturated with argon. After addition of 18 mg (0.09 mmol) of palladium acetate and 0.15 g (0.27 mmol) of TMSPP, the reaction mixture was stirred for 2 hours at 125° C. After addition of 60 ml of water, the aqueous phase was extracted 4 times with 60 ml each time of ether, the combined ether phases were washed with 60 ml of water and 60 ml of saturated sodium chloride solution and dried over magnesium sulfate. Removal of the solvent gave 3.0 g of 2-cyclohexyl-7-(1-naphthyl)1-indanone.

$^1$H-NMR (300 MHz, CDCl$_3$): 7.92–7.20 (10H), 3.11 (dd, 1H), 2.92 (dd, 1H), 2.65 (m, 1H), 2.10–1.98 (m, 1H), 1.80–1.60 (m, 4H), 1.46–1.0 (m, 6H).

37. 2-Methyl-4-(1-naphthyl)indene (37)

1.3 g (33 mmol) of sodium borohydride were added at 0° C. to a solution of 12 g (44 mmol) of (16) in 100 ml of THF/methanol 2:1 and the mixture was stirred for 18 hours at room temperature. The reaction mixture was poured onto 100 g of ice, concentrated hydrochloric acid was added until the pH was 1 and the mixture as extracted a number of times with diethyl ether. The combined organic phases were washed with saturated aqueous sodium hydrogen carbonate solution, water and saturated aqueous sodium chloride solution and dried over magnesium sulfate. The crude product was taken up in 200 ml of toluene, admixed with 0.5 g of p-toluenesulfonic acid and refluxed for 2 hours on a water separator. The reaction mixture was washed 3 times with 509 ml each time of saturated sodium hydrogen carbonate solution and the solvent was removed under reduced pressure. The solid residue was washed with a little pentane and dried under reduced pressure. This gave 10.3 g of (37) in the form of colorless crystals. m.p. 143° C.; $^1$H-NMR (300 MHz, CDCl$_3$): 7.92–7.18 (10H), 6.11 (m, 1H), 3.42 (s, 2H), 2.07 (3H).

Using a method similar to Example 37, the following indenes were prepared:

38. 2-Methyl-4(or 7)-phenylindene (38)
39. 2-Methyl-4(or 7)-(4-methoxyphenyl)indene (39)
40. 2-Methyl-4(or 7)-(4-methylphenyl)indene (40)
41. 2-Methyl-4(or 7)-(2-methylphenyl)indene (41)
42. 2-Methyl-4(or 7)-(2,3-dimethylphenyl)indene (42)
43. 2-Methyl-4(or 7)-(3,5-bis(trifluoromethyl)phenyl)indene (43)
44. 2-Methyl-4(or 7)-(3,5-dimethylphenyl)indene (44)
45. 2-Methyl-4(or 7)-(3,5-difluorophenyl)indene (45)
46. 2-Methyl-4(or 7)-(2-naphthyl)indene (46)
47. 2-Methyl-4(or 7)-(4-N,N-dimethylaminophenyl)indene (47)
48. 2-Methyl-4(or 7)-(4-trifluoromethylphenyl)indene (48)
49. 2-Methyl-4(or 7)-(4-tert-butylphenyl)indene (49)
50. 2-Methyl-4(or 7)-(4-biphenyl)indene (50)
51. 2-Methyl-4(or 7)-(2-furanyl)indene (51)
52. 2-Methyl-4(or 7)-(2-thienyl)indene (52)
53. 2-Methyl-4(or 7)-(2-pyridyl)indene (53)
54. 2-Butyl-4(or 7)-phenylindene (54)
55. 2-Butyl-4(or 7)-(1-naphthyl)indene (55)
56. 2-Cyclohexyl-4(or 7)-phenylindene (56)
57. 2-Cyclohexyl-4(or 7)-(1-naphthyl)indene (57)

58. Dimethylsilanediylbis(2-methyl-4-(1-naphthyl)indenyl)zirconium Dichloride (58)

14.4 ml (50 mmol) of a 20% strength solution of butyllithium in toluene were added at room temperature to a solution of 10 g (38 mmol) of (37) in 100 ml of toluene and 5 ml of THF and the mixture was heated at 80° C. for 2 hours. The suspension was subsequently cooled to 0° C. and admixed with 2.5 g (19 mmol) of dimethyldichlorosilane. The reaction mixture was heated at 80° C. for another 1 hour and subsequently washed with 50 ml of water. The solvent was removed under reduced pressure and the residue was recrystallized from heptane at −20° C. 8.2 g of ligand were obtained as colorless crystals. 8.0 g (14 mmol) of the ligand were dissolved in 70 ml of diethyl ether, admixed at room temperature with 10.5 ml of a 20% strenght solution of butyllithium in toluene and subsequently refluxed for 3 hours. The solvent was removed under reduced pressure and the residue together with 50 ml of hexane was filtered on a G3 Schlenk frit, washed with 50 ml of hexane and dried (0.1 mbar, 20° C.). The dilithium salt was added at −78° C. to a suspension of 3.2 g (14 mmol) of zirconium tetrachloride in 80 ml of methylene chloride and, while stirring, warmed to room temperature over a period of 18 hours. The mixture was filtered on a G3 frit and the residue was extracted with a total of 400 ml of methylene chloride added a little at a time. The combined filtrates were very largely freed of solvent under reduced pressure. The crystals which precipitated from methylene chloride were isolated. This gave 1.5 g of (58) having a racemate:meso ratio of 1:1. Recrystallization from methylene chloride gave the racemic complex in the form of yellow crystals.

$^1$H-NMR (300 MHz, CDCl$_3$): 7.94–7.10 (m, 20H), 6.49 (s, 2H), 2.22 (s, 6H), 1.36 (6H).

59. Dimethylsilanediylbis(2-methyl-4-(3,5-bistrifluoromethyl)phenyl)indenyl)zirconium Dichloride (59)

Using a method similar to Example 58, 2-methyl-7-(3,5-bis(trifluoromethyl)phenyl)indene was converted into the corresponding dimethylsilyl-bridged zirconocene.

$^1$H-NMR (300 MHz, CDCl$_3$): 8.11–6.91 (m, 12H), 6.84/6.72 (s, 2H), 2.50/2.27 (s, 6H), 1.52–1.30 (m, 6H).

60. Dimethylsilanediylbis(2-methyl-4-(3,5-dimethylphenyl)indenyl)zirconium Dichloride (60)

Using a method similar to Example 58, 2-methyl-7-(3,5-dimethylphenyl)indene was converted into the corresponding dimethylsilyl-bridged zirconocene.

$^1$H-NMR (300 MHz, CDCl$_3$): 7.67–6.84 (m, 14H), 2.47–2.27 (m, 18H), 1.47–1.25 (m, 6H).

61. Dimethylsilanediylbis(2-methyl-4-(4-methoxyphenyl)indenyl)zirconium Dichloride (61)

Using a method similar to Example 58, 2-methyl-7-(4-methoxyphenyl)indene was converted into the corresponding dimethylsilyl-bridged zirconocene.

$^1$H-NMR (300 MHz, CDCl$_3$): 7.54–6.8 (m, 16H), 3.81 (s, 6H), 2.45–2.28 (m, 6H), 1.45–1.28 (m, 6H).

62. Dimethylsilanediylbis(2-methyl-4-(4-methylphenyl)indenyl)zirconium Dichloride (62)

Using a method similar to Example 58, 2-methyl-7-(4-methylphenyl)indene was converted into the corresponding dimethylsilyl-bridged zirconocene.

$^1$H-NMR (300 MHz, CDCl$_3$): 7.54–6.8 (m, 16H), 2.48–2.22 (m, 12H), 1.50–1.25 (m, 6H).

63. Dimethylsilanediylbis(2-methyl-4-(2-methylphenyl)indenyl)zirconium Dichloride (63)

Using a method similar to Example 58, 2-methyl-7-(2-methylphenyl)indene was converted into the corresponding dimethylsilyl-bridged zirconocene.

$^1$H-NMR (300 MHz, CDCl$_3$): 7.58–6.90 (m, 16H), 2.49–2.20 (m, 12H), 1.51–1.27 (m, 6H).

64. Dimethylsilanediylbis(2-methyl-4-(2-naphthyl)indenyl)zirconium Dichloride (64)

Using a method similar to Example 58, 2-methyl-7-(2-naphthyl)indene was converted into the corresponding dimethylsilyl-bridged zirconocene.

$^1$H-NMR (300 MHz, CDCl$_3$): 8.2–7.18 (m, 20H), 6.03 (s, 2H), 2.30 (s, 6H), 1.36 (6H).

65. Dimethylsilanediylbis(2-methyl-4-(4-tert-butylphenyl)indenyl)zirconium Dichloride (65)

Using a method similar to Example 58, 2-methyl-7-(4-tert-butylphenyl)indene was converted into the corresponding dimethylsilyl-bridged zirconocene.

$^1$H-NMR (300 MHz, CDCl$_3$): 7.54–6.8 (m, 16H), 2.48–2.22 (m, 6H), 1.50–1.25 (m, 6H), 1.32 (s, 18H).

66. Dimethylsilanediylbis(2-methyl-4-(2,3-dimethylphenyl)indenyl)zirconium Dichloride (66)

Using a method similar to Example 58, 2-methyl-7-(2,3-dimethylphenyl)indene was converted into the corresponding dimethylsilyl-bridged zirconocene.

$^1$H-NMR (300 MHz, CDCl$_3$): 7.54–6.8 (m, 16H), 2.48–2.22 (m, 6H), 1.50–1.25 (m, 6H).

67. Dimethylsilanediylbis(2-methyl-4-(4-trifluoromethylphenyl)indenyl)zirconium Dichloride (67)

Using a method similar to Example 58, 2-methyl-7-(4-trifluoromethylphenyl)indene was converted into the corresponding dimethylsilyl-bridged zirconocene.

$^1$H-NMR (300 MHz, CDCl$_3$): 7.75–6.88 (m, 16H), 2.50–2.27 (m, 6H), 1.49–1.22 (m, 6H).

68. Dimethylsilanediylbis(2-methyl-4-(3,5-difluorophenyl)indenyl)zirconium Dichloride (68)

Using a method similar to Example 58, 2-methyl-7-(3,5-difluorophenyl)indene was converted into the corresponding dimethylsilyl-bridged zirconocene.

$^1$H-NMR (300 MHz, CDCl$_3$): 7.54–6.8 (m, 16H), 2.48–2.22 (m, 6H), 1.50–1.25 (m, 6H).

69. Dimethylsilanediylbis(2-methyl-4-(4-biphenyl)indenyl)zirconium Dichloride (69)

Using a method similar to Example 58, 2-methyl-7-(4-biphenyl)indene was converted into the corresponding dimethylsilyl-bridged zirconocene.

$^1$H-NMR (300 MHz, CDCl$_3$): 7.76–7.03 (m, 26H), 2.28 (s, 6H), 1.37 (m, 6H).

70. Dimethylsilanediylbis(2-butyl-4-phenyl)indenyl)zirconium Dichloride (70)

Using a method similar to Example 58, 2-butyl-4-phenylindene was converted into the corresponding dimethylsilyl-bridged zirconocene.

$^1$H-NMR (300 MHz, CDCl$_3$): 7.70–6.80 (m, 18H), 2.75 (m, 4H), 1.6–1.3 (m, 8H), 1.49, 1.32, 1.22 (s, rac, meso, 6H), 0.91–0.82 (m, 6H).

71. Dimethylsilanediylbis(2-methyl-4-(4-dimethylaminophenyl)indenyl)zirconium Dichloride Using a method similar to Example 58, 2-methyl-4-(4-dimethylaminophenyl)indene was converted into the corresponding bridged zirconocene.

$^1$H-NMR (300 MHz, CDCl$_3$): 7.62–7.00 (m, 10H), 6.88–6.76 (m, 6H), 2.95 (s, 12H), 2.42 (s, 6H), 1.18 (s, 6H).

72. Dimethylsilanediylbis(2-cyclohexyl-4-phenyl)indenyl)zirconium Dichloride Using a method similar to Example 58, 2-cyclohexyl-4-phenylindene was converted into the corresponding bridged zirconocene.

$^1$H-NMR (300 MHz, CDCl$_3$): 7.65–7.06 (m, 16H), 6.92 (s, 2H), 2.88–2.75 (m, 2H), 2.00–0.95 (m, 20H), 138 (s, 6H).

We claim:

1. A process for the preparation of indanones of the formula II from indanones formula I or of indanones of the formula IIa from indanones of the formula Ia

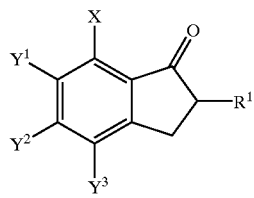

(I)

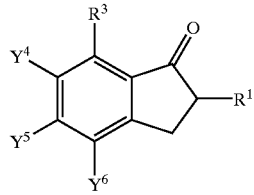

(II)

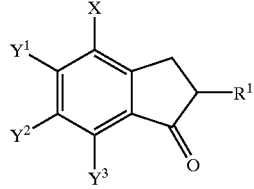

(Ia)

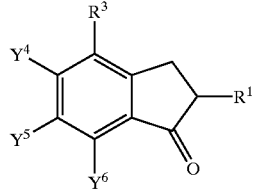

(IIa)

which comprises reacting an indanone of the formula I or Ia with a coupling component, where, in the formulae I, Ia, II and IIa, R$^1$ is a C$_1$–C$_{40}$-group which is bound via a carbon atom and may bear one or more identical or different heteroatom-containing radicals as substituents, or R$^1$ is an OR$^2$, SR$^2$, NR$^2_2$, PR$^2_2$, SiR$^2_3$ or OSiR$^2_3$ group, where R$^2$ are identical or different and are each a C$_1$–C$_{20}$-hydrocarbon group which may each bear one or more identical or different halogen, OH, OR$^2$, SR$^2$, NR$^2_2$—, PR$^2_2$—, —SiR$^2_3$ or —OSiR$^2_3$ substituents or two radicals R$^2$ may be joined to form a ring system, or R$^1$ is a C$_1$–C$_{20}$-heterocyclic group which is bound via a carbon atom and may in turn bear C$_1$–C$_{20}$-radicals or heteroatoms as substituents, X is a leaving group, R$^3$ is a C$_1$–C$_{40}$-hydrocarbon group which is bound via a carbon atom and may bear one or more identical or different heteroatom-containing radicals as substituents, or R$^3$ is a halogen atom or an NR$^2_2$, PR$^2_2$, B(OR$^2$)$_2$, SiR$^2_3$ or SnR$^2_3$ group, where R$^2$ are identical or different and are each a C$_1$–C$_{20}$-hydrocarbon group, which may each bear one or more identical or different halogen, OH, OR$^2$, SR$^2$, NR$^2_2$—, PR$^2_2$—, —SiR$^2_3$ or —OSiR$^2_3$ substituents, or two radicals R$^2$ may be joined to form a ring system, or R$^3$ is a C$_1$–C$_{20}$-heterocyclic group which is bound via a carbon atom and may in turn bear C$_1$–C$_{20}$-radicals or heteroatoms as substituents, Y$^1$, Y$^2$ and Y$^3$ are identical or different and are each a hydrogen atom or are as defined for X or R$^3$, and $Y^4$, $Y^5$ and $Y^6$ are identical or different and are each a hydrogen atom or are as defined for $R^3$.

2. A process as claimed in claim 1, wherein the reaction is carried out in a solvent.

3. A process as claimed in claim 1, wherein the reaction is carried out in the presence of a catalyst.

4. A process for preparing an indanone of the formula I as defined in claim 1, which comprises a) reacting an aryl alkyl ketone with aqueous formalin solution and an alkali metal carbonate or alkaline earth metal carbonate or an alkali hydroxide or alkaline earth metal hydroxide and b) carrying out the cyclization to the indanone under acid conditions.

5. The process of claim 1, in which in formulas (I), (II), (Ia) and (IIa), $R^1$ is selected from the group consisting of linear, branched or cyclic $C_1$–$C_{20}$-alkyl groups, which may bear one or more identical or different halogen, OH, $OR^2$, $SR^2$, $NR^2_2$—, $PR^2_2$—, —$SiR^2_3$ or —$OSiR^2_3$ substituents; $C_6$–$C_{22}$-aryl groups which may bear one or more identical or different halogen, OH, $OR^2$, $SR^2$, $NR^2_2$—, $PR^2_2$—, —$SiR^2_3$ or —$OSiR^2_3$ substituents; $C_7$–$C_{20}$-alkylaryl groups or $C_7$–$C_{20}$-arylalkyl groups, where the alkyl part may bear one or more identical or different halogen, OH, $OR^2$, $SR^2$, $NR^2_2$—, $PR^2_2$—, —$SiR^2_3$ or —$OSiR^2_3$ substituents and the aryl part may bear one or more identical or different halogen, OH, $OR^2$, $SR^2$, $NR^2_2$—, $PR^2_2$—, —$SiR^2_3$ or —$OSiR^2_3$ substituents; $C_2$–$C_{10}$-alkenyl groups, wich may bear one or more identical or different halogen, OH, $OR^2$, $SR^2$, $NR^2_2$—, $PR^2_2$—, —$SiR^2_3$ or —$OSiR^2_3$ substituents; $C_2$–$C_{20}$-alkynyl groups, which may bear one or more identical or different halogen, OH, $OR^2$, $SR^2$, $NR^2_2$—, $PR^2_2$—, —$SiR^2_3$ or —$OSiR^2_3$ substituents; $C_8$–$C_{12}$-arylalkenyl groups, where the alkenyl part may bear one or more identical or different halogen, OH, $OR^2$, $SR^2$, $NR^2_2$—, $PR^2_2$—, —$SiR^2_3$ or —$OSiR^2_3$ substituents and the aryl part may bear one or more identical or different halogen, OH, $OR^2$, $SR^2$, $NR^2_2$—, $PR^2_2$—, —$SiR^2_3$ or —$OSiR^2_3$ substituents, or $R^1$ is an $OR^2$, $SR^2$, $NR^2_2$, $PR^2_2$, $SiR^2_3$ or $OSiR^2_3$ group, where in each of the above instances $R^2$ are identical or different and are each a $C_1$–$C_{20}$-hydrocarbon group which may each bear one or more identical or different halogen, OH, $OR^2$, $SR^2$, $NR^2_2$—, $PR^2_2$—, —$SiR^2_3$ or —$OSiR^2_3$ substituents or two radicals $R^2$ may be joined to form a ring system, where $R^2$ is defined as above, or $R^1$ is a $C_1$–$C_{20}$-heterocyclic group which is bound via a carbon atom and may in turn bear $C_1$–$C_{20}$-radicals or heteroatoms as substituents, X is a leaving group selected from the group consisting of a diazonium group, a halogen atom or a $C_1$–$C_{40}$-group which is bound via a heteroatom, $R^3$ is selected from the group consisting of linear, branched or cyclic $C_1$–$C_{20}$-alkyl groups, which may bear one or more identical or different halogen, OH, $OR^2$, $SR^2$, $NR^2_2$—, $PR^2_2$—, —$SiR^2_3$ or —$OSiR^2_3$ substituents; $C_6$–$C_{22}$-aryl groups, which may bear one or more identical or different halogen, $OR^2$, $SR^2$, $NR^2_2$—, $NH_2$, —$N_2H_3$, $NO_2$, CN, $CO_2R^2$, CHO, $COR^2$, $PR^2_2$—, —$SiR^2_3$ or —$OSiR^2_3$ substituents; $C_7$–$C_{15}$-alkylaryl groups or $C_7$–$C_{15}$-arylalkyl groups, where the alkyl part may bear one or more identical or different halogen, OH, $OR^2$, $SR^2$, $NR^2_2$—, $PR^2_2$—, —$SiR^2_3$ or —$OSiR^2_3$ substituents and the aryl part may bear one or more identical or different halogen, $OR^2$, $SR^2$, $NR^2_2$—, $NH_2$, —$N_2H_3$, $NO_2$, CN, $CO_2R^2$, CHO, $COR^2$, $PR^2_2$—, —$SiR^2_3$ or —$OSiR^2_3$ substituents; $C_714$ $C_{15}$alkylarl groups or $C_7$–$C_{15}$-arylakyl groups, where the alkyl part may bear one or more identical or different halogen, OH, $OR^2$, $SR^2$, $NR^2_2$—, —$SiR^2_3$ or —$OSiR^2_3$ subsitituents and the arly part may bear one or more identical or different halogen, $OR^2$, $SR^2$, $NR^2_2$—$NH_2$, —$N_2H_3$, $NO_2$, CN, $CO_2R^2$, CHO, $PR^2_2$—, —$SiR^2_3$ or —$OSiR^2_3$ subtituents; $C_2$–$C_{10}$-alkenyl groups, which may bear one or more identical or different halogen, OH, $OR^2$, $CO_2R^2$, $COR^2$, $SR^2$, $NR^2_2$—, $PR^2_2$—, —$SiR^2_3$ or —$OSiR^2_3$ substituents; $C_2$–$C_{10}$-alkynyl groups, which may bear one or more identical or different halogen, OH, $OR^2$, $SR^2$, $NR^2_2$—, $PR^2_2$—, —$SiR^2_3$ or —$OSiR^2_3$ substituents; $C_8$–$C_{12}$-arylalkenyl groups, which may bear one or more identical or different halogen, OH, $OR^2$, $SR^2$, $NR^2_2$—, $PR^2_2$—, —$SiR^2_3$ or —$OSiR^2_3$ substituents, where $R^2$ is as defined above, or $R^3$ is a halogen atom or an $NR^2_2$, $PR^2_2$, $B(OR^2)_2$, $SiR^2_3$ or $SnR^2_3$ group, where $R^2$ are identical or different and are each a $C_1$–$C_{20}$-hydrocarbon group, which may each bear one or more identical or different halogen, OH, $OR^2$, $SR^2$, $NR^2_2$—, $PR^2_2$—, —$SiR^2_3$ or —$OSiR^2_3$ substituents, or two radicals $R^2$ may be joined to form a ring system, where $R^2$ is as defined above, or $R^3$ is a $C_1$–$C_{20}$-heterocyclic group which is bound via a carbon atom and may in turn bear $C_1$–$C_{20}$-radicals or heteroatoms as substituents, $Y^1$, $Y^2$ and $Y^3$ are identical or different and are each a hydrogen atom or are as defined for X or $R^3$, and $Y^4$, $Y^5$ and $Y^6$ are identical or different and are each a hydrogen atom or are as defined for $R^3$.

6. The process of claim 1, in which in formulas (I), (II), (Ia) and (IIa), $R^1$ is selected from the group consisting of linear, branched or cyclic $C_1$–$C_{20}$-alkyl groups, which may bear one or more identical or different halogen, OH, $OR^2$, $SR^2$, $NR^2_2$—, $PR^2_2$—, —$SiR^2_3$ or —$OSiR^2_3$ substituents; $C_6$–$C_{22}$-aryl groups which may bear one or more identical or different halogen, OH, $OR^2$, $SR^2$, $NR^2_2$—, $PR^2_2$—, —$SiR^2_3$ or —$OSiR^2_3$ substituents; $C_7$–$C_{20}$-alkylaryl groups or $C_7$–$C_{20}$-arylalkyl groups, where the alkyl part may bear one or more identical or different halogen, OH, $OR^2$, $SR^2$, $NR^2_2$—, $PR^2_2$—, —$SiR^2_3$ or —$OSiR^2_3$ substituents and the aryl part may bear one or more identical or different halogen, OH, $OR^2$, $SR^2$, $NR^2_2$—, $PR^2_2$—, —$SiR^2_3$ or —$OSiR^2_3$ substituents; $C_2$–$C_{10}$-alkenyl groups bear one or more identical or different halogen, OH, $OR^2$, $SR^2$, $NR^2_2$—, $PR^2_2$—, —$SiR^2_3$ or —$OSiR^2_3$ substituents; $C_2$–$C_{20}$-alkynyl groups, which may which may bear one or more identical or different halogen, OH, $OR^2$, $SR^2$, $NR^2_2$—, $PR^2_2$—, —$SiR^2_3$ or —$OSiR^2_3$ substituents; $C_8$–$C_{12}$-arylalkenyl groups, where the alkenyl part may bear one or more identical or different halogen, OH, $OR^2$, $SR^2$, $NR^2_2$—, $PR^2_2$—, —$SiR^2_3$ or —$OSiR^2_3$ substituents and the aryl part may bear one or more identical or different halogen, OH, $OR^2$, $SR^2$, $NR^2_2$—, $PR^2_2$—, —$SiR^2_3$ or —$OSiR^2_3$ substituents, or $R^1$ is an $OR^2$, $SR^2$, $NR^2_2$, $PR^2_2$, $SiR^2_3$ or $OSiR^2_3$ group, where in each of the above instances $R^2$ are identical or different and are each a $C_1$–$C_{20}$-hydrocarbon group which may each bear one or more identical or different halogen, OH, $OR^2$, $SR^2$, $NR^2_2$—, $PR^2_2$—, —$SiR^2_3$ or —OSiR$^2_3$ substituents or two radicals R$^2$ may be joined to form a ring system, where R$^2$ is defined as above, or R$^1$ is a C$_1$–C$_{20}$-heterocyclic group which is bound via a carbon atom and may in turn bear C$_1$–C$_{20}$-radicals or heteroatoms as substituents, X is a leaving group selected from the group consisting of a diazonium group, a halogen atom or a C$_1$–C$_{10}$-group which is bound via a heteroatom, selected from the group consisting of boron, silicon, tin, oxygen or sulfur, R$^3$ is selected from the group consisting of linear, branched or cyclic C$_1$–C$_{20}$-alkyl groups, which may bear one or more identical or different halogen, OH, OR$^2$, SR$^2$, NR$^2_2$—, PR$^2_2$—, —SiR$^2_3$ or —OSiR$^2_3$ substituents; C$_6$–C$_{22}$-aryl groups, which may bear one or more identical or different halogen, OR$^2$, SR$^2$, NR$^2_2$—, NH$_2$, —N$_2$H$_3$, NO$_2$, CN, CO$_2$R$^2$, CHO, COR$^2$, PR$^2_2$—, —SiR$^2_3$ or —OSiR$^2_3$ substituents; C$_7$–C$_{15}$-alkylaryl groups or C$_7$–C$_{15}$-arylalkyl groups, where the alkyl part may bear one or more identical or different halogen, OH, OR$^2$, SR$^2$, NR$^2_2$—, PR$^2_2$—, —SiR$^2_3$ or —OSiR$^2_3$ substituents and the aryl part may bear one or more identical or different halogen, OR$^2$, SR$^2$, NR$^2_2$—, NH$_2$, —N$_2$H$_3$, NO$_2$, CN, CO$_2$R$^2$, CHO, PR$^2_2$—, —SiR$^2_3$ or —OSiR$^2_3$ substituents; C$_2$–C$_{10}$-alkenyl groups, which may bear one or more identical or different halogen, OH, OR$^2$, CO$_2$R$^2$, COR$^2$, SR$^2$, NR$^2_2$—, PR$^2_2$—, —SiR$^2_3$ or —OSiR$^2_3$ substituents; C$_2$–C$_{10}$-alkynyl groups, which may bear one or more identical or different halogen, OH, OR$^2$, SR$^2$, NR$^2_2$—, PR$^2_2$—, —SiR$^2_3$ or —OSiR$^2_3$ substituents; C$_8$–C$_{12}$-arylalkenyl groups, which may bear one or more identical or different halogen, OH, OR$^2$, SR$^2$, NR$^2_2$—, PR$^2_2$—, —SiR$^2_3$ or —OSiR$^2_3$ substituents, where R$^2$ is as defined above, or R$^3$ is a halogen atom or an NR$^2_2$, PR$^2_2$, B(OR$^2$)$_2$, SiR$^2_3$ or SnR$^2_3$ group, where R$^2$ are identical or different and are each a C$_1$–C$_{20}$-hydrocarbon group, which may each bear one or more identical or different halogen, OH, OR$^2$, SR$^2$, NR$^2_2$—, PR$^2_2$—, —SiR$^2_3$ or —OSiR$^2_3$ substituents, or two radicals R$^2$ may be joined to form a ring system, where R$^2$ is as defined above, or R$^3$ is a C$_1$–C$_{20}$-heterocyclic group which is bound via a carbon atom and may in turn bear C$_1$–C$_{20}$-radicals or heteroatoms as substituents, Y$^1$, Y$^2$ and Y$^3$ are identical or different and are each a hydrogen atom or are as defined for X or R$^3$, and Y$^4$, Y$^5$ and Y$^6$ are identical or different and are each a hydrogen atom or are as defined for R$^3$.

7. The process of claim 1, in which in formulas (I), (II), (Ia) and (IIa),

R$^1$ is selected from the group consisting of linear, branched or cyclic C$_1$–C$_{20}$-alkyl groups, which may bear one or more identical or different halogen, OH, OR$^2$, SR$^2$, NR$^2_2$—, PR$^2_2$—, —SiR$^2_3$ or —OSiR$^2_3$ substituents; C$_6$–C$_{22}$-aryl groups which may bear one or more identical or different halogen, OH, OR$^2$, SR$^2$, NR$^2_2$—, PR$^2_2$—, —SiR$^2_3$ or —OSiR$^2_3$ subtituents; C$_7$–C$_{20}$-alkylaryl groups or C$_7$–C$_{20}$-arylalkyl groups, where the alkyl part may bear one or more identical or different halogen, OH, OR$^2$, SR$^2$, NR$^2_2$—, PR$^2_2$—, —SiR$^2_3$ or —OSiR$^2_3$ substituents and the aryl part may bear one or more identical or different halogen, OH, OR$^2$, SR$^2$, NR$^2_2$—, PR$^2_2$—, —SiR$^2_3$ or —OSiR$^2_3$ substituents; C$_2$–C$_{10}$-alkenyl groups, which may bear one or more identical or different halogen, OH, OR$^2$, SR$^2$, NR$^2_2$—, PR$^2_2$—, —SiR$^2_3$ or —OSiR$^2_3$ substitu-ents; C$_2$–C$_{20}$-alkynyl groups, which may bear one or more identical or different halogen, OH, OR$^2$, SR$^2$, NR$^2_2$—, PR$^2_2$—, —SiR$^2_3$ or —OSiR$^2_3$ substituents; C$_8$–C$_{12}$-arylalkenyl groups, where the alkenyl part may bear one or more identical or different halogen, OH, OR$^2$, SR$^2$, NR$^2_2$—, PR$^2_2$—, —SiR$^2_3$ or —OSiR$^2_3$ substituents and the aryl part may bear one or more identical or different halogen, OH, OR$^2$, SR$^2$, NR$^2_2$—, PR$^2_2$—, —SiR$^2_3$ or —OSiR$^2_3$ substituents, or R$^1$ is an OR$^2$, SR$^2$, NR$^2_2$, PR$^2_2$, SiR$^2_3$ or OSiR$^2_3$ group, where in each of the above instances R$^2$ are identical or different and are each a C$_1$–C$_{20}$-hydrocarbon group which may each bear one or more identical or different halogen, OH, OR$^2$, SR$^2$, NR$^2_2$—, PR$^2_2$—, —SiR$^2_3$ or —OSiR$^2_3$ substituents or two radicals R$^2$ may be joined to form a ring system, where R$^2$ is defined as above, or R$^1$ is a C$_1$–C$_{20}$-heterocyclic group which is bound via a carbon atom and may in turn bear C$_1$–C$_{20}$-radicals or heteroatoms as substituents, x is a leaving group selected from the group consisting of a diazonium group, a halogen atom, C$_1$–C$_{40}$-alkylsulfonate, C$_1$–C$_{40}$-haloalkylsulfonate, C$_6$–C$_{40}$-arylsulfonate, C$_6$–C$_{40}$-halo-arylsulfonate, C$_7$–C$_{40}$-arylalkylsulfonate, C$_7$–C$_{40}$-haloaryl-alkylsulfonate, C$_1$–C$_{40}$-alkylcarboxylate, C$_1$–C$_{40}$-haloalkylcarboxylate, C$_6$–C$_{40}$-arylcarboxylate, C$_6$–C$_{40}$-haloarylcarbbxylate, C$_7$–C$_{40}$-arylalkylcarboxylate, C$_7$–C$_{40}$-haloarylalkylcarboxylate, formate, C$_1$–C$_{40}$-alkyl carbonate, C$_1$–C$_{40}$-haloalkyl carbonate, C$_6$–C$_{40}$-aryl carbonate, C$_6$–C$_{40}$-haloaryl carbonate, C$_7$–C$_{40}$-arylalkyl carbonate, C$_7$–C$_{40}$-haloarylalkyl carbonate, C$_1$–C$_{40}$-alkyl phosphonate, C$_1$–C$_{40}$-haloalkyl phosphonate, C$_6$–C$_{40}$-aryl phosphonate, C$_6$–C$_{40}$-haloaryl phosphonate, C$_7$–C$_{40}$-arylalkyl phosphonate and C$_7$–C$_{40}$-haloarylalkyl phosphonate, R$^3$ is selected from the group consisting of linear, branched or cyclic C$_1$–C$_{20}$-alkyl groups, which may bear one or more identical or different halogen, OH, OR$^2$, SR$^2$, NR$^2_2$—, PR$^2_2$—, —SiR$^2_3$ or —OSiR$^2_3$ substituents; C$_6$–C$_{22}$-aryl groups, which may bear one or more identical or different halogen, OR$^2$, SR$^2$, NR$^2_2$—, NH$_2$, —N$_2$H$_3$, NO$_2$, CN, CO$_2$R$^2$, CHO, COR$^2$, PR$^2_2$—, —SiR$^2_3$ or —OSiR$^2_3$ substituents; C$_7$–C$_{15}$-alkylaryl groups or C$_7$–C$_{15}$-arylalkyl groups, where the alkyl part may bear one or more identical or different halogen, OH, OR$^2$, SR$^2$, NR$^2_2$—, PR$^2_2$—, —SiR$^2_3$ or —OSiR$^2_3$ substituents and the aryl part may bear one or more identical or different halogen, OR$^2$, SR$^2$, NR$^2_2$—, NH$_2$, —N$_2$H$_3$, NO$_2$, CN, CO$_2$R$^2$, CHO PR$^2_2$—, —SiR$^2_3$ or —OSiR$^2_3$ substituents; C$_2$–C$_{10}$-alkenyl groups, which may bear one or more identical or different halogen, OH, OR$^2$, CO$_2$R$^2$, COR$^2$, SR$^2$, NR$^2_2$—, PR$^2_2$—, —SiR$^2_3$ or —OSiR$^2_3$ substituents; C$_2$–C$_{10}$-alkynyl groups, which may bear one or more identical or different halogen, OH, OR$^2$, SR$^2$, NR$^2_2$—, PR$^2_2$—, —SiR$^2_3$ or —OSiR$^2_3$ substituents; C$_8$–C$_{12}$-arylalkenyl groups, which may bear one or more identical or different halogen, OH, OR$^2$, SR$^2$, NR$^2_2$—, PR$^2_2$—, —SiR$^2_3$ or —OSiR$^2_3$ substituents, where R$^2$ is as defined above, or R$^3$ is a halogen atom or an NR$^2_2$, PR$^2_2$, B(OR$^2$)$_2$, SiR$^2_3$ or SnR$^2_3$ group, where R$^2$ are identical or different and are each a C$_1$–C$_{20}$-hydrocarbon group, which may each bear one or more identical or different halogen, OH, OR$^2$, SR$^2$, NR$^2_2$—, PR$^2_2$—, —SiR$^2_3$ or —OSiR$^2_3$ substituents, or two radicals R² may be joined to form a ring system, where R² is as defined above, or R³ is a $C_1$–$C_{20}$-heterocyclic group which is bound via a carbon atom and may in turn bear $C_1$–$C_{20}$-radicals or heteroatoms as substituents, $Y^1$, $Y^2$ and $Y^3$ are identical or different and are each a hydrogen atom or are as defined for X or $R^3$, and $Y^4$, $Y^5$ and $Y^6$ are identical or different and are each a hydrogen atom or are as defined for $R^3$.

8. An indanone of the formula III,

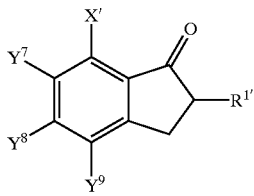
(III)

where

X' is chlorine, bromine, iodine, triflate or mesylate $R^1$ is a linear, branched or cyclic $C_1$—$C_8$—alkyl group $Y^9$ and $Y^7$ are hydrogen atoms and $Y^8$ is a hydrogen atom or as defined for X'.

9. An indanone of the formula IV,

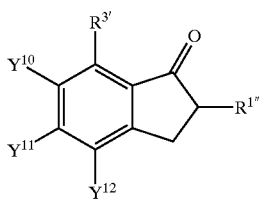
(IV)

where $R^{1'}$ is a linear, branched or cyclic $C_1$—$C_{20}$—alkyl group, $R^{3'}$ is a $C_6$—$C_{14}$—aryl group or a $C_7$—$C_{15}$—alkylaryl group, $Y^{10}$ or $Y^{12}$ are hydrogen atoms and $Y^{11}$ or $Y^{11}$ is a $C_6$—$C_{14}$—aryl or a $C_7$—$C_{10}$—alkylaryl group.

10. A metallocene compound of the formula VI

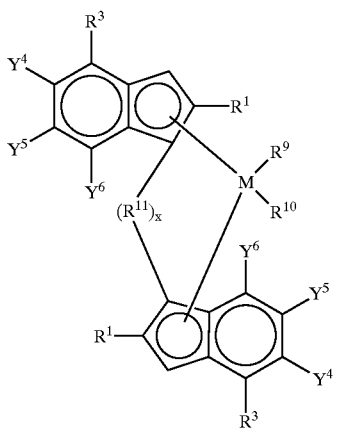
(VI)

where $R^1$ is a linear, branched or cyclic $C_1$–$C_8$-alkyl group which may bear one or more identical or different fluorine or chlorine substituents, a phenyl group which may bear one or more identical or different fluorine or chlorine substituents, a $C_7$–$C_{12}$-alkylaryl or arylalkyl group, where the alkyl part may bear one or more identical or different fluorine or chlorine substituents and the aryl part may bear one or more identical or different fluorine or chlorine substituents, a $C_2$–$C_8$-alkenyl group or a $C_2$–$C_8$-alkynyl group, a $C_8$–$C_{12}$-arylalkenyl group which may bear one or more identical or different fluorine or chlorine substituents, or $R^1$ is an $OR^2$, $SiR^2_3$ or —$OSiR^2_3$ group, where $R^2$ are identical or different and are each a $C_1$–$C_4$-alkyl group or phenyl group or $R^1$ is a $C_1$–$C_{16}$-heterocyclic group, where the heteroatoms are oxygen, nitrogen, sulfur or silicon and the group may in turn bear $C_1$–$C_{10}$-radicals or heteroatoms as substituents, M is titanium, zirconium or hafnium, $R^9$ and $R^{10}$ are identical or different and are each a hydrogen atom, hydroxy or a halogen atom or a $C_1$–$C_{40}$-group such as $C_1$–$C_{10}$-alkyl, $C_1$–$C_{10}$-alkoxy, $C_6$–$C_{10}$-aryl, $C_6$–$C_{10}$-aryloxy, $C_2$–$C_{10}$-alkenyl, $C_7$–$C_{40}$-arylalkyl, $C_7$–$C_{40}$-alkylaryl, $C_8$–$C_{40}$-arylalkenyl, preferably hydrogen, $C_1$–$C_3$-alkyl, in particular methyl, $C_1$–$C_3$-alkoxy, $C_6$-aryl, $C_6$-aryloxy, $C_2$–$C_{10}$-alkenyl, $C_7$–$C_{10}$-arylalkyl, $C_7$–$C_{10}$-alkylaryl, $C_8$–$C_{10}$-arylalkenyl or a halogen atom, x is zero or 1, $R^3$ is 4-($C_4$–$C_8$-alkyl)phenyl, where the 4-($C_4$–$C_8$-alkyl) group is a branched $C_4$–$C_8$-alkyl group, $Y^4$ and $Y^6$ are each a hydrogen atom and $Y^5$ is a hydrogen atom or $R^3$, $R^{11}$ is a bridging group of the formula

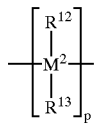

where $M^2$ is carbon, silicon, germanium or tin, p is 1, 2 or 3, $R^{12}$ and $R^{13}$ are identical or different and are each a hydrogen atom, a halogen atom or $C_1$–$C_{20}$-alkyl, $C_6$–$C_{14}$-aryl, $C_1$–$C_{10}$-alkoxy, $C_2$–$C_{10}$-alkenyl, $C_7$–$C_{20}$-arylalkyl, $C_7$–$C_{20}$-alkylaryl, $C_6$–$C_{10}$-aryloxy, $C_1$–$C_{10}$-fluoroalkyl, $C_6$–$C_{10}$-haloaryl or $C_2$–$C_{10}$-alkynyl or $R^{12}$ and $R^{13}$ together with the atom connecting them form a ring.

11. A metallocene compound of the formula VI as claimed in claim 10, wherein M is zirconium and $R^1$ is a linear, branched or cyclic $C_1$–$C_8$-alkyl group.

12. A metallocene compound of the formula VI as claimed in claim 10 wherein

M is zirconium, $R^1$ is methyl, ethyl, isopropyl, n-butyl and sec.-butyl, $Y^4$, $Y^5$ and $Y^6$ are hydrogen, $R^3$ is 4-(tert.-butyl)phenyl, $R^{11}$ is dimethylsilyl, diphenylsilyl or methylphenylsilyl and x=1.

13. An indene of the formula (V) or (Va)

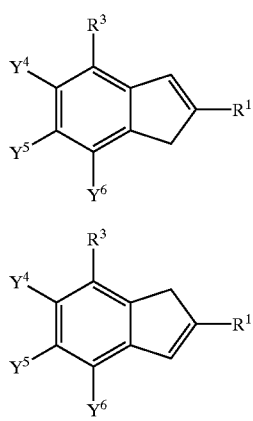

where $R^1$ is a linear, branched or cyclic $C_1-C_8$-alkyl group which may bear one or more identical or different fluorine or chlorine substituents, a phenyl group which may bear one or more identical or different fluorine or chlorine substituents, a $C_7-C_{12}$-alkylaryl or arylalkyl group, where the alkyl part may bear one or more identical or different fluorine or chlorine substituents and the aryl part may bear one or more identical or different fluorine or chlorine substituents, a $C_2-C_8$-alkenyl group or a $C_2-C_8$-alkynyl group, a $C_8-C_{12}$-arylalkenyl group which may bear one or more identical or different fluorine or chlorine substituents, or $R^1$ is an $OR^2$, $SiR^2_3$ or $-OSiR^2_3$ group, where $R^2$ are identical or different and are each a $C_1-C_4$-alkyl group or phenyl group or $R^1$ is a $C_1-C_{16}$-heterocyclic group, where the heteroatoms are oxygen, nitrogen, sulfur or silicon and the group may in turn bear $C_1-C_{10}$-radicals or heteroatoms as substituents, titanium, zirconium, hafnium, $R^3$ is 4-($C_4-C_8$-alkyl)phenyl, where the 4-($C_4-C_8$-alkyl) group is a branched $C_4-C_8$-alkyl group, $Y^4$ and $Y^6$ are each a hydrogen atom and $Y^5$ is a hydrogen atom or $R^3$.

14. The indene of claim 13, wherein $R^1$ is a linear, branched or cyclic $C_1-C_8$-alkyl group, $Y^4$ and $Y^6$ are each a hydrogen atom and $Y^5$ is a hydrogen atom or $R^3$.

15. The indene of claim 13, wherein

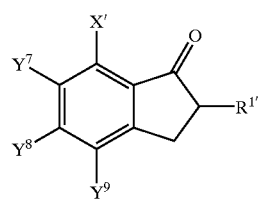

(III)

$R^1$ is methyl, ethyl, isopropyl, n—butyl or sec.—butyl, $R^3$ is 4—(tert.—butyl)phenyl, $Y^4$, $Y^5$ and $Y^6$ are hydrogen.

* * * * *

UNITED STATES PATENT AND TRADEMARK OFFICE
CERTIFICATE OF CORRECTION

PATENT NO.    : 6,492,539 B1
DATED         : December 10, 2002
INVENTOR(S)   : Bingel et al.

It is certified that error appears in the above-identified patent and that said Letters Patent is hereby corrected as shown below:

Column 77,
Line 31, "wich" should be -- which --.

Column 78,
Delete the material on lines 4-10, leaving only -- $C_2$-$C_{10}$- --.
Line 50, "groups bear" should be -- groups which may bear --.

Column 80,
Line 21, "x" should be -- X --.

Column 81,
Line 39, "$R^{1'}$" should be -- $R^{1''}$ --.
Line 67, delete the line.

Column 82,
Delete the material on lines 1-15;
Line 16, delete "titanium,";
Line 17, delete "or different";
Delete the material on lines 18-25, leaving only "a halogen atom";
Line 26, delete "zero or";
Line 40, delete "germanium or tin,";
Line 41, delete ", 2 or 3," and substitute -- or 2, --;
Line 43, delete "a halogen atom or";
Delete the material on lines 44-49 and substitute -- $C_8$-$C_{14}$-aryl, wherein radicals having the same designation on the two indenyl ligands can be identical or can be different --.
Delete lines 54 and 55 and substitute: -- $R^1$ is methyl, ethyl, isopropyl, n-butyl or sec-butyl --.
Delete line 61 and substitute -- $R^9$ and $R^{10}$ are identical and are each hydrogen --;
Line 62, after "$Y^6$" insert -- are idenitical and are --;
Line 63, after "phenyl" insert -- and --;
Delete last line "x=1".
Delete lines 22-32.

UNITED STATES PATENT AND TRADEMARK OFFICE
CERTIFICATE OF CORRECTION

PATENT NO.    : 6,492,539 B1
DATED         : December 10, 2002
INVENTOR(S)   : Bingel et al.

It is certified that error appears in the above-identified patent and that said Letters Patent is hereby corrected as shown below:

<u>Column 84,</u>
Delete lines 1-4.
Delete lines 10-13 and substitute -- $R^3$ is 4-(tert-butyl)phenyl and $Y^4$, $Y^5$ and $Y^6$ are each hydrogen --.
Delete the formula on lines 17-26.

Signed and Sealed this

Thirteenth Day of May, 2003

JAMES E. ROGAN
*Director of the United States Patent and Trademark Office*